US009818951B2

(12) United States Patent
Lee et al.

(10) Patent No.: US 9,818,951 B2
(45) Date of Patent: Nov. 14, 2017

(54) POLYCYCLIC COMPOUND AND ORGANIC ELECTRONIC DEVICE COMPRISING THE SAME

(71) Applicant: LG CHEM, LTD., Seoul (KR)

(72) Inventors: Dong Hoon Lee, Daejeon (KR); Minyoung Kang, Daejeon (KR); Jungi Jang, Daejeon (KR); Boonjae Jang, Daejeon (KR); Minseung Chun, Daejeon (KR); Kidong Koo, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/215,005

(22) Filed: Jul. 20, 2016

(65) Prior Publication Data

US 2016/0329500 A1   Nov. 10, 2016

Related U.S. Application Data

(63) Continuation of application No. 14/126,760, filed as application No. PCT/KR2013/006481 on Jul. 19, 2013, now Pat. No. 9,484,539.

(30) Foreign Application Priority Data

Jul. 19, 2012 (KR) .................. 10-2012-0078820

(51) Int. Cl.
| H01L 51/54 | (2006.01) |
| C09K 11/06 | (2006.01) |
| H01L 51/00 | (2006.01) |
| C07C 255/52 | (2006.01) |
| C07D 217/14 | (2006.01) |
| C07D 221/12 | (2006.01) |
| C07D 213/57 | (2006.01) |
| C07D 333/76 | (2006.01) |
| C07D 307/91 | (2006.01) |
| H05B 33/10 | (2006.01) |
| H01L 51/50 | (2006.01) |

(52) U.S. Cl.
CPC ........ *H01L 51/0058* (2013.01); *C07C 255/52* (2013.01); *C07D 213/57* (2013.01); *C07D 217/14* (2013.01); *C07D 221/12* (2013.01); *C07D 307/91* (2013.01); *C07D 333/76* (2013.01); *C09K 11/06* (2013.01); *H01L 51/0052* (2013.01); *H01L 51/0056* (2013.01); *H01L 51/0067* (2013.01); *H01L 51/0072* (2013.01); *H01L 51/0073* (2013.01); *H01L 51/0074* (2013.01); *H05B 33/10* (2013.01); *C07C 2603/18* (2017.05); *C07C 2603/24* (2017.05); *C07C 2603/26* (2017.05); *C07C 2603/97* (2017.05); *C09K 2211/1007* (2013.01); *C09K 2211/1011* (2013.01); *C09K 2211/1029* (2013.01); *C09K 2211/1088* (2013.01); *C09K 2211/1092* (2013.01); *H01L 51/5076* (2013.01); *H01L 51/5092* (2013.01); *Y02E 10/549* (2013.01)

(58) Field of Classification Search
CPC ................ C07C 255/49; C07C 255/52; C07C 2103/00; C07C 2103/04; C07C 2103/18; C07C 2103/24; C07C 2103/26; C07D 213/00; C07D 213/54; C07D 213/57; C07D 217/00; C07D 217/12; C07D 217/14; C07D 221/00; C07D 221/12; C07D 307/00; C07D 307/91; C07D 333/00; C07D 333/76; C09K 11/06; C09K 2211/00; C09K 2211/1011; C09K 2211/1014; C09K 2211/1018; H01L 51/0032; H01L 51/005; H01L 51/0051; H01L 51/0052; H01L 51/0058; H01L 51/0062; H01L 51/0065; H01L 51/0067; H01L 51/0068; H01L 51/0071; H01L 51/0072; H01L 51/0073; H01L 51/0074; H01L 51/50; H01L 51/5012; H01L 51/5048; H01L 51/5052; H01L 51/5056; H01L 51/506; H01L 51/5072; H01L 51/5076; H01L 51/5088; H01L 51/5092
USPC ....... 428/609, 691, 917, 411.4, 336; 427/58, 427/66; 313/40, 88–104, 313/E51.001–E51.052; 257/40, 88–104, 257/E51.001–E51.052; 252/301.16–301.35; 558/422, 425; 546/285, 144, 109, 264; 549/43, 460
See application file for complete search history.

(56) References Cited

U.S. PATENT DOCUMENTS

| 2002/0177009 A1 | 11/2002 | Suzuki et al. |
| 2003/0087126 A1 | 5/2003 | Ishida et al. |
| 2003/0134147 A1 | 7/2003 | Burn et al. |
| 2006/0134460 A1 | 6/2006 | Kondakova et al. |

(Continued)

FOREIGN PATENT DOCUMENTS

| CN | 102576814 A | 7/2012 |
| JP | 2002-329580 A | 11/2001 |
| JP | 2003-109765 A | 4/2003 |

(Continued)

OTHER PUBLICATIONS

De-Ming Han et al.: "Theoretical study of the one- and two-photon absorption properties of two series of fluorene derivatives", Science Direct, Chemical Physical Letters 453 (2008), pp. 129-135.

*Primary Examiner* — Andrew K Bohaty
(74) *Attorney, Agent, or Firm* — Dentons US LLP

(57) ABSTRACT

An exemplary embodiment of the present application provides a new compound and an organic electronic device using the same. The organic electronic device according to an exemplary embodiment of the present application shows excellent characteristics in terms of efficiency, driving voltage, and service life.

10 Claims, 3 Drawing Sheets

(56) References Cited

U.S. PATENT DOCUMENTS

2012/0256172 A1   10/2012   Ito et al.
2013/0200338 A1   8/2013    Kim et al.

FOREIGN PATENT DOCUMENTS

| JP | 2003-138251 A | 5/2003 |
| JP | 2013-159611 A | 8/2013 |
| KR | 2000-0051826 A | 8/2000 |
| TW | 201213502 A | 4/2012 |
| WO | 03/012890 A2 | 2/2003 |
| WO | 2004/020371 A1 | 3/2004 |
| WO | 2012/017680 A1 | 2/2012 |

[Figure 1]
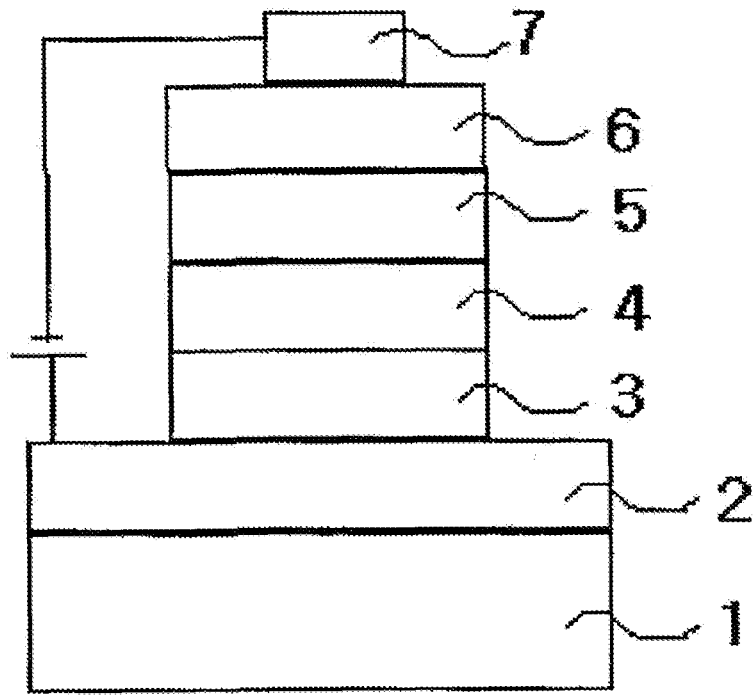
[Figure 2]
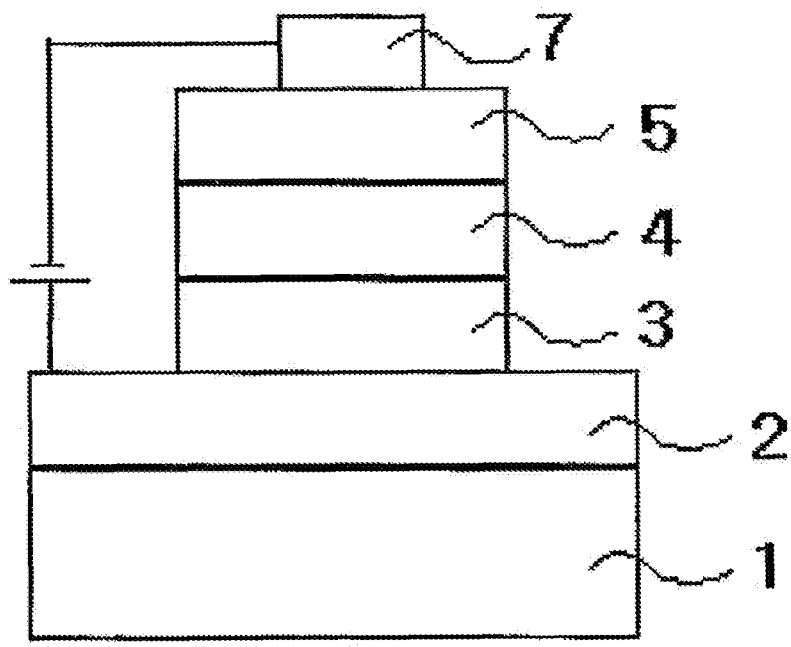

[Figure 3]
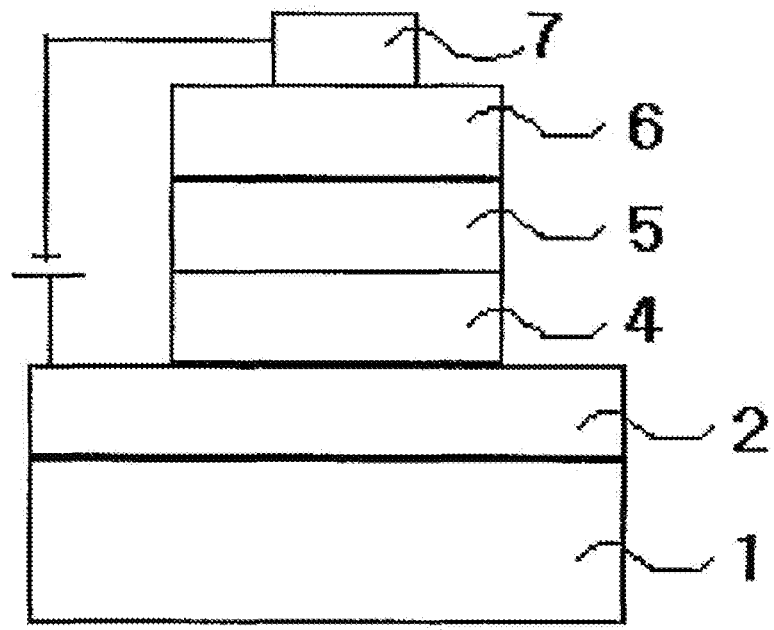
[Figure 4]
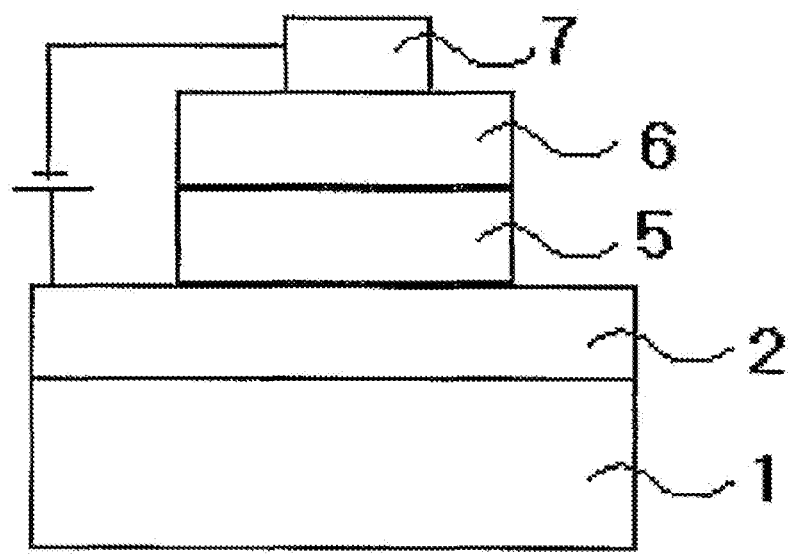

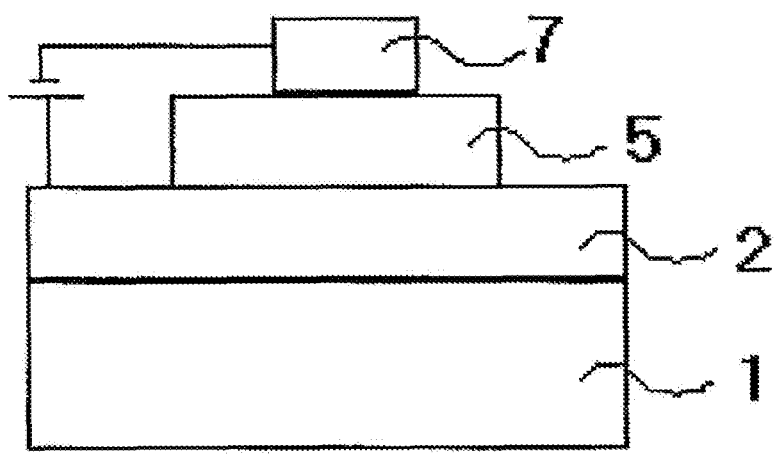
[Figure 5]

POLYCYCLIC COMPOUND AND ORGANIC ELECTRONIC DEVICE COMPRISING THE SAME

CROSS-REFERENCE TO RELATED APPLICATIONS

This application is a continuation application of U.S. patent application Ser. No. 14/126,760, filed Dec. 16, 2013, which application is a National Stage Entry of International Application No. PCT/KR2013/006481, filed Jul. 19, 2013, and claims the benefit of, and priority to, Korean Application No. 10-2012-0078820, filed Jul. 19, 2012, all of which are incorporated herein by reference in their entirety for all purposes as if fully set forth herein.

TECHNICAL FIELD

The present invention relates to a new polycyclic compound and an organic electronic device including the same.

BACKGROUND ART

An organic electronic device means a device that requires exchange of electric charges between electrodes and organic materials using holes and/or electrons. The organic electronic device may be largely divided into the following two categories according to an operation principle. First, there is an electronic device in which an exiton is formed in an organic material layer by a photon that flows from an external light source to the device, the exiton is separated into electrons and holes, and the electrons and the holes are respectively transferred to different electrodes and used as a current source (voltage source). Second, there is an electronic device in which holes and/or electrons are injected into an organic material semiconductor forming an interface with the electrode by applying a voltage or a current to two or more electrodes, and the device is operated by the injected electrons and holes.

In order for the organic electronic device to sufficiently exhibit the above-described excellent properties, a material constituting the organic material layer in the device needs to be supported by stable and efficient materials above anything else, but the development of a stable and efficient organic material layer material for an organic electronic device has not been sufficiently made. Therefore, there is a continuous need for developing a new material.

SUMMARY OF THE INVENTION

The present application has been made in an effort to provide a compound having a new structure, which is included in an organic material layer of an organic electronic device and thus may exhibit effects of enhancing the efficiency of the device, dropping a driving voltage thereof, increasing stability thereof, and the like, and an organic electronic device including the same.

An exemplary embodiment of the present application provides a compound represented by the following Formula 1.

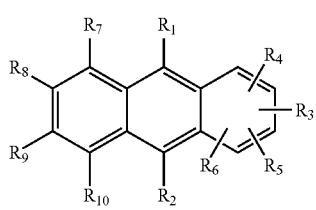

[Formula 1]

In Formula 1, $R_1$ and $R_2$ are the same as or different from each other, and are each independently a substituted or unsubstituted alkenyl group; a substituted or unsubstituted aryl group; a substituted or unsubstituted fluorenyl group; or a substituted or unsubstituted heterocyclic group including one or more of N, O, and S atoms, $R_3$ to $R_{10}$ are the same as or different from each other, and are each independently hydrogen; deuterium; a halogen group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted alkylthioxy group; a substituted or unsubstituted arylthioxy group; a substituted or unsubstituted alkenyl group; a substituted or unsubstituted aryl group; a substituted or unsubstituted fluorenyl group; or a substituted or unsubstituted heterocyclic group including one or more of N, O, and S atoms, at least one of $R_1$ to $R_3$ is a group of the following Formula 2,

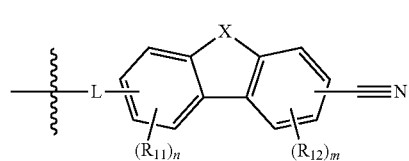

[Formula 2]

X is O, S, or $CR_aR_b$, $R_a$, $R_b$, $R_{11}$, and $R_{12}$ are the same as or different from each other, and are each independently hydrogen; deuterium; a halogen group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted alkylthioxy group; a substituted or unsubstituted arylthioxy group; a substituted or unsubstituted alkenyl group; a substituted or unsubstituted aryl group; a substituted or unsubstituted fluorenyl group; or a substituted or unsubstituted heterocyclic group including one or more of N, O, and S atoms, and two or more adjacent groups among $R_a$, $R_b$, $R_{11}$, and $R_{12}$ may be bonded to each other to form a monocyclic or polycyclic ring, L is a direct bond; a substituted or unsubstituted arylene group; a substituted or unsubstituted alkenylene group; a substituted or unsubstituted fluorenylene group; or a substituted or unsubstituted heteroarylene group including one or more of N, O, and S atoms, and n and m are each independently an integer from 0 to 3.

Another exemplary embodiment of the present application provides an organic electronic device including a first electrode, a second electrode, and an organic material layer having one or more layers disposed between the first electrode and the second electrode, in which one or more layers of the organic material layer include the compound.

The new compound according to an exemplary embodiment of the present application may be used as a material for an organic material layer of the organic electronic device, and an organic electronic device using the same shows excellent characteristics in terms of efficiency, driving voltage, service life, and the like.

The new compound according to an exemplary embodiment of the present application may be used either purely or by being mixed with impurities in an organic electronic device including an organic light emitting device, and particularly, shows excellent characteristics having a deep HOMO level and hole stability, and thus is advantageous in improving optical efficiency.

The new compound according to an exemplary embodiment of the present application has excellent thermal stability, thereby improving stability of the device.

BRIEF DESCRIPTION OF THE DRAWINGS

FIGS. 1 to 5 are cross-sectional views illustrating a structure of an organic electronic device according to an exemplary embodiment of the present application.

DETAILED DESCRIPTION

Hereinafter, the present application will be described in more detail.

An exemplary embodiment of the present application provides a compound represented by the following Formula 1.

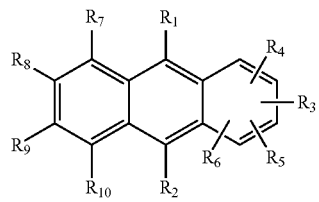

[Formula 1]

In Formula 1, $R_1$ and $R_2$ are the same as or different from each other, and are each independently a substituted or unsubstituted alkenyl group; a substituted or unsubstituted aryl group; a substituted or unsubstituted fluorenyl group; or a substituted or unsubstituted heterocyclic group including one or more of N, O, and S atoms, $R_3$ to $R_{10}$ are the same as or different from each other, and are each independently hydrogen; deuterium; a halogen group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted alkylthioxy group; a substituted or unsubstituted arylthioxy group; a substituted or unsubstituted alkenyl group; a substituted or unsubstituted aryl group; a substituted or unsubstituted fluorenyl group; or a substituted or unsubstituted heterocyclic group including one or more of N, O, and S atoms, at least one of $R_1$ to $R_3$ is a group of the following Formula 2,

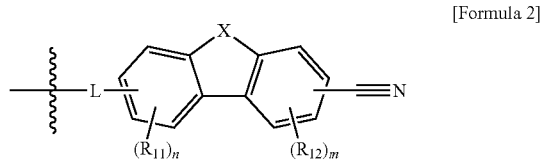

[Formula 2]

X is O, S, or $CR_aR_b$, $R_a$, $R_b$, $R_{11}$, and $R_{12}$ are the same as or different from each other, and are each independently hydrogen; deuterium; a halogen group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted alkylthioxy group; a substituted or unsubstituted arylthioxy group; a substituted or unsubstituted alkenyl group; a substituted or unsubstituted aryl group; a substituted or unsubstituted fluorenyl group; or a substituted or unsubstituted heterocyclic group including one or more of N, O, and S atoms, and two or more adjacent groups among $R_a$, $R_b$, $R_{11}$, and $R_{12}$ may be bonded to each other to form a monocyclic or polycyclic ring, L is a direct bond; a substituted or unsubstituted arylene group; a substituted or unsubstituted alkenylene group; a substituted or unsubstituted fluorenylene group; or a substituted or unsubstituted heteroarylene group including one or more of N, O, and S atoms, and n and m are each independently an integer from 0 to 3.

In an exemplary embodiment of the present application, the compound represented by Formula 1 may be a compound represented by any one of the following Formulae 3 to 8.

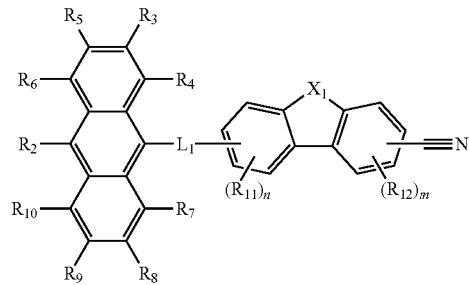

[Formula 3]

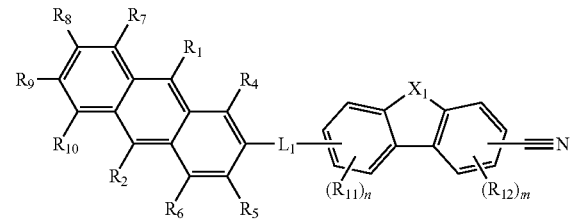

[Formula 4]

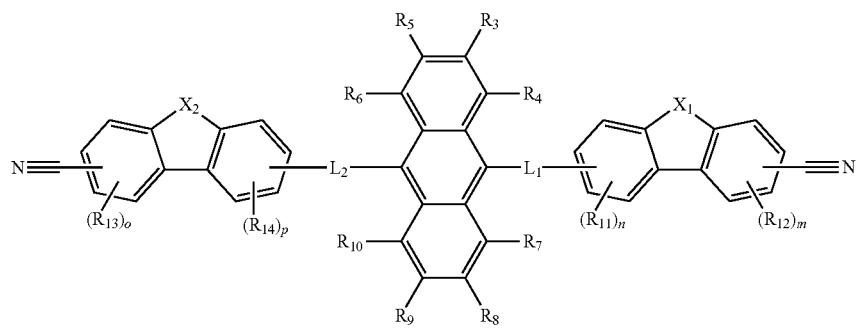

[Formula 5]

-continued

[Formula 6]

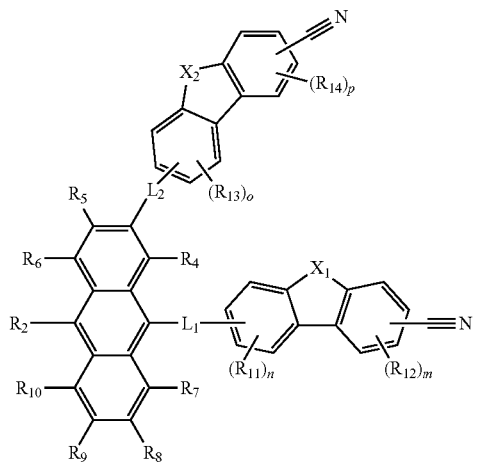

[Formula 7]

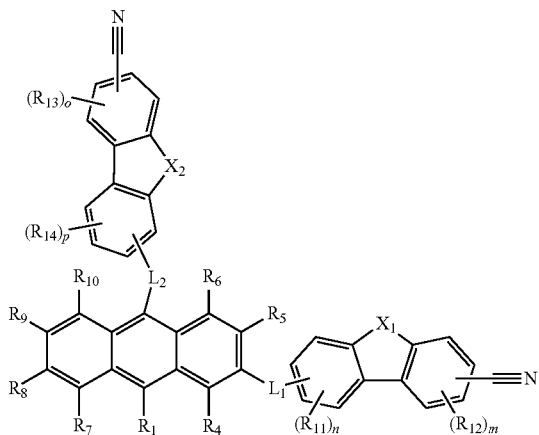

[Formula 8]

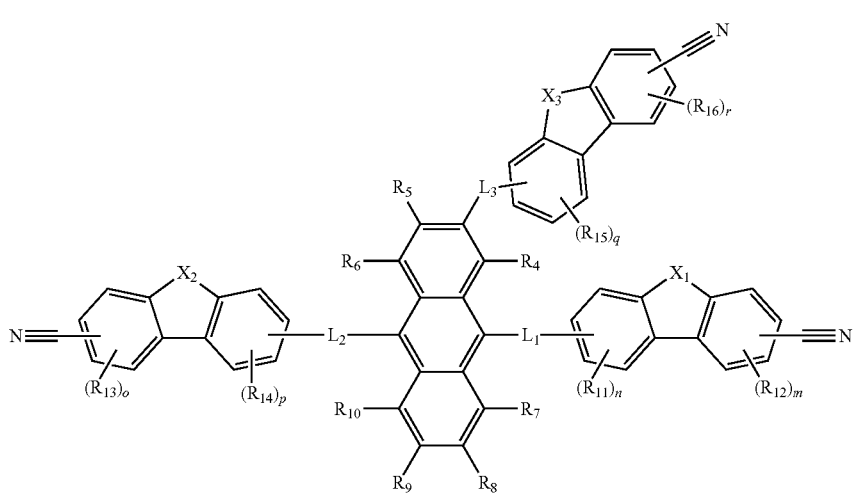

In Formulae 3 to 8, $X_1$ to $X_3$ are each independently O, S, or $CR_aR_b$, $R_1$ to $R_{12}$, $R_a$, $R_b$, n, and m are the same as those defined in claim 1, $R_{13}$ to $R_{16}$ are the same as or different from each other, and are each independently hydrogen; deuterium; a halogen group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted alkylthioxy group; a substituted or unsubstituted arylthioxy group; a substituted or unsubstituted alkenyl group; a substituted or unsubstituted aryl group; a substituted or unsubstituted fluorenyl group; or a substituted or unsubstituted heterocyclic group including one or more of N, O, and S atoms, and two or more adjacent groups among $R_1$ to $R_{16}$, $R_a$, and $R_b$ may be bonded to each other to form a monocyclic or polycyclic ring, $L_1$ to $L_3$ are each independently a direct bond; a substituted or unsubstituted arylene group; a substituted or unsubstituted alkenylene group; a substituted or unsubstituted fluorenylene group; or a substituted or unsubstituted heteroarylene group including one or more of N, O, and S atoms, and o, p, q, and r are each independently an integer from 0 to 3.

Examples of the substituents will be described below, but are not limited thereto.

In an exemplary embodiment of the present application, the alkyl group may be straight or branched. The carbon number of the alkyl group is not particularly limited, but is preferably 1 to 30 which is a range that does not cause a steric hindrance. Specific examples thereof include a methyl group, an ethyl group, an n-propyl group, an isopropyl group, an n-butyl group, a sec-butyl group, a t-butyl group, an n-pentyl group, an iso-pentyl group, a neo-pentyl group, an n-hexyl group, and the like, but are not limited thereto.

In an exemplary embodiment of the present application, the alkoxy group may be straight, branched, or cyclic. The carbon number of the alkoxy group is not particularly limited, but is preferably from 1 to 30 which is a range that does not cause a steric hindrance. For example, the number of carbon atoms of the alkoxy group does not affect a conjugate length of a compound, but only affects a method of applying a compound to an organic electronic device, for example, an application of a vacuum deposition method or a solution coating method. Therefore, the number of carbon atoms of the alkoxy group is not particularly limited. Specific examples thereof include a methoxy group, an ethoxy group, an n-propyloxy group, an iso-propyloxy group, an n-butyloxy group, a cyclopentyloxy group, and the like, but are not limited thereto.

In an exemplary embodiment of the present application, the alkenyl group may be straight or branched, and is preferably an alkenyl group having from 2 to 40 carbon atoms, and specifically, and particularly, is preferably an alkenyl group in which an aryl group, such as a stylbenyl group and a styrenyl group, is substituted, but is not limited thereto.

In an exemplary embodiment of the present application, the aryl group may be monocyclic or polycyclic, and the carbon number thereof is not particularly limited, but is preferably 6 to 60. Examples of the monocyclic aryl group include a phenyl group, a biphenyl group, a terphenyl group, a stilbene group, and the like, and examples of the polycyclic aryl group include a naphthyl group, an anthracenyl group, a phenanthrenyl group, a pyrenyl group, a perylenyl group, a tetracenyl group, a chrysenyl group, a fluorenyl group, an acenaphthacenyl group, a triphenylene group, a fluoranthrene group, and the like, but the scope of the present application is not limited to these examples.

In an exemplary embodiment of the present application, the heterocyclic group is a heterocyclic group including one or more of O, N, and S as a heteroatom, and the carbon number thereof is not particularly limited, but is preferably from 2 to 60. Examples of the heterocyclic group include a thiophene group, a furan group, a pyrrole group, an imidazole group, a triazole group, an oxazole group, an oxadiazole group, a triazole group, a pyridyl group, a bipyridyl group, a triazine group, an acrydyl group, a pyridazine group, a quinolinyl group, an isoquinoline group, an indole group, a carbazole group, a benzoxazole group, a benzimidazole group, a benzthiazole group, a benzcarbazole group, a benzthiophene group, a dibenzothiophene group, a benzfuranyl group, a dibenzofuranyl group and the like, but are not limited thereto.

In an exemplary embodiment of the present application, the cycloalkyl group is not particularly limited, but the carbon number thereof is preferably from 3 to 60. A cyclopentyl group and a cyclohexyl group are particularly preferred.

In an exemplary embodiment of the present application, examples of the halogen group include fluorine, chlorine, bromine, or iodine.

In an exemplary embodiment of the present application, the fluorenyl group is a structure in which two cyclic organic compounds are linked to each other through one atom, and examples thereof include

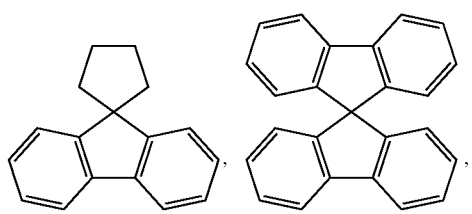

and the like.

In an exemplary embodiment of the present application, the fluorenyl group includes a structure of an open fluorenyl group, and the open fluorenyl group herein is a structure in which the link of one cyclic compound is broken in a structure in which two cyclic organic compounds are linked to each other through one atom, and examples thereof include

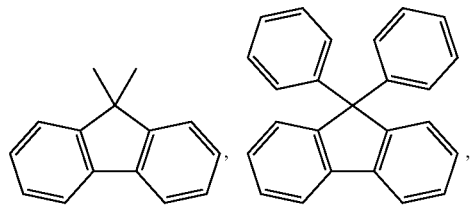

and the like.

In an exemplary embodiment of the present application, the arylene group, the alkenylene group, the fluorenylene group, and the heteroarylene group are a divalent group of an aryl group, an alkenyl group, a fluorenyl group, and a heteroaryl group, respectively. Except that these groups are each a divalent group, the above-described description of the aryl group, the alkenyl group, the fluorenyl group, and the heteroaryl group may be applied to these groups.

In an exemplary embodiment of the present application, the substituted arylene group means that a phenyl group, a biphenyl group, a naphthalene group, a fluorene group, a pyrene group, a phenanthrene group, a perylene group, a tetracene group, an anthracene group, and the like are substituted with another substituent.

In an exemplary embodiment of the present application, the substituted heteroarylene group means that a pyridyl group, a thiophene group, a triazine group, a quinoline group, a phenanthroline group, an imidazole group, a thiazole group, an oxazole group, a carbazole group, and a condensed heterocyclic group thereof, for example, a benzoquinoline group, a benzimidazole group, a benzoxazole group, a benzthiazole group, a benzcarbazole group, a dibenzothiophenyl group, a dibenzofuran group, and the like are substituted with another substituent.

Further, as used herein, the term "substituted or unsubstituted" means that a group is substituted with one or more substituents selected from the group consisting of deuterium; a halogen group; an alkyl group; an alkenyl group; an alkoxy group; a cycloalkyl group; a silyl group; an arylalkenyl group; an aryl group; an aryloxy group; an alkylthioxy group; an alkylsulfoxy group; an arylsulfoxy group; a boron group; an alkylamine group; an aralkylamine group; an arylamine group; a heteroaryl group; a carbazole group; an arylamine group; an aryl group; a fluorenyl group; a nitrile group; a nitro group; a hydroxyl group; a cyano group; and a heterocyclic group including one or more of N, O, S, and P atoms, or has no substituent.

As used herein,

means a moiety bonded (linked) to another substituent or a bonding moiety.

In an exemplary embodiment of the present application, at least one of $R_1$ and $R_2$ in Formulae 1 to 8 may be each independently a substituted or unsubstituted aryl group, or a substituted or unsubstituted heteroaryl group. Specifically, at least one of $R_1$ and $R_2$ may be each independently a substituted or unsubstituted phenyl group, a substituted or unsubstituted biphenyl group, a substituted or unsubstituted terphenyl group, a substituted or unsubstituted pyridyl group, a substituted or unsubstituted quinoline group, a substituted or unsubstituted phenanthrenyl group, a substituted or unsubstituted naphthyl group, or a substituted or unsubstituted phenanthridine group.

The substituents of $R_1$ and $R_2$ may be each independently one or more substituents selected from the group consisting of hydrogen; deuterium; a halogen group; an aryl group unsubstituted or substituted with deuterium; and a heterocyclic group including one or more of N, O, S, and P atoms. More specifically, the substituents of $R_1$ and $R_2$ may be each independently hydrogen, deuterium, fluoro, a phenyl group, a phenyl group substituted with deuterium, a naphthyl group, or a pyridyl group.

More specifically, at least one of $R_1$ and $R_2$ may be each independently deuterium, fluoro, a phenyl group, a phenyl group substituted with deuterium, a naphthyl group, a phenanthrenyl group, or a phenyl group unsubstituted or substituted with a pyridyl group; a biphenyl group; a terphenyl group; a pyridyl group; a quinoline group; a phenanthrenyl group; a naphthyl group unsubstituted or substituted with a phenyl group or a naphthyl group; or a phenanthridine group.

In an exemplary embodiment of the present application, $R_2$ in Formulae 3, 4, and 6 may be a substituted or unsubstituted aryl group, or a substituted or unsubstituted heteroaryl group. Specifically, $R_2$ may be a substituted or unsubstituted phenyl group, a substituted or unsubstituted biphenyl group, a substituted or unsubstituted terphenyl group, a substituted or unsubstituted pyridyl group, a substituted or unsubstituted quinoline group, a substituted or unsubstituted phenanthrenyl group, a substituted or unsubstituted naphthyl group, or a substituted or unsubstituted phenanthridine group.

The substituents of $R_2$ may be one or more substituents selected from the group consisting of hydrogen; deuterium; a halogen group; an aryl group unsubstituted or substituted with deuterium; and a heterocyclic group including one or more of N, O, S, and P atoms. More specifically, the substituent of $R_2$ may be hydrogen, deuterium, fluoro, a phenyl group, a phenyl group substituted with deuterium, a naphthyl group, or a pyridyl group.

More specifically, $R_2$ may be deuterium, fluoro, a phenyl group, a phenyl group substituted with deuterium, a naphthyl group, a phenanthrenyl group, or a phenyl group unsubstituted or substituted with a pyridyl group; a biphenyl group; a terphenyl group; a pyridyl group; a quinoline group; a phenanthrenyl group; a naphthyl group unsubstituted or substituted with a phenyl group or a naphthyl group; or a phenanthridine group.

In an exemplary embodiment of the present application, $R_1$ in Formulae 4 and 7 may be a substituted or unsubstituted aryl group, or a substituted or unsubstituted heteroaryl group. Specifically, $R_1$ may be a substituted or unsubstituted phenyl group, a substituted or unsubstituted biphenyl group, a substituted or unsubstituted terphenyl group, a substituted or unsubstituted pyridyl group, a substituted or unsubstituted quinoline group, a substituted or unsubstituted phenanthrenyl group, a substituted or unsubstituted naphthyl group, or a substituted or unsubstituted phenanthridine group.

The substituent of $R_1$ may be one or more substituents selected from the group consisting of hydrogen; deuterium; a halogen group; an aryl group unsubstituted or substituted with deuterium; and a heterocyclic group including one or more of N, O, S, and P atoms. More specifically, the substituent of $R_2$ may be hydrogen, deuterium, fluoro, a phenyl group, a phenyl group substituted with deuterium, a naphthyl group, or a pyridyl group.

More specifically, $R_1$ may be deuterium, fluoro, a phenyl group, a phenyl group substituted with deuterium, a naphthyl group, a phenanthrenyl group, or a phenyl group unsubstituted or substituted with a pyridyl group; a biphenyl group; a terphenyl group; a pyridyl group; a quinoline group; a phenanthrenyl group; a naphthyl group unsubstituted or substituted with a phenyl group or a naphthyl group; or a phenanthridine group.

In an exemplary embodiment of the present application, $R_1$ and $R_2$ in Formula 4 may be each independently a substituted or unsubstituted aryl group, or a substituted or unsubstituted heteroaryl group. Specifically, $R_1$ and $R_2$ may be each independently a substituted or unsubstituted phenyl group, a substituted or unsubstituted biphenyl group, a substituted or unsubstituted terphenyl group, a substituted or unsubstituted pyridyl group, a substituted or unsubstituted quinoline group, a substituted or unsubstituted phenanthrenyl group, a substituted or unsubstituted naphthyl group, or a substituted or unsubstituted phenanthridine group.

The substituents of $R_1$ and $R_2$ may be each independently one or more substituents selected from the group consisting of hydrogen; deuterium; a halogen group; an aryl group unsubstituted or substituted with deuterium; and a heterocyclic group including one or more of N, O, S, and P atoms. More specifically, the substituents of $R_1$ and $R_2$ may be each independently deuterium, fluoro, a phenyl group, a phenyl group substituted with deuterium, a naphthyl group, or a pyridyl group.

More specifically, $R_1$ and $R_2$ may be each independently deuterium, fluoro, a phenyl group, a phenyl group substituted with deuterium, a naphthyl group, a phenanthrenyl group, or a phenyl group unsubstituted or substituted with a pyridyl group; a biphenyl group; a terphenyl group; a pyridyl group; a quinoline group; a phenanthrenyl group; a naphthyl group unsubstituted or substituted with a phenyl group or a naphthyl group; or a phenanthridine group.

In Formulae 1, 3, 4, 6, and 7 according to an exemplary embodiment of the present application, at least one of $R_1$ and $R_2$ may be each independently selected from the group consisting of the following substituted or unsubstituted structural formulae. The following structural formulae are the least formulae, and are not limited thereto.

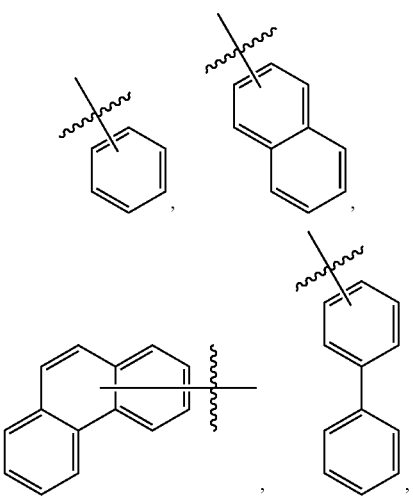

-continued

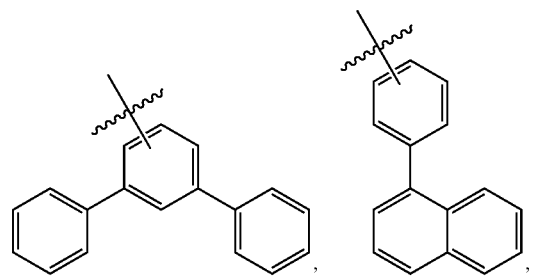
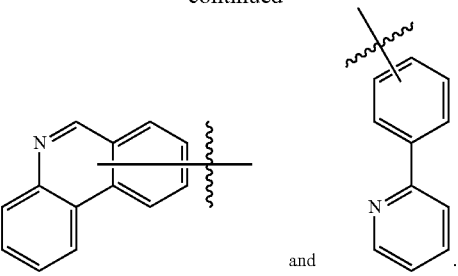
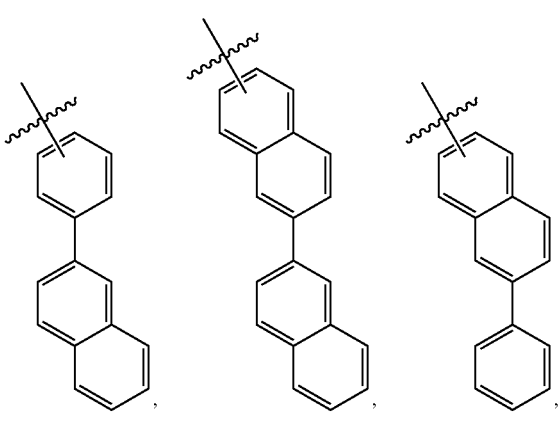
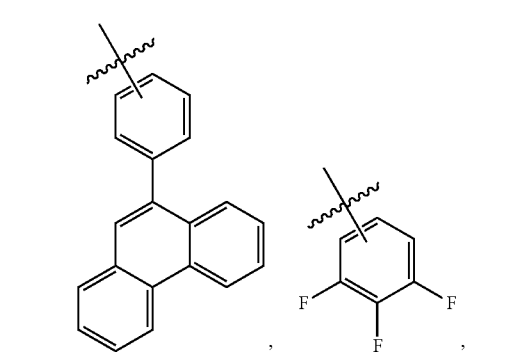
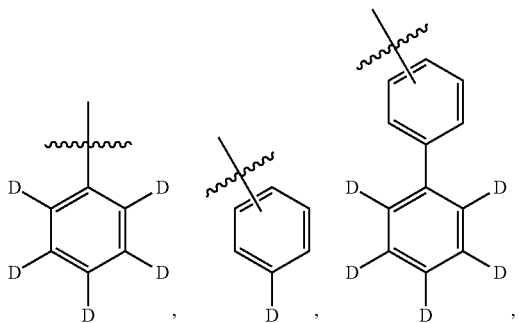
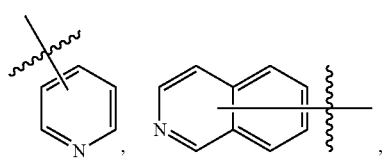

-continued

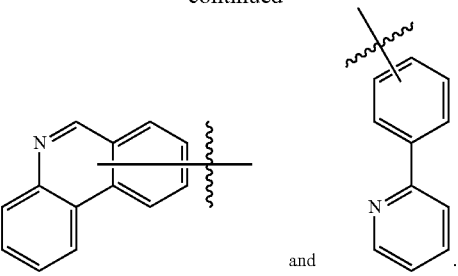

and

In an exemplary embodiment of the present application, $R_3$ to $R_{10}$ in Formulae 1, 3, and 5 may be each independently hydrogen, deuterium, a halogen group, or a nitrile group. In an exemplary embodiment of the present application, $R_3$ to $R_{10}$ in Formulae 1, 3, and 5 may be each independently a substituted or unsubstituted aryl group or heteroaryl group. Specifically, $R_3$ to $R_{10}$ may be each independently a substituted or unsubstituted phenyl group, a substituted or unsubstituted biphenyl group, a substituted or unsubstituted terphenyl group, a substituted or unsubstituted pyridyl group, a substituted or unsubstituted quinoline group, a substituted or unsubstituted phenanthrenyl group, or a substituted or unsubstituted naphthyl group.

In an exemplary embodiment of the present application, $R_4$ to $R_{10}$ in Formulae 4 and 6 to 8 may be each independently hydrogen, deuterium, a halogen group, or a nitrile group.

In an exemplary embodiment of the present application, $R_4$ to $R_{10}$ in Formulae 4 and 6 to 8 may be each independently a substituted or unsubstituted aryl group or a substituted or unsubstituted heteroaryl group. Specifically, $R_4$ to $R_{10}$ may be each independently a substituted or unsubstituted phenyl group, a substituted or unsubstituted biphenyl group, a substituted or unsubstituted terphenyl group, a substituted or unsubstituted pyridyl group, a substituted or unsubstituted quinoline group, a substituted or unsubstituted phenanthrenyl group, or a substituted or unsubstituted naphthyl group.

In an exemplary embodiment of the present application, $L_1$ to $L_3$ may be each independently a direct bond, a substituted or unsubstituted arylene group, a substituted or unsubstituted alkenylene group, a substituted or unsubstituted fluorenylene group, or a substituted or unsubstituted heteroarylene group having one or more of O, N, S, and P as a heteroatom. Specifically, $L_1$ to $L_3$ may be each independently a direct bond, a substituted or unsubstituted phenylene group, a substituted or unsubstituted naphthylene group, a substituted or unsubstituted fluorenylene group, a substituted or unsubstituted pyridylene group, or a substituted or unsubstituted biphenylene group. More specifically, $L_1$ to $L_3$ may be each independently a direct bond, a phenylene group, a naphthylene group, or a pyridylene group.

In an exemplary embodiment of the present application, when X or $X_1$ to $X_3$ of Formulae 2 to 8 is $CR_aR_b$, $R_a$ and $R_b$ may be each independently a substituted or unsubstituted alkyl group. Specifically, $R_5$ and $R_6$ may be each independently a substituted or unsubstituted methyl group, or a substituted or unsubstituted ethyl group. More specifically, $R_a$ and $R_b$ may be each independently a methyl group, or an ethyl group.

In an exemplary embodiment of the present application, when X or $X_1$ to $X_3$ of Formulae 2 to 8 is $CR_aR_b$, $R_a$ and $R_b$ may be each independently a substituted or unsubstituted aryl group, or a substituted or unsubstituted heteroaryl group. Specifically, $R_a$ and $R_b$ may be each independently a substituted or unsubstituted phenyl group, a substituted or unsubstituted biphenyl group, a substituted or unsubstituted terphenyl group, a substituted or unsubstituted pyridyl group, a substituted or unsubstituted quinoline group, a substituted or unsubstituted phenanthrenyl group, or a substituted or unsubstituted naphthyl group. More specifically, $R_a$ and $R_b$ may be each independently a phenyl group, or a pyridyl group.

In an exemplary embodiment of the present application, when X or $X_1$ to $X_3$ of Formulae 2 to 8 is $CR_aR_b$, $R_a$ and $R_b$ may be linked to each other to form a monocylic or polycyclic ring.

In an exemplary embodiment of the present application, $R_{11}$ and $R_{12}$ in Formulae 2 to 4 may be each independently hydrogen, deuterium, a halogen group, or a nitrile group.

In an exemplary embodiment of the present application, $R_{11}$ and $R_{12}$ in Formulae 2 to 4 may be each independently a substituted or unsubstituted aryl group, or a substituted or unsubstituted heteroaryl group. Specifically, $R_{11}$ and $R_{12}$ may be each independently a substituted or unsubstituted phenyl group, a substituted or unsubstituted biphenyl group, a substituted or unsubstituted terphenyl group, a substituted or unsubstituted pyridyl group, a substituted or unsubstituted quinoline group, a substituted or unsubstituted phenanthrenyl group, or a substituted or unsubstituted naphthyl group.

In an exemplary embodiment of the present application, $R_{11}$ to $R_{14}$ in Formulae 5 to 7 may be each independently hydrogen, deuterium, a halogen group, or a nitrile group.

In an exemplary embodiment of the present application, $R_{11}$ to $R_{14}$ in Formulae 5 to 7 may be each independently a substituted or unsubstituted aryl group, or a substituted or unsubstituted heteroaryl group. Specifically, $R_{11}$ to $R_{14}$ may be each independently a substituted or unsubstituted phenyl group, a substituted or unsubstituted biphenyl group, a substituted or unsubstituted terphenyl group, a substituted or unsubstituted pyridyl group, a substituted or unsubstituted quinoline group, a substituted or unsubstituted phenanthrenyl group, or a substituted or unsubstituted naphthyl group.

In an exemplary embodiment of the present application, $R_{11}$ to $R_{16}$ in Formula 8 may be each independently hydrogen, deuterium, a halogen group, or a nitrile group.

In an exemplary embodiment of the present application, $R_{11}$ to $R_{16}$ in Formula 8 may be each independently a substituted or unsubstituted aryl group, or a substituted or unsubstituted heteroaryl group. Specifically, $R_{11}$ to $R_{16}$ may be each independently a substituted or unsubstituted phenyl group, a substituted or unsubstituted biphenyl group, a substituted or unsubstituted terphenyl group, a substituted or unsubstituted pyridyl group, a substituted or unsubstituted quinoline group, a substituted or unsubstituted phenanthrenyl group, or a substituted or unsubstituted naphthyl group.

In Formula 3 according to an exemplary embodiment of the present application, $R_2$ is deuterium, fluoro, a phenyl group, a phenyl group substituted with deuterium, a naphthyl group, a phenanthrenyl group, or a phenyl group unsubstituted or substituted with a pyridyl group; a biphenyl group; a terphenyl group; a pyridyl group; a quinoline group; a phenanthrenyl group; a naphthyl group unsubstituted or substituted with a phenyl group or a naphthyl group; or a phenanthridine group, $R_3$ to $R_{12}$ are hydrogen, $X_1$ is O, S, or $CR_aR_b$, $R_a$ and $R_b$ are each independently a methyl group, an ethyl group, a phenyl group, or a pyridyl group, or are linked to each other to form a monocylic or polycyclic ring, and $L_1$ may be a direct bond, a phenylene group, a naphthylene group, or a pyridylene group.

In Formula 4 according to an exemplary embodiment of the present application, $R_1$ and $R_2$ are each independently deuterium, fluoro, a phenyl group, a phenyl group substituted with deuterium, a naphthyl group, a phenanthrenyl group, or a phenyl group unsubstituted or substituted with a pyridyl group; a biphenyl group; a terphenyl group; a pyridyl group; a quinoline group; a phenanthrenyl group; a naphthyl group unsubstituted or substituted with a phenyl group or a naphthyl group; or a phenanthridine group, $R_4$ to $R_{12}$ are hydrogen, $X_1$ is O, S, or $CR_aR_b$, $R_a$ and $R_b$ are each independently a methyl group, an ethyl group, a phenyl group, or a pyridyl group, or are linked to each other to form a monocylic or polycyclic ring, and $L_1$ may be a direct bond, a phenylene group, a naphthylene group, or a pyridylene group.

In Formula 5 according to an exemplary embodiment of the present application, $R_3$ is deuterium, fluoro, a phenyl group, a phenyl group substituted with deuterium, a naphthyl group, a phenanthrenyl group, or a phenyl group unsubstituted or substituted with a pyridyl group; a biphenyl group; a terphenyl group; a pyridyl group; a quinoline group; a phenanthrenyl group; a naphthyl group unsubstituted or substituted with a phenyl group or a naphthyl group; or a phenanthridine group, $R_4$ to $R_{14}$ are hydrogen, $X_1$ and $X_2$ are each independently O, S, or $CR_aR_b$, $R_a$ and $R_b$ are each independently a methyl group, an ethyl group, a phenyl group, or a pyridyl group, or are linked to each other to form a monocylic or polycyclic ring, and $L_1$ and $L_2$ may be each independently a direct bond, a phenylene group, a naphthylene group, or a pyridylene group.

In Formula 6 according to an exemplary embodiment of the present application, $R_2$ is deuterium, fluoro, a phenyl group, a phenyl group substituted with deuterium, a naphthyl group, a phenanthrenyl group, or a phenyl group unsubstituted or substituted with a pyridyl group; a biphenyl group; a terphenyl group; a pyridyl group; a quinoline group; a phenanthrenyl group; a naphthyl group unsubstituted or substituted with a phenyl group or a naphthyl group; or a phenanthridine group, $R_4$ to $R_{14}$ are hydrogen, $X_1$ and $X_2$ are each independently O, S, or $CR_aR_b$, $R_a$ and $R_b$ are each independently a methyl group, an ethyl group, a phenyl group, or a pyridyl group, or are linked to each other to form a monocylic or polycyclic ring, and $L_1$ and $L_2$ may be each independently a direct bond, a phenylene group, a naphthylene group, or a pyridylene group.

In Formula 7 according to an exemplary embodiment of the present application, $R_1$ is deuterium, fluoro, a phenyl group, a phenyl group substituted with deuterium, a naphthyl group, a phenanthrenyl group, or a phenyl group unsubstituted or substituted with a pyridyl group; a biphenyl group; a terphenyl group; a pyridyl group; a quinoline group; a phenanthrenyl group; a naphthyl group unsubstituted or substituted with a phenyl group or a naphthyl group; or a phenanthridine group, $R_4$ to $R_{14}$ are hydrogen, $X_1$ and $X_2$ are each independently O, S, or $CR_aR_b$, $R_a$ and $R_b$ are each independently a methyl group, an ethyl group, a phenyl group, or a pyridyl group, or are linked to each other to form a monocylic or polycyclic ring, and $L_1$ and $L_2$ may be each independently a direct bond, a phenylene group, a naphthylene group, or a pyridylene group.

In Formula 8 according to an exemplary embodiment of the present application, $R_4$ to $R_{16}$ are hydrogen, $X_1$ to $X_3$ are each independently O, S, or $CR_aR_b$, $R_a$ and $R_b$ are each independently a methyl group, an ethyl group, a phenyl group, or a pyridyl group, or $R_{11}$ and $R_{12}$, $R_{15}$ and $R_{16}$, and $R_{19}$ and $R_{20}$ are each independently linked to each other to form a monocylic or polycyclic ring, and $L_1$, $L_2$, and $L_3$ may be each independently a direct bond, a phenylene group, a naphthylene group, or a pyridylene group.

In an exemplary embodiment of the present application, Formula 2 may be expressed by the following Formula 9.

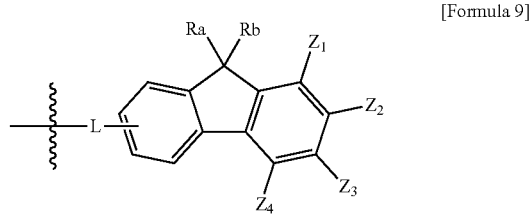

[Formula 9]

In Formula 9, L, $R_a$, and $R_b$ are the same as those defined in Formula 2, any one of $Z_1$ to $Z_4$ is —CN, and the others are the same as or different from each other, and are each independently hydrogen; deuterium; a halogen group; a nitro group; a hydroxyl group; a substituted or unsubstituted alkyl group; a substituted or unsubstituted cycloalkyl group; a substituted or unsubstituted alkoxy group; a substituted or unsubstituted alkylthioxy group; a substituted or unsubstituted arylthioxy group; a substituted or unsubstituted alkenyl group; a substituted or unsubstituted aryl group; a substituted or unsubstituted fluorenyl group; or a substituted or unsubstituted heterocyclic group including one or more of N, O, and S atoms.

The compound of Formula 1 according to an exemplary embodiment of the present application has a high glass transition temperature (Tg), and thus has excellent thermal stability. The improvement in thermal stability is an important factor which provides driving stability to a device.

In addition, when Formula 2 is introduced into the compound of Formula 1, Formula 2 delocalizes electrons with an appropriate intensity, and therefore the compound appears to exhibit excellent performance in terms of efficiency, driving voltage, stability, and the like. In particular, the compound has excellent thermal stability, a deep HOMO level, and hole stability, and thus shows excellent characteristics.

The compound of Formula 1 according to an exemplary embodiment of the present application may be used as an organic material layer in an organic electronic device due to the structural specificity thereof.

Specific examples of the compound according to an exemplary embodiment of the present application include the compounds in the following Table 1, but are not limited thereto.

TABLE 1

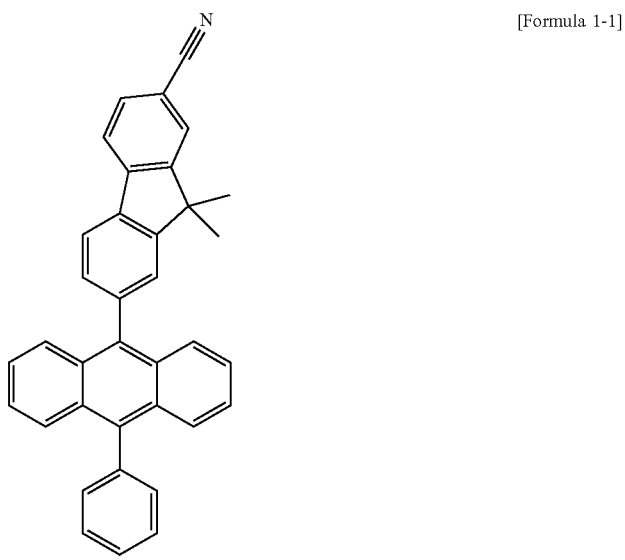

[Formula 1-1]

TABLE 1-continued
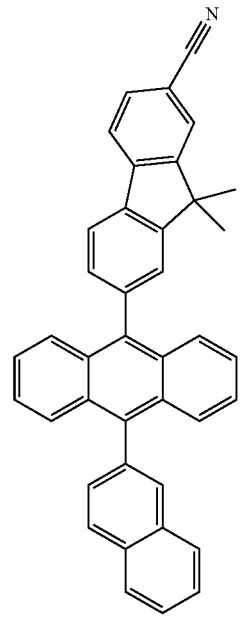 [SMILES: CC1(C)c2cc(C#N)ccc2-c2ccc(-c3c4ccccc4c(-c4ccc5ccccc5c4)c4ccccc34)cc21]
[Formula 1-2]
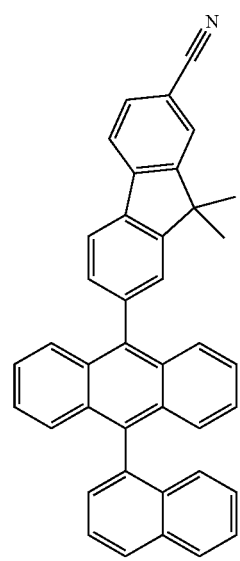 [SMILES: CC1(C)c2cc(C#N)ccc2-c2ccc(-c3c4ccccc4c(-c4cccc5ccccc45)c4ccccc34)cc21]
[Formula 1-3]

TABLE 1-continued
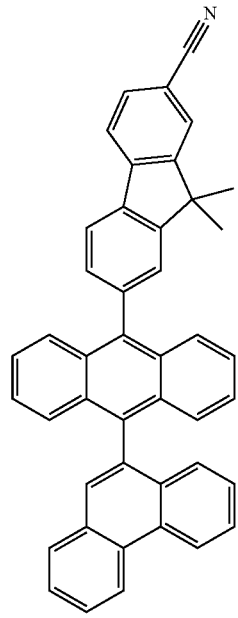 [SMILES: CC1(C)c2cc(C#N)ccc2-c2ccc(-c3c4ccccc4c(-c4cc5ccccc5c5ccccc45)c4ccccc34)cc21]
[Formula 1-4]
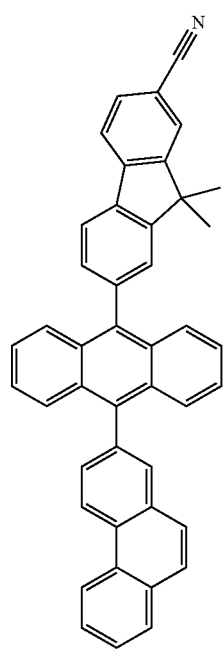 [SMILES: CC1(C)c2cc(C#N)ccc2-c2ccc(-c3c4ccccc4c(-c4ccc5c(ccc6ccccc65)c4)c4ccccc34)cc21]
[Formula 1-5]

TABLE 1-continued
[Formula 1-6]
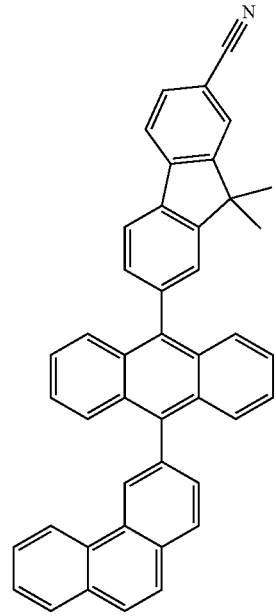 [SMILES: CC1(C)c2cc(C#N)ccc2-c2ccc(-c3c4ccccc4c(-c4ccc5ccc6ccccc6c5c4)c4ccccc34)cc21]
[Formula 1-7]
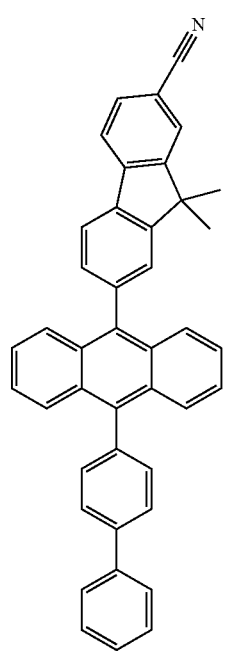 [SMILES: CC1(C)c2cc(C#N)ccc2-c2ccc(-c3c4ccccc4c(-c4ccc(-c5ccccc5)cc4)c4ccccc34)cc21]

TABLE 1-continued
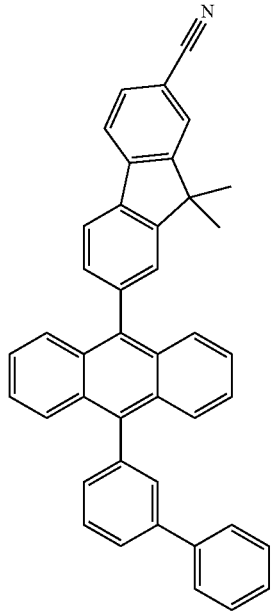 [SMILES: CC1(C)c2cc(C#N)ccc2-c2ccc(-c3c4ccccc4c(-c4cccc(-c5ccccc5)c4)c4ccccc34)cc21]
[Formula 1-8]
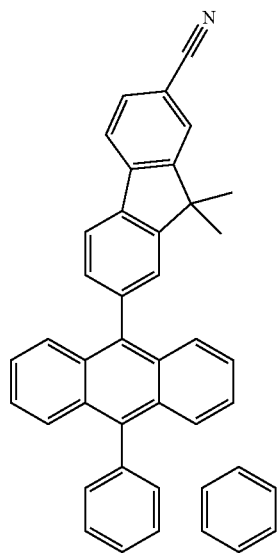
[Formula 1-9]

TABLE 1-continued
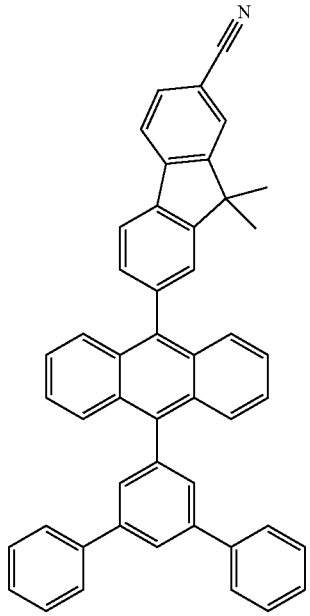 [SMILES: CC1(C)c2cc(C#N)ccc2-c2ccc(-c3c4ccccc4c(-c4cc(-c5ccccc5)cc(-c5ccccc5)c4)c4ccccc34)cc21]
[Formula 1-10]
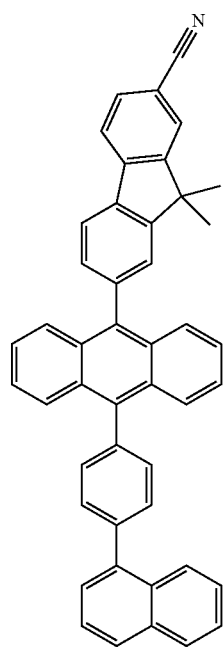 [SMILES: CC1(C)c2cc(C#N)ccc2-c2ccc(-c3c4ccccc4c(-c4ccc(-c5cccc6ccccc56)cc4)c4ccccc34)cc21]
[Formula 1-11]

TABLE 1-continued
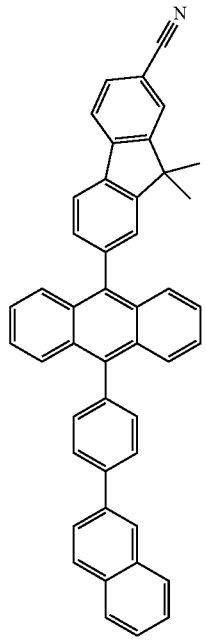 [SMILES: CC1(C)c2cc(C#N)ccc2-c2ccc(-c3c4ccccc4c(-c4ccc(-c5ccc6ccccc6c5)cc4)c4ccccc34)cc21]
[Formula 1-12]
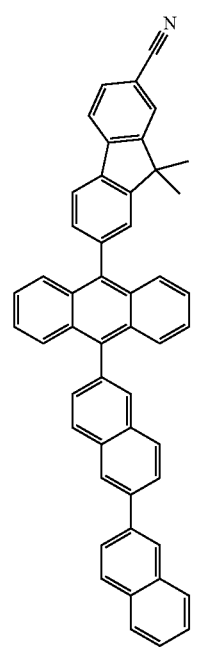 [SMILES: CC1(C)c2cc(C#N)ccc2-c2ccc(-c3c4ccccc4c(-c4ccc5cc(-c6ccc7ccccc7c6)ccc5c4)c4ccccc34)cc21]
[Formula 1-13]

TABLE 1-continued
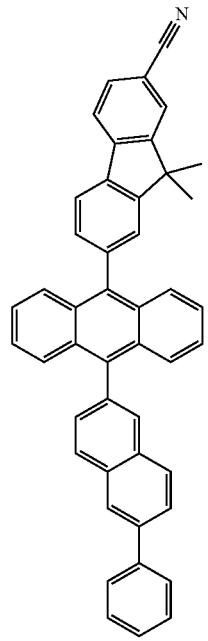 [SMILES: CC1(C)c2cc(C#N)ccc2-c2ccc(-c3c4ccccc4c(-c4ccc5cc(-c6ccccc6)ccc5c4)c4ccccc34)cc21]
[Formula 1-14]
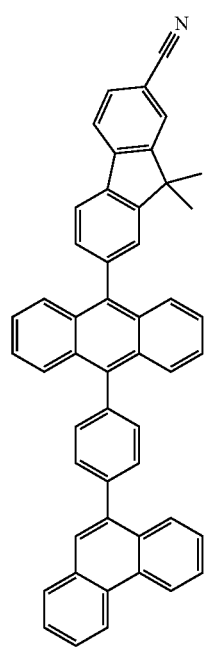 [SMILES: CC1(C)c2cc(C#N)ccc2-c2ccc(-c3c4ccccc4c(-c4ccc(-c5cc6ccccc6c6ccccc56)cc4)c4ccccc34)cc21]
[Formula 1-15]

TABLE 1-continued
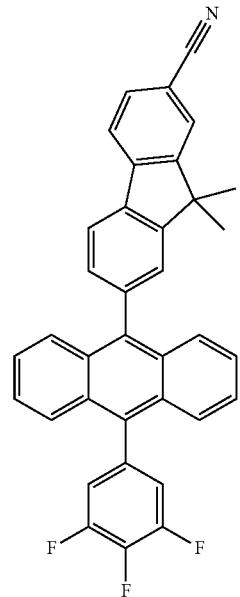 [SMILES: CC1(C)c2cc(C#N)ccc2-c2ccc(-c3c4ccccc4c(-c4cc(F)c(F)c(F)c4)c4ccccc34)cc21]
[Formula 1-16]
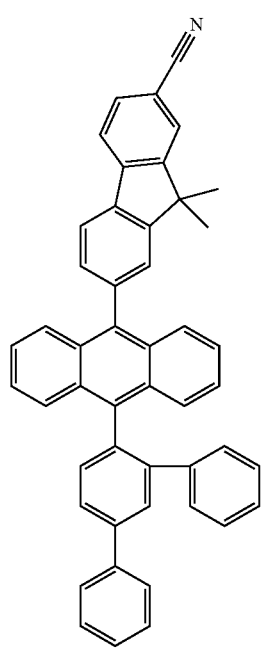 [SMILES: CC1(C)c2cc(C#N)ccc2-c2ccc(-c3c4ccccc4c(-c4ccc(-c5ccccc5)cc4-c4ccccc4)c4ccccc34)cc21]
[Formula 1-17]

TABLE 1-continued
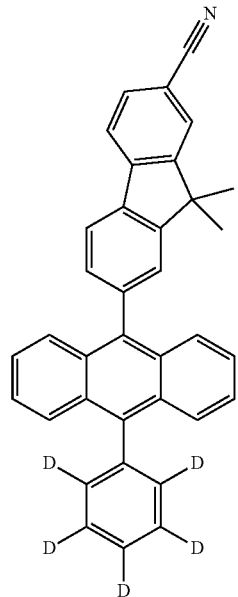 [SMILES: [2H]c1c([2H])c([2H])c(-c2c3ccccc3c(-c3ccc4c(c3)C(C)(C)c3cc(C#N)ccc3-4)c3ccccc23)c([2H])c1[2H]]
[Formula 1-18]
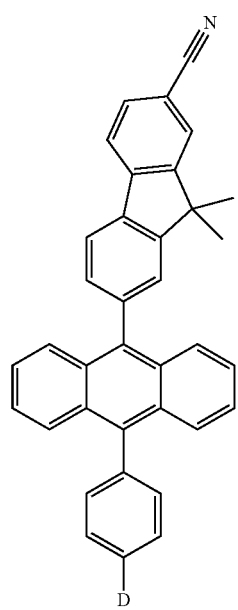 [SMILES: [2H]c1ccc(-c2c3ccccc3c(-c3ccc4c(c3)C(C)(C)c3cc(C#N)ccc3-4)c3ccccc23)cc1]
[Formula 1-19]

TABLE 1-continued
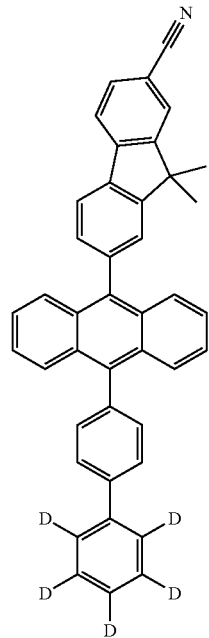 [SMILES: [2H]c1c([2H])c([2H])c(-c2ccc(-c3c4ccccc4c(-c4ccc5c(c4)C(C)(C)c4cc(C#N)ccc4-5)c4ccccc34)cc2)c([2H])c1[2H]]
[Formula 1-20]
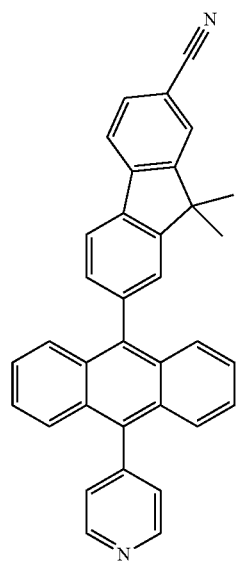 [SMILES: CC1(C)c2cc(C#N)ccc2-c2ccc(-c3c4ccccc4c(-c4ccncc4)c4ccccc34)cc21]
[Formula 1-21]

TABLE 1-continued
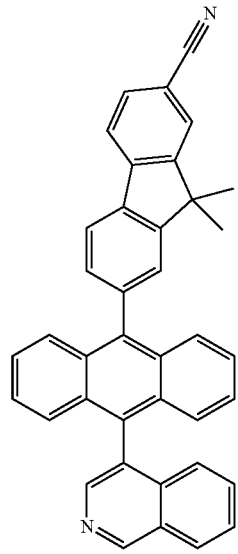 [SMILES: CC1(C)c2cc(C#N)ccc2-c2ccc(-c3c4ccccc4c(-c4cncc5ccccc45)c4ccccc34)cc21]
[Formula 1-22]
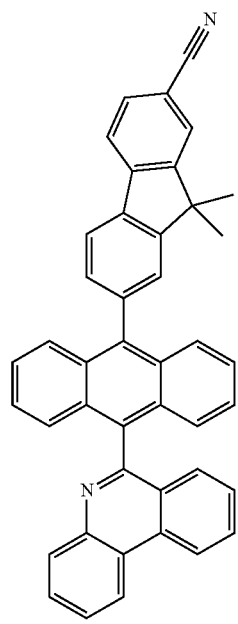 [SMILES: CC1(C)c2cc(C#N)ccc2-c2ccc(-c3c4ccccc4c(-c4nc5ccccc5c5ccccc45)c4ccccc34)cc21]
[Formula 1-23]

TABLE 1-continued
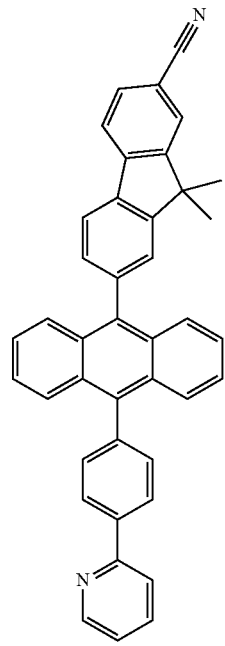 [SMILES: CC1(C)c2cc(C#N)ccc2-c2ccc(-c3c4ccccc4c(-c4ccc(-c5ccccn5)cc4)c4ccccc34)cc21]
[Formula 1-24]
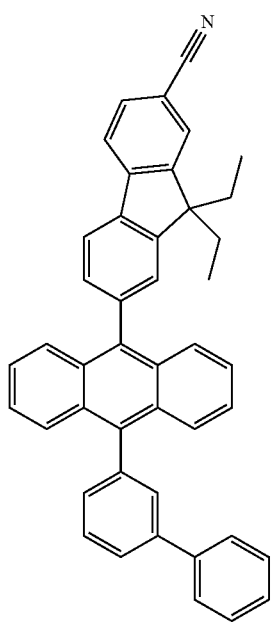 [SMILES: CCC1(CC)c2cc(C#N)ccc2-c2ccc(-c3c4ccccc4c(-c4cccc(-c5ccccc5)c4)c4ccccc34)cc21]
[Formula 1-25]

TABLE 1-continued
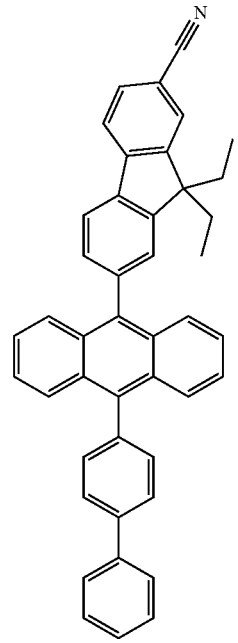 [SMILES: CCC1(CC)c2cc(C#N)ccc2-c2ccc(-c3c4ccccc4c(-c4ccc(-c5ccccc5)cc4)c4ccccc34)cc21]
[Formula 1-26]
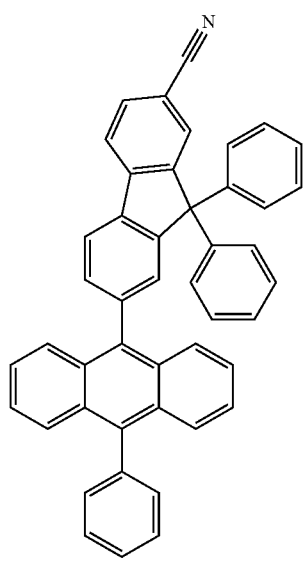 [SMILES: N#Cc1ccc2c(c1)C(c1ccccc1)(c1ccccc1)c1cc(-c3c4ccccc4c(-c4ccccc4)c4ccccc34)ccc1-2]
[Formula 1-27]

TABLE 1-continued
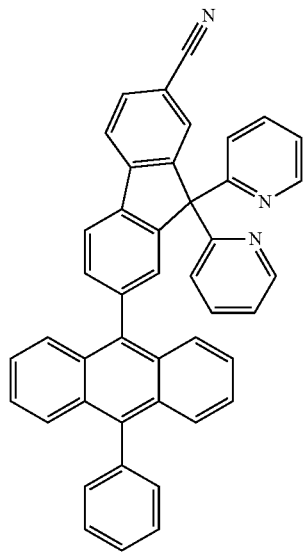 [SMILES: N#Cc1ccc2c(c1)C(c1ccccn1)(c1ccccn1)c1cc(-c3c4ccccc4c(-c4ccccc4)c4ccccc34)ccc1-2]
[Formula 1-28]
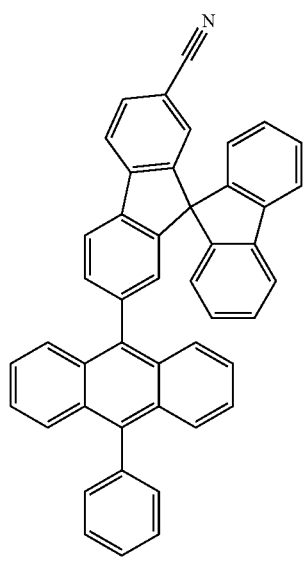 [SMILES: N#Cc1ccc2c(c1)C1(c3ccccc3-c3ccccc31)c1cc(-c3c4ccccc4c(-c4ccccc4)c4ccccc34)ccc1-2]
[Formula 1-29]
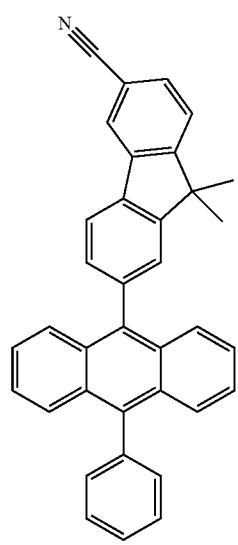 [SMILES: CC1(C)c2ccc(C#N)cc2-c2ccc(-c3c4ccccc4c(-c4ccccc4)c4ccccc34)cc21]
[Formula 1-30]

TABLE 1-continued
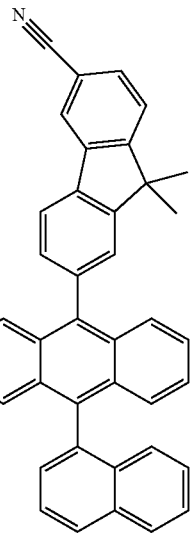
[Formula 1-31]
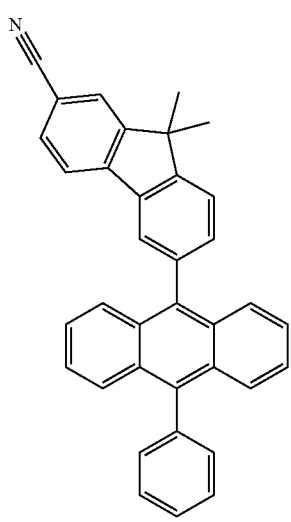 [SMILES: CC1(C)c2ccc(-c3c4ccccc4c(-c4ccccc4)c4ccccc34)cc2-c2ccc(C#N)cc21]
[Formula 1-32]

TABLE 1-continued
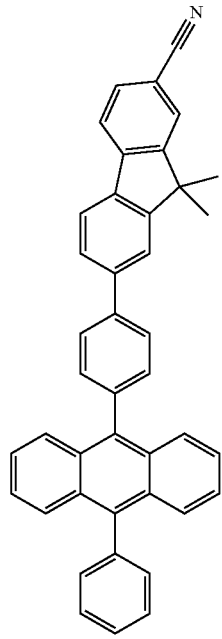
[Formula 1-33]
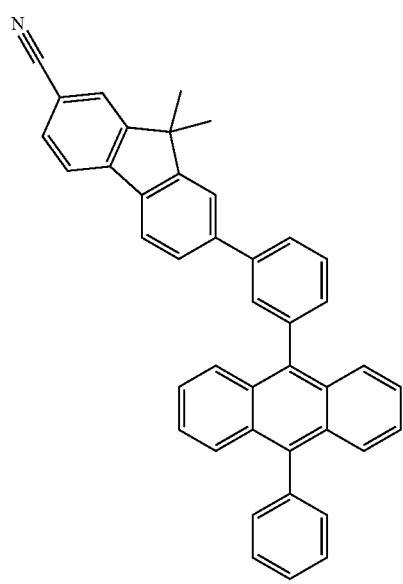 [SMILES: CC1(C)c2cc(C#N)ccc2-c2ccc(-c3cccc(-c4c5ccccc5c(-c5ccccc5)c5ccccc45)c3)cc21]
[Formula 1-34]

TABLE 1-continued
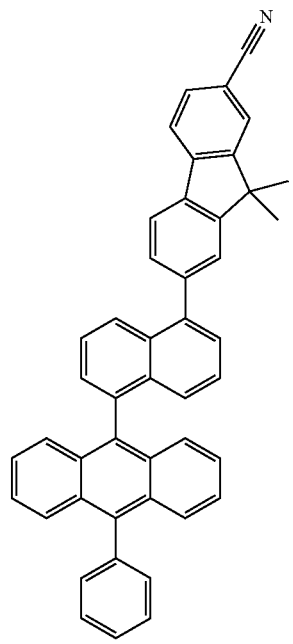 [SMILES: CC1(C)c2cc(C#N)ccc2-c2ccc(-c3cccc4c(-c5c6ccccc6c(-c6ccccc6)c6ccccc56)cccc34)cc21]
[Formula 1-35]
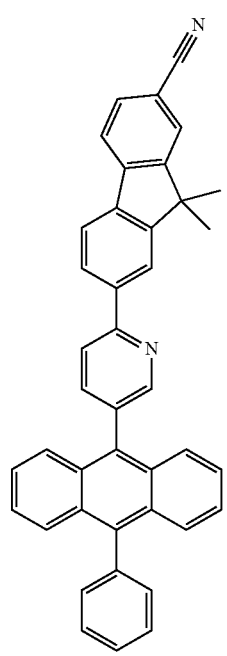 [SMILES: CC1(C)c2cc(C#N)ccc2-c2ccc(-c3ccc(-c4c5ccccc5c(-c5ccccc5)c5ccccc45)cn3)cc21]
[Formula 1-36]

TABLE 1-continued
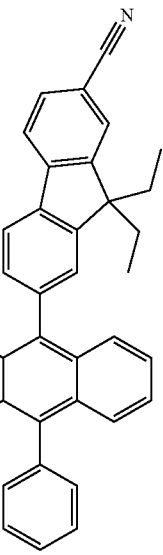
[Formula 1-37]
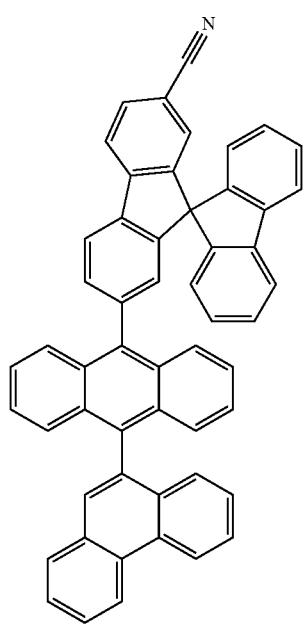 [SMILES: N#Cc1ccc2c(c1)C1(c3ccccc3-c3ccccc31)c1cc(-c3c4ccccc4c(-c4cc5ccccc5c5ccccc45)c4ccccc34)ccc1-2]
[Formula 1-38]

TABLE 1-continued
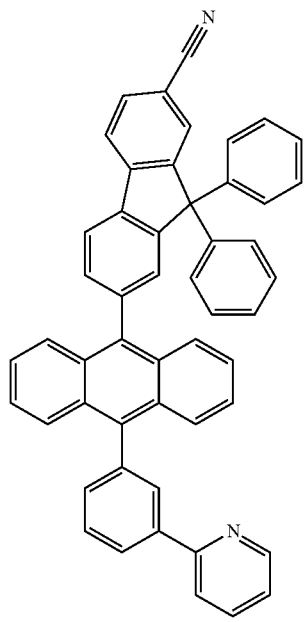 [SMILES: N#Cc1ccc2c(c1)C(c1ccccc1)(c1ccccc1)c1cc(-c3c4ccccc4c(-c4cccc(-c5ccccn5)c4)c4ccccc34)ccc1-2]
[Formula 1-39]
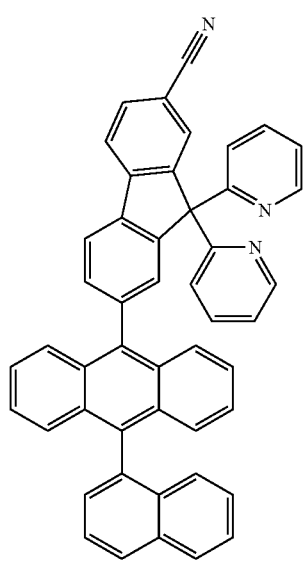 [SMILES: N#Cc1ccc2c(c1)C(c1ccccn1)(c1ccccn1)c1cc(-c3c4ccccc4c(-c4cccc5ccccc45)c4ccccc34)ccc1-2]
[Formula 1-40]
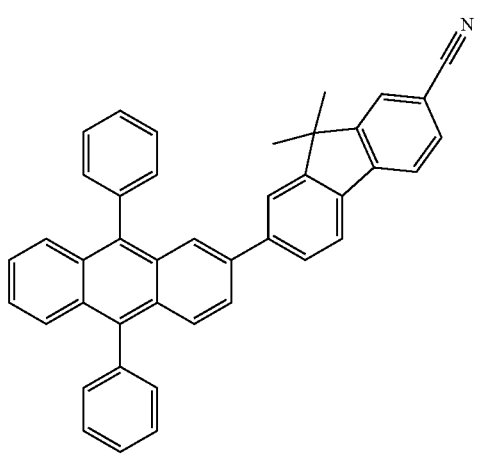 [SMILES: CC1(C)c2cc(C#N)ccc2-c2ccc(-c3ccc4c(-c5ccccc5)c5ccccc5c(-c5ccccc5)c4c3)cc21]
[Formula 2-1]

TABLE 1-continued
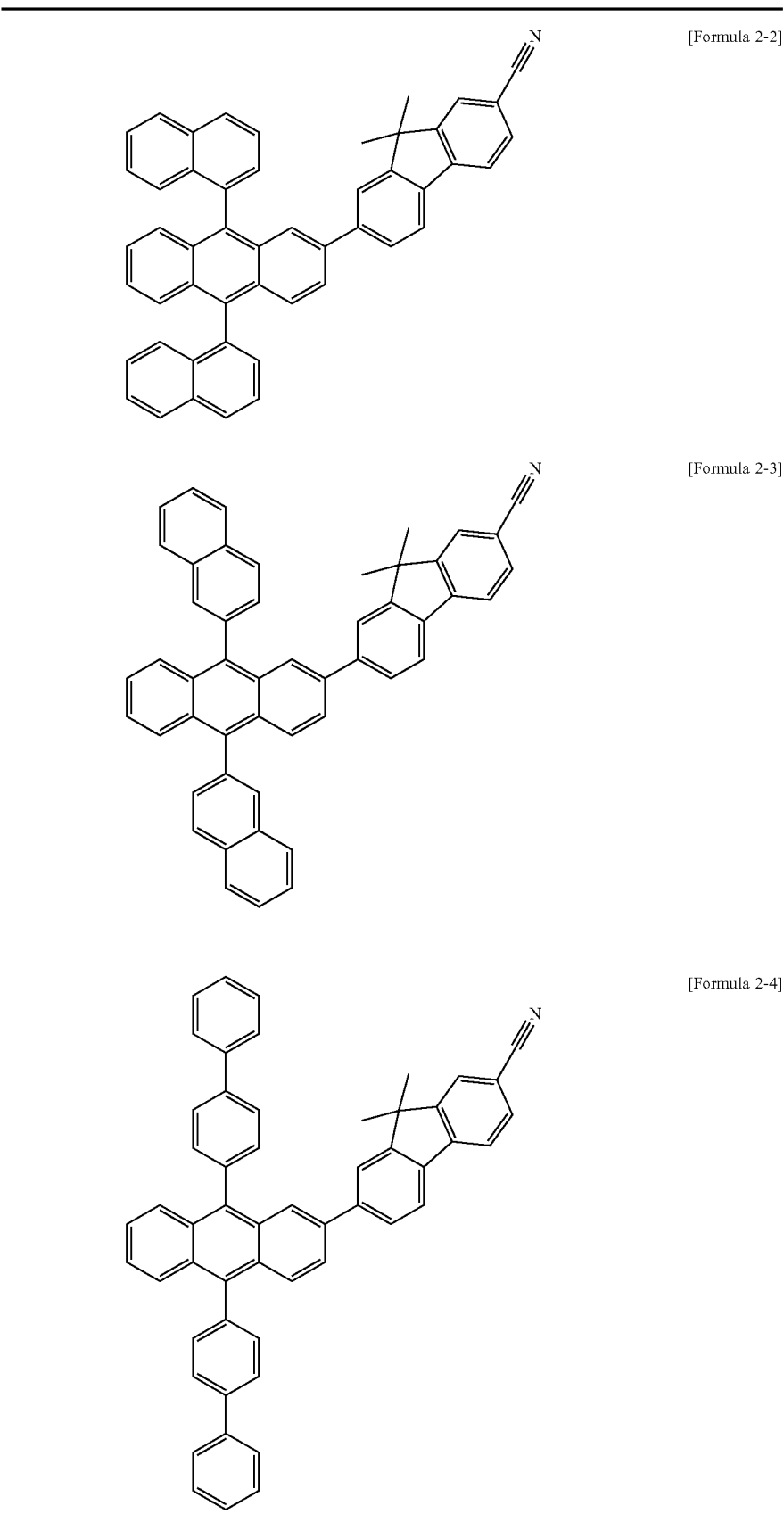
[Formula 2-2]
[Formula 2-3]
[Formula 2-4]

TABLE 1-continued
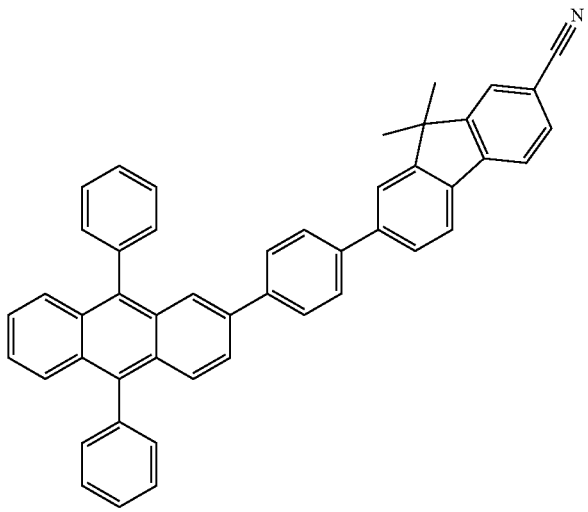 [SMILES: CC1(C)c2cc(C#N)ccc2-c2ccc(-c3ccc(-c4ccc5c(-c6ccccc6)c6ccccc6c(-c6ccccc6)c5c4)cc3)cc21]
[Formula 2-5]
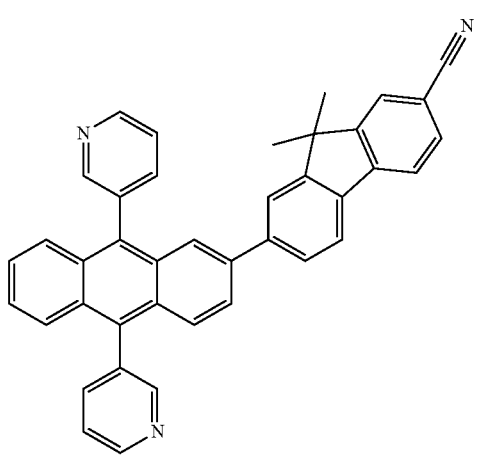 [SMILES: CC1(C)c2cc(C#N)ccc2-c2ccc(-c3ccc4c(-c5cccnc5)c5ccccc5c(-c5cccnc5)c4c3)cc21]
[Formula 2-6]
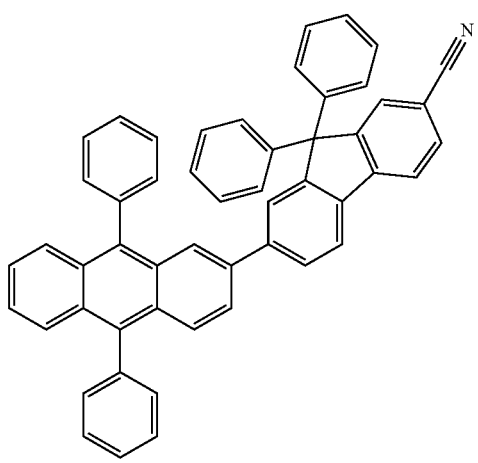 [SMILES: N#Cc1ccc2c(c1)C(c1ccccc1)(c1ccccc1)c1cc(-c3ccc4c(-c5ccccc5)c5ccccc5c(-c5ccccc5)c4c3)ccc1-2]
[Formula 2-7]

TABLE 1-continued
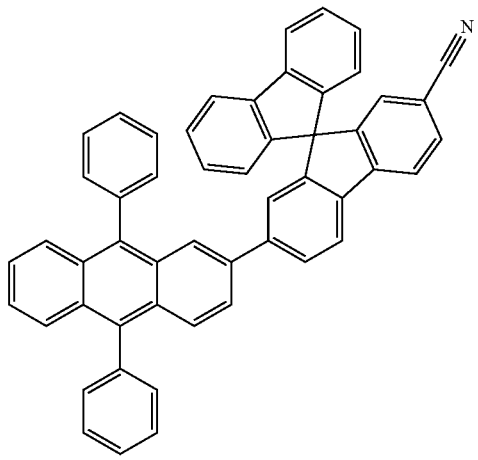 [SMILES: N#Cc1ccc2c(c1)C1(c3ccccc3-c3ccccc31)c1cc(-c3ccc4c(-c5ccccc5)c5ccccc5c(-c5ccccc5)c4c3)ccc1-2]
[Formula 2-8]
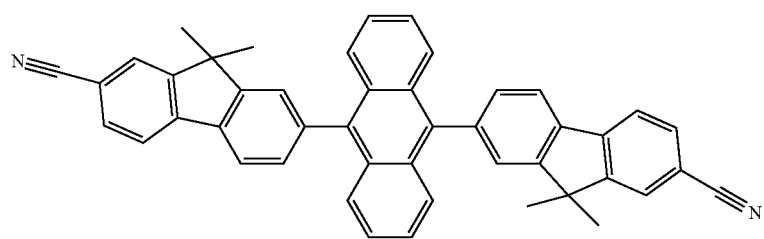 [SMILES: CC1(C)c2cc(C#N)ccc2-c2ccc(-c3c4ccccc4c(-c4ccc5c(c4)C(C)(C)c4cc(C#N)ccc4-5)c4ccccc34)cc21]
[Formula 3-1]
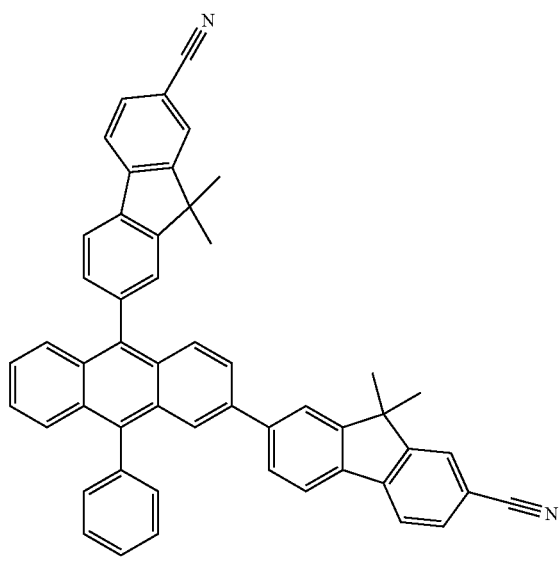 [SMILES: CC1(C)c2cc(C#N)ccc2-c2ccc(-c3ccc4c(-c5ccc6c(c5)C(C)(C)c5cc(C#N)ccc5-6)c5ccccc5c(-c5ccccc5)c4c3)cc21]
[Formula 3-2]

TABLE 1-continued
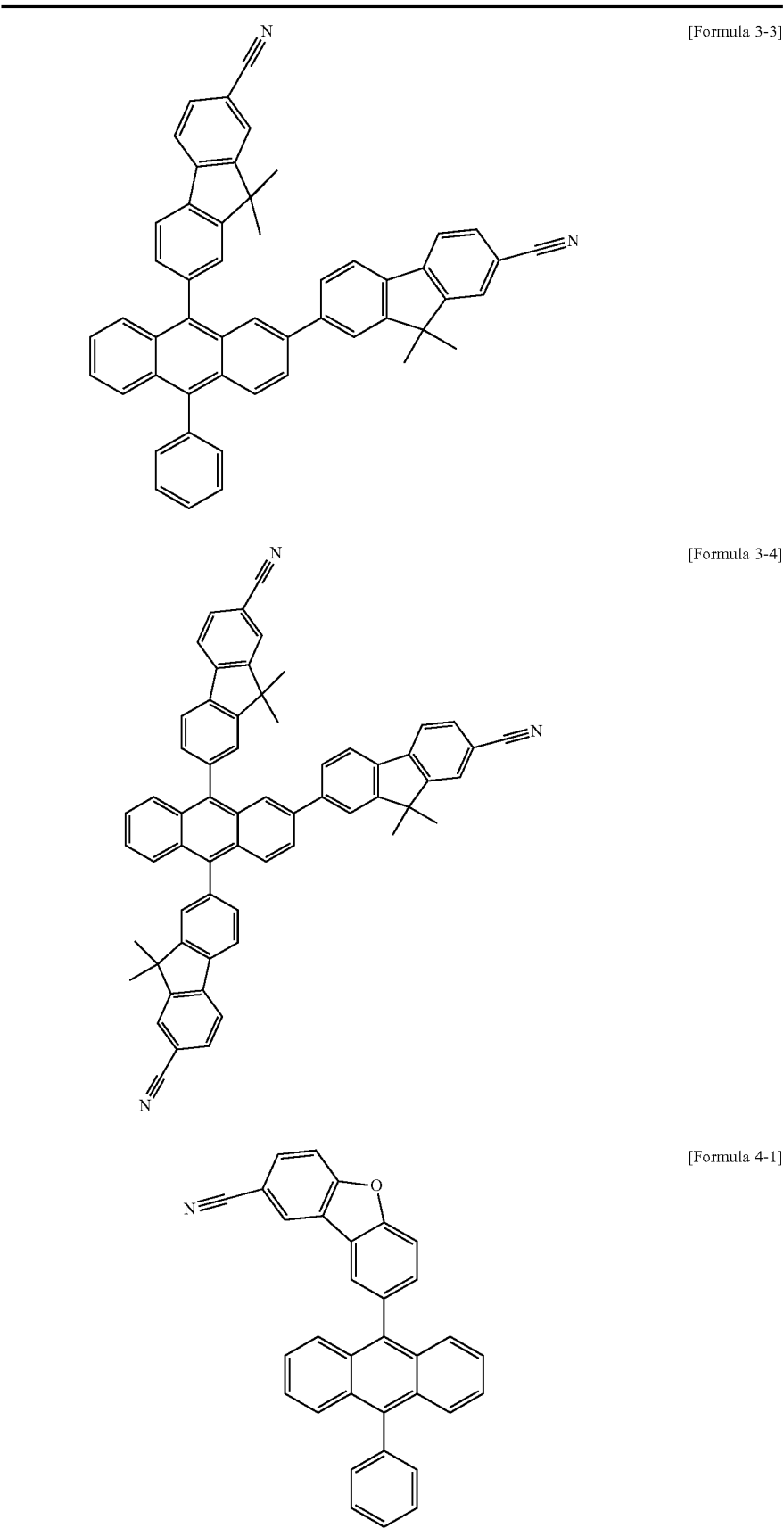
[Formula 3-3]
[Formula 3-4]
[Formula 4-1]

TABLE 1-continued

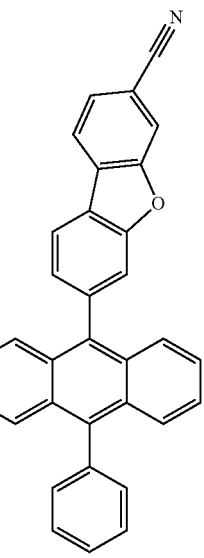

[Formula 4-2]

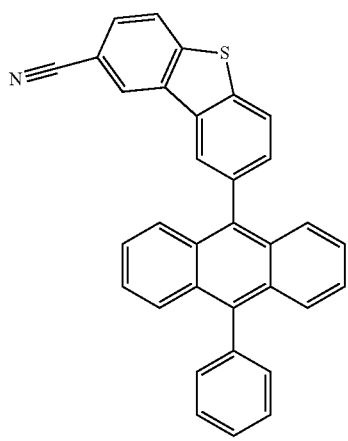 [SMILES: N#Cc1ccc2oc3ccc(-c4c5ccccc5c(-c5ccccc5)c5ccccc45)cc3c2c1]

[Formula 4-3]

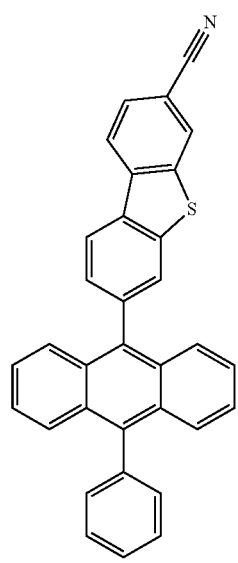 [SMILES: N#Cc1ccc2c(c1)oc1cc(-c3c4ccccc4c(-c4ccccc4)c4ccccc34)ccc12]

[Formula 4-4]

Another exemplary embodiment of the present application provides an organic electronic device including a first electrode, a second electrode, and an organic material layer having one or more layers disposed between the first electrode and the second electrode, in which one or more layers of the organic material layer include the compound.

In an exemplary embodiment of the present application, the organic electronic device may be composed of a structure including a first electrode, a second electrode, and an organic material layer disposed therebetween, and may be manufactured by using a typical manufacturing method and a material for an organic electronic device, except that the compound of Formula 1 is used for the organic material layer of the organic electronic device.

In an exemplary embodiment of the present application, the organic electronic device may be selected from the group consisting of an organic light emitting device, an organic solar cell, an organic photoconductor (OPC) drum, and an organic transistor, and more specifically, may be an organic light emitting device.

All of the devices require a hole injection or transporting material, an electron injection or transporting material, or a light emitting material in order to drive a device. In the organic electronic devices, the hole injection or transporting material, the electron injection or transporting material, or the light emitting material are operated on the basis of a similar principle.

In the organic electronic device according to an exemplary embodiment of the present application, the organic material layer of the organic electronic device includes a charge generating layer, and the charge generating layer may include the compound of Formula 1. The charge generating layer may additionally include a metal or a metal complex compound. Examples of the metal are the same as those described above. When the organic material layer includes two or more light emitting units, the charge generating layer may be provided between the light emitting units. The light emitting unit includes a light emitting layer having at least one layer, and may further include an additional organic material layer such as a charge transporting layer, if necessary. Furthermore, the charge generating layer may also be provided between a light emitting layer and any one electrode. Specifically, the charge generating layer may be provided between an anode and a light emitting layer. The charge generating layer may sequentially include an n-type organic material layer such as hexaazatriphenylene and a p-type organic material layer such as NPB on a surface close to a cathode. Specifically, a p-type organic material layer, an n-type organic material layer, and a charge generating layer may be sequentially stacked from the cathode side and provided. In another exemplary embodiment, the organic material layer of the organic electronic device may include a hole injection layer or a hole transporting layer including a compound that includes an aryl amino group, a carbazole group, or a benzcarbazole group, in addition to the organic material layer including a nitrogen-containing heterocyclic compound.

Hereinafter, an organic light emitting device will be exemplified.

An organic light emitting phenomenon refers to a phenomenon that converts electric energy into light energy by using an organic material. The organic light emitting device using the organic light emitting phenomenon has a structure which typically includes an anode, a cathode, and an organic material layer that is disposed therebetween.

In an exemplary embodiment of the present application, the organic material layer of the organic light emitting device may be composed of a mono-layer structure, but may be composed of a multi-layer structure in which two or more organic material layers are stacked. For example, the organic light emitting device may have a structure including a hole injection layer, a hole transporting layer, a light emitting layer, an electron transporting layer, an electron injection layer, a charge generating layer, a layer which transports and injects electrons simultaneously, and the like as an organic material layer. However, the structure of the organic light emitting device is not limited thereto, and may include a fewer number of organic material layers.

In the structure of the organic light emitting device, if a voltage is applied between two electrodes, holes are injected from an anode into the organic material layer and electrons are injected from a cathode into the organic material layer, and when the injected holes and the electrons meet each other, an exciton is formed, and light is emitted when the exciton falls to a bottom state. This organic light emitting device has properties such as self light emission, high brightness, high efficiency, low driving voltage, a wide viewing angle, high contrast, and high speed response. In the organic light emitting device, the material that is used as the organic material layer may be classified into a light emitting material and an electric charge transporting material, for example, a hole injection material, a hole transporting material, an electron transporting material, an electron injection material and the like, according to a function thereof. Further, the light emitting material may be classified into blue, green, and red light emitting materials and yellow and orange light emitting materials required for implementing better natural colors, according to the emission color. Meanwhile, when only one material is used as a light emitting material, by interaction between molecules, there are problems in that the maximum light emitting wavelength moves to the long wavelength, color purity is lowered, or efficiency of the device is lowered due to a reduced effect of light emission, and thus in order to increase color purity and increase light emission efficiency through an energy transfer, a host/dopant system may be used as the light emitting material.

In the organic light emitting device according to an exemplary embodiment of the present application, the organic material layer may include one or more layers of a hole injection layer, a hole transporting layer, and a layer which injects and transports holes simultaneously, and one or more layers of the layers may include the compound represented by Formula 1.

In addition, in the organic light emitting device according to an exemplary embodiment of the present application, the organic material layer may include one or more layers of a light emitting layer, an electron transporting layer, an electron injection layer, and a layer which transports and injects electrons simultaneously, and one or more layers of the layers may include the compound represented by Formula 1. Here, the layer including the compound represented by Formula 1 may additionally include an alkali metal, an alkali metal compound, an alkaline earth metal or an alkaline earth metal compound, or a combination thereof, which is an n-type dopant. In an exemplary embodiment of the present application, the n-type dopant applied to the organic electronic device is not particularly limited, but is preferably selected from Li, Na, K, Rb, Cs, Mg, Ca, Sr, Ba, La, Nd, Sm, Eu, Tb, Yb, LiF, Li$_2$O, CsF, or the following compounds.

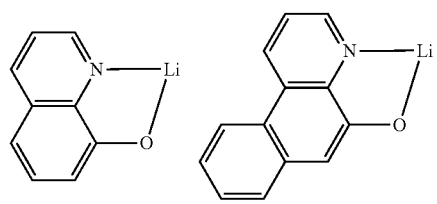

-continued

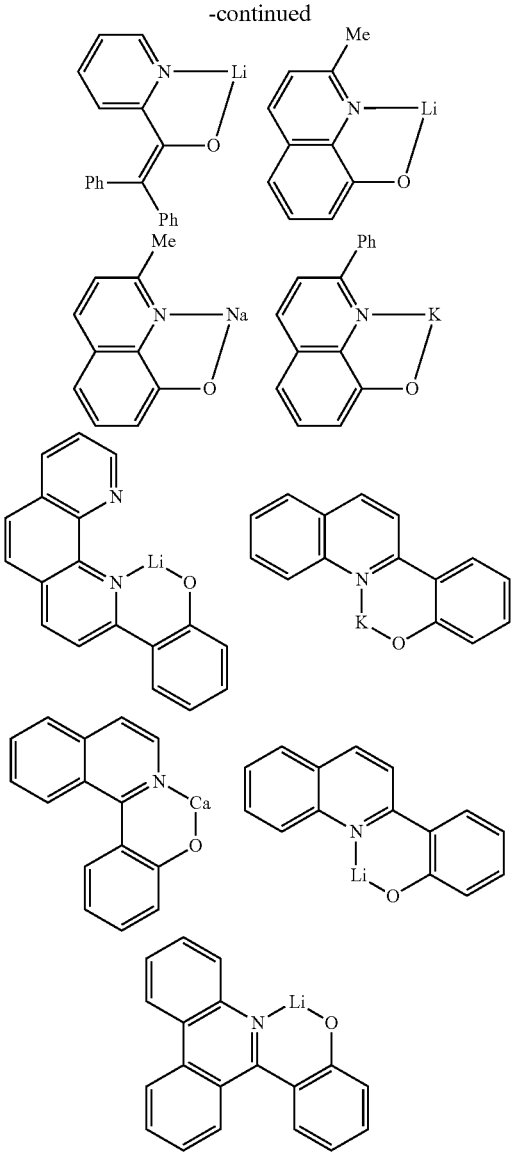

When an electron transporting layer, an electron injection layer, a layer which transports and injects electrons simultaneously, and the like are formed using the n-type dopant and the compound represented by Formula 1, electron injection characteristics are improved, and thus it is possible to obtain effects such as an increase in efficiency, a drop in driving voltage, and an increase in stability of the device. It is preferred that the n-type dopant is present in an amount from 1% by weight to 70% by weight based on the total weight of the composition of the layer including the compound.

In the organic material layer having the multi-layer structure, the compound represented by Formula 1 may be included in a light emitting layer, a layer which injects/transports holes and emits light simultaneously, a layer which transports holes and emits light simultaneously, or a layer which transports electrons and emits light simultaneously, and the like.

The light emitting layer of the organic light emitting device according to an exemplary embodiment of the present application may emit green, red, or blue light. At this time, in the organic light emitting device, one or more layers of the electron transporting layer and the layer which transports and injects electrons simultaneously may include the compound represented by Formula 1.

For example, the structure of the organic light emitting device according to an exemplary embodiment of the present application is illustrated in FIGS. 1 to 5.

FIG. 1 illustrates a structure of an organic electronic device in which an anode 2, a hole injection layer 3, a hole transporting layer 4, a light emitting layer 5, an electron transporting layer 6, and a cathode 7 are sequentially stacked on a substrate 1. In the structure, the compound represented by Formula 1 may be included in the hole injection layer 3, the hole transporting layer 4, the light emitting layer 5, or the electron transporting layer 6.

FIG. 2 illustrates a structure of an organic electronic device in which an anode 2, a hole injection layer 3, a hole transporting layer 4, a light emitting layer 5, and a cathode 7 are sequentially stacked on a substrate 1. In the structure, the compound represented by Formula 1 may be included in the hole injection layer 3, the hole transporting layer 4, or the electron transporting layer 6.

FIG. 3 illustrates a structure of an organic electronic device in which an anode 2, a hole transporting layer 4, a light emitting layer 5, an electron transporting layer 6, and a cathode 7 are sequentially stacked on a substrate 1. In the structure, the compound represented by Formula 1 may be included in the hole transporting layer 4, the light emitting layer 5, or the electron transporting layer 6.

FIG. 4 illustrates a structure of an organic electronic device in which an anode 2, a light emitting layer 5, an electron transporting layer 6, and a cathode 7 are sequentially stacked on a substrate 1. In the structure, the compound represented by Formula 1 may be included in the light emitting layer 5, or the electron transporting layer 6.

FIG. 5 illustrates a structure of an organic electronic device in which an anode 2, a light emitting layer 5, and a cathode 7 are sequentially stacked on a substrate 1. In the structure, the compound represented by Formula 1 may be included in the light emitting layer 5.

For example, the organic light emitting device according to an exemplary embodiment of the present application may be manufactured by depositing a metal or a metal oxide having conductivity, or an alloy thereof on a substrate to form an anode by using a physical vapor deposition (PVD) method such as sputtering or e-beam evaporation, forming an organic material layer including a hole injection layer, a hole transporting layer, a light emitting layer, and an electron transporting layer thereon, and then depositing a material, which may be used as a cathode, thereon.

In addition to the method of manufacturing an organic light emitting device having a forward direction structure, it is also possible to manufacture an organic light emitting device having a reverse direction structure by sequentially depositing a cathode material, an organic material layer, and an anode material on a substrate (International Publication No. 2003/012890). The organic material layer may be a multi-layer structure including a hole injection layer, a hole transporting layer, a light emitting layer, an electron transporting layer and the like, but may be a mono-layer structure without being limited thereto. In addition, the organic material layer may be manufactured to have a fewer number of layers by using various polymer materials by a solvent process other than a deposition method, such as, for example, spin coating, dip coating, doctor blading, screen printing, inkjet printing, a thermal transfer method or the like.

It is preferred that as the anode material, materials having a high work function are usually used so as to facilitate the injection of holes into the organic material layer. Specific examples of the anode material which may be used in the present application include: a metal such as vanadium, chromium, copper, zinc and gold, or an alloy thereof; a metal oxide such as zinc oxide, indium oxide, indium tin oxide (ITO) and indium zinc oxide (IZO); a combination of a metal and an oxide, such as ZnO:Al or $SnO_2$:Sb; a conductive polymer such as poly(3-methylthiophene), poly[3,4-(ethylene-1,2-dioxy)thiophene] (PEDT), polypyrrole and polyaniline; and the like, but are not limited thereto.

It is preferred that as the cathode material, materials having a low work function are usually used so as to facilitate the injection of electrons into the organic material layer. Specific examples of the cathode material include a metal such as magnesium, calcium, sodium, potassium, titanium, indium, yttrium, lithium, gadolinium, aluminum, silver, tin, and lead, or an alloy thereof; a multi-layer structured material such as LiF/Al or $LiO_2$/Al, and the like, but are not limited thereto.

The hole injection material is a material that may proficiently accept holes from the anode at low voltage, and the highest occupied molecular orbital (HOMO) of the hole injection material is preferably a value between the work function of the anode material and the HOMO of the neighboring organic material layer. Specific examples of the hole injection material include metal porphyrine, oligothiophene, arylamine-based organic materials, hexanitrile hexaazatriphenylene, quinacridone-based organic materials, perylene-based organic materials, anthraquinone, and polyaniline-based and polythiophene-based conductive polymers, and the like, but are not limited thereto.

The hole transporting material is suitably a material having high hole mobility which may accept holes from the anode or the hole injection layer and transfer the holes to the light emitting layer. Specific examples thereof include arylamine-based organic materials, conductive polymers, block copolymers having both conjugated portions and non-conjugated portions, and the like, but are not limited thereto.

The light emitting material is a material that may emit light in a visible light region by accepting and recombining holes from the hole transporting layer and electrons from the electron transporting layer, respectively, and preferably a material having high quantum efficiency for fluorescence and phosphorescence. Specific examples thereof include 8-hydroxy-quinoline-aluminum complex ($Alq_3$); carbazole-based compounds; dimerized styryl compounds; BAlq; 10-hydroxybenzoquinoline-metal compounds; benzoxazole-based, benzothiazole-based and benzimidazole-based compounds; poly(p-phenylenevinylene)(PPV)-based polymers; spiro compounds; and polyfluorene, rubrene, and the like, but are not limited thereto.

The electron transporting material is suitably a material having high electron mobility which may proficiently accept electrons from the cathode and transfer the electrons to the light emitting layer. Specific examples thereof include Al complexes of 8-hydroxyquinoline; complexes including $Alq_3$; organic radical compounds; hydroxyflavone-metal complexes, and the like, but are not limited thereto.

The organic light emitting device according to an exemplary embodiment of the present application may be a top emission type, a bottom emission type or a dual emission type according to the materials used.

The compound according to an exemplary embodiment of the present application may act even in organic electronic devices including organic solar cells, organic photoconductors, organic transistors, and the like, based on the principle similar to those applied to organic light emitting devices.

The organic solar cell may be composed of a structure including a first electrode, a second electrode, and an organic material layer disposed therebetween, and may include a hole transporting layer, a photoactive layer, and an electron transporting layer as organic material layers. The compound according to an exemplary embodiment of the present application may be used for an organic material layer of the organic solar cell, and more specifically, may be used for an electron transporting layer.

The organic photoconductor may include a conductive substrate, a charge transporting layer including an electron transporting material, and a charge producing layer. The compound according to an exemplary embodiment of the present application may be used for the charge transporting layer or the charge producing layer of the organic photoconductor.

The organic transistor may include a first electrode, a second electrode, a hole injection layer, an organic thin film layer, an electron injection layer, and the like. The compound according to an exemplary embodiment of the present application may be used for the hole injection layer or the electron transporting layer of the organic transistor, and more specifically, may be used for the electron transporting layer.

BEST MODE

Hereinafter, preferred Examples will be provided for better understanding of the present application. However, the following Examples are illustrative only, and the scope of the present application is not limited thereby.

EXAMPLES

<Preparation Example 1-1> Preparation of the Following Compound A-2

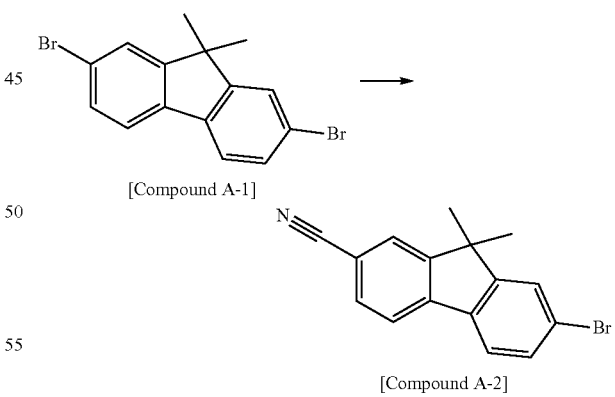

[Compound A-1]

[Compound A-2]

Compound A-1 (14.3 g, 40.6 mmol) and copper cyanide (CuCN) (3.64 g, 40.6 mmol) were dispersed in N,N-dimethylformamide (DMF) (100 mL), and the resulting mixture was stirred under reflux for 20 hours. The temperature was decreased to room temperature, the reaction mixture was slowly poured into an acidified aqueous $FeCl_3$ solution (a solution prepared by dissolving 50.0 g of $FeCl_3$ in 80 mL of water and 20 mL of concentrated hydrochloric acid), and the resulting mixture was stirred at 90° C. for 0.5 hour. The organic layer was separated, and the aqueous layer was extracted with chloroform (CHCl₃) (3×300 mL). The aqueous layer was removed, and the organic layer was collected and washed with 5N HCl (800 mL). The organic layer was washed with water (3×200 mL) and a 10% NaOH aqueous solution (500 mL), and then washed with water (3×200 mL). The aqueous layer was removed, and the organic layer was dried over anhydrous magnesium sulfate (MgSO₄) and then filtered. The filtrate was concentrated under reduced pressure and column purified with chloroform/hexane (1:1, v/v) to prepare Compound A-2 (4.72 g, 39%).
MS: [M+H]⁺=299

<Preparation Example 1-2> Preparation of the Following Compound A-4

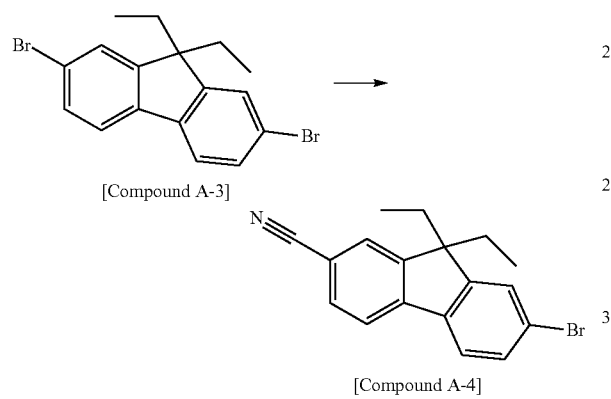

Compound A-4 (4.64 g, 35%) was prepared in the same manner as in Preparation Example 1-1, except that Compound A-3 (15.4 g, 40.6 mmol) was used instead of Compound A-1 in Preparation Example 1-1.
MS: [M+H]⁺=327

<Preparation Example 1-3> Preparation of the Following Compound A-6

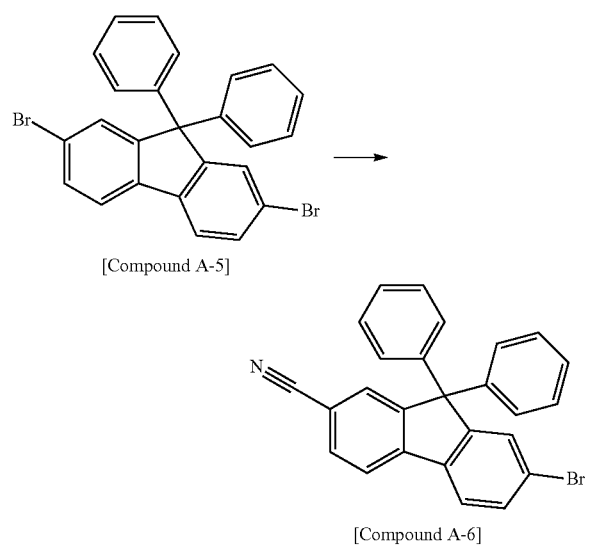

Compound A-6 (5.32 g, 31%) was prepared in the same manner as in Preparation Example 1-1, except that Compound A-5 (19.3 g, 40.6 mmol) was used instead of Compound A-1 in Preparation Example 1-1.
MS: [M+H]⁺=423

<Preparation Example 1-4> Preparation of the Following Compound A-8

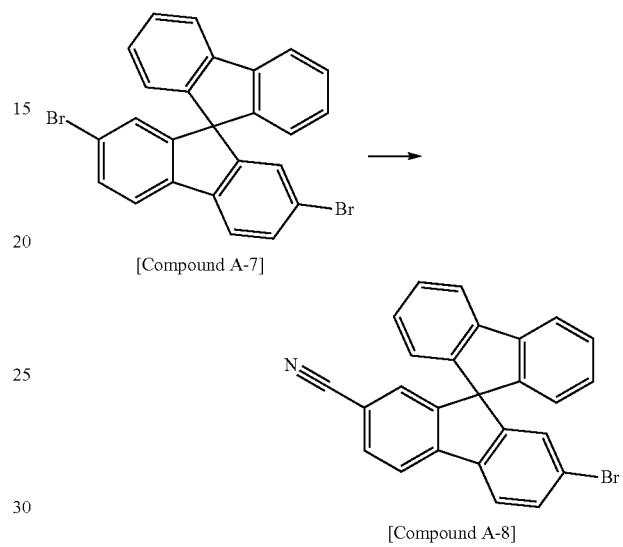

Compound A-8 (5.80 g, 34%) was prepared in the same manner as in Preparation Example 1-1, except that Compound A-7 (19.3 g, 40.6 mmol) was used instead of Compound A-1 in Preparation Example 1-1.
MS: [M+H]⁺=421

<Preparation Example 1-5> Preparation of the Following Compound A-10

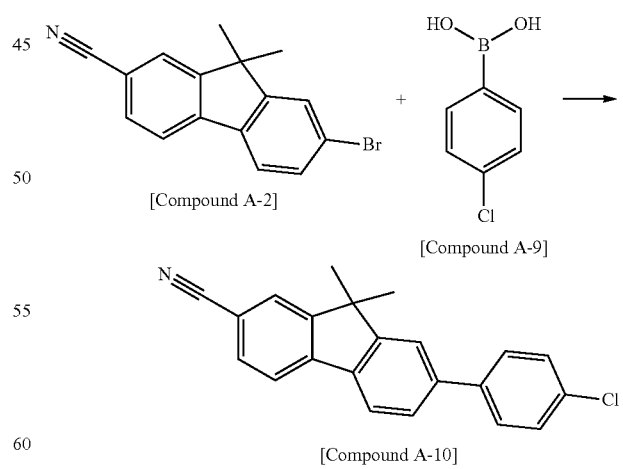

Compound A-2 (5.0 g, 16.8 mmol) and Compound A-9 (2.63 g, 16.8 mmol) were dispersed in tetrahydrofuran (100 mL), a 2 M potassium carbonate aqueous solution (aq. K₂CO₃) (34 mL) was added thereto, tetrakistriphenylphosphinopalladium [Pd(PPh₃)₄] (0.388 g, 2 mol %) was put thereinto, and then the resulting mixture was stirred under reflux for 5 hours. The temperature was decreased to normal temperature, and the organic layer was extracted and concentrated, and recrystallized with ethanol to prepare Compound A-10 (4.84 g, 89%).

MS: [M+H]$^+$=330

<Preparation Example 1-6> Preparation of the Following Compound A-12

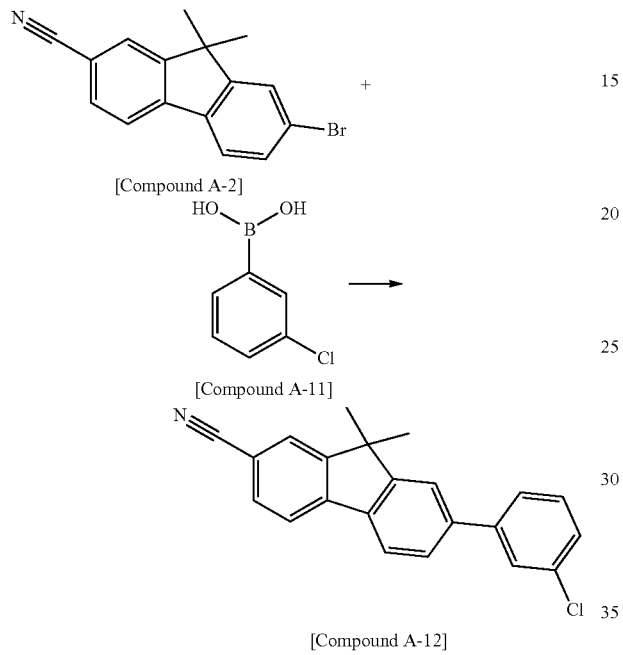

Compound A-12 (4.57 g, 84%) was prepared in the same manner as in Preparation Example 1-5, except that Compound A-11 (2.63 g, 16.8 mmol) was used instead of Compound A-9 in Preparation Example 1-5.

MS: [M+H]$^+$=330

<Preparation Example 1-7> Preparation of the Following Compound A-13

[Compound A-2]

[Compound A-13]

Compound A-2 (8.6 g, 29.0 mmol) and bis(pinacolato) diboron (7.36 g, 29.0 mmol) were dispersed in tetrahydrofuran (100 ml), potassium acetate (KOAC) (8.54 g, 87 mmol) and 1,1'-bisdiphenylphosphino ferrocene dichloropalladium (Pd(dppf)Cl$_2$.CH$_2$Cl$_2$) (0.71 g, 3 mol %) were put thereinto, and then the resulting mixture was stirred under reflux for 6 hours. The temperature was decreased to normal temperature, and the produced solid was filtered. The filtered solid was recrystallized with chloroform and ethanol and filtered, and then dried to prepare Compound A-13 (8.91 g, 89%)

MS: [M+H]$^+$=346

<Preparation Example 1-8> Preparation of the Following Compound A-15

[Compound A-14]

[Compound A-15]

Compound A-15 (4.64 g, 42%) was prepared in the same manner as in Preparation Example 1-1, except that Compound A-14 (13.2 g, 40.6 mmol) was used instead of Compound A-1 in Preparation Example 1-1.

MS: [M+H]$^+$=271

<Preparation Example 1-9> Preparation of the Following Compound A-17

[Compound A-16]

[Compound A-17]

Compound A-17 (5.52 g, 50%) was prepared in the same manner as in Preparation Example 1-1, except that Compound A-16 (13.2 g, 40.6 mmol) was used instead of Compound A-1 in Preparation Example 1-1.

MS: [M+H]$^+$=271

<Preparation Example 1-10> Preparation of the Following Compound A-19

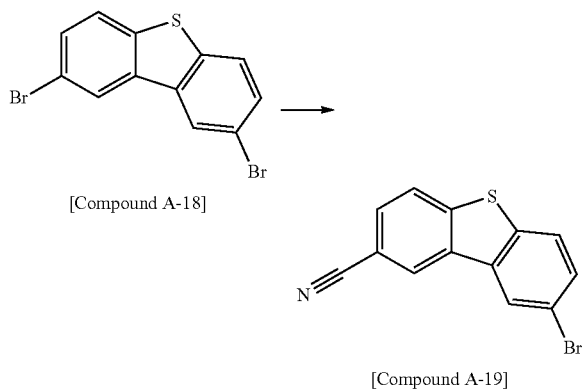

[Compound A-18]

[Compound A-19]

Compound A-19 (4.45 g, 38%) was prepared in the same manner as in Preparation Example 1-1, except that Compound A-18 (13.9 g, 40.6 mmol) was used instead of Compound A-1 in Preparation Example 1-1.

<Preparation Example 1-11> Preparation of the Following Compound A-21

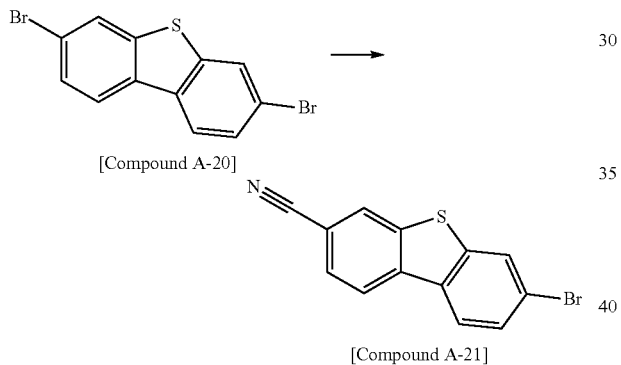

[Compound A-20]

[Compound A-21]

Compound A-21 (5.39 g, 46%) was prepared in the same manner as in Preparation Example 1-1, except that Compound A-20 (13.9 g, 40.6 mmol) was used instead of Compound A-1 in Preparation Example 1-1.

<Preparation Example 2-1> Preparation of the Following Compound B-2

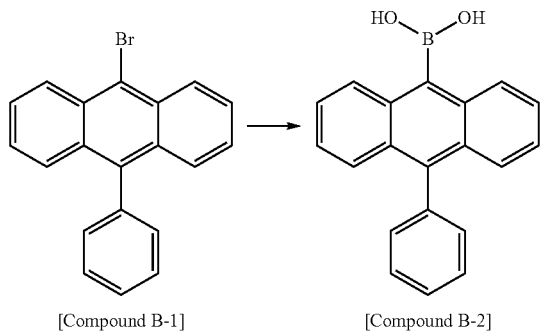 [SMILES: Brc1c2ccccc2c(-c2ccccc2)c2ccccc12 ; OB(O)c1c2ccccc2c(-c2ccccc2)c2ccccc12]

[Compound B-1]   [Compound B-2]

Compound B-1 (5.96 g, 17.9 mmol) was dissolved in tetrahydrofuran (100 mL), the temperature was decreased to −78° C., and then 1.7 M tertiary-butyllithium (t-BuLi) (10.6 mL, 17.9 mmol) was slowly added thereto. The resulting mixture was stirred at the same temperature for 1 hour, trimethyl borate (B(OCH$_3$)$_3$) (3.72 g, 35.8 mmol) was added thereto, and then the resulting mixture was stirred for 3 hours while slowly increasing the temperature to normal temperature. 2 N hydrochloric acid aqueous solution (30 mL) was added to the reaction mixture, and stirred at normal temperature for 1.5 hours. The produced precipitate was filtered and washed sequentially with water and ethyl ether, and then vacuum-dried. After drying, the precipitate was dispersed in ethyl ether, and the resulting mixture was stirred for 2 hours, filtered, and dried to prepare Compound B-2 (3.79 g, 71%).

MS: [M+H]$^+$=299

<Preparation Example 2-2> Preparation of the Following Compound B-4

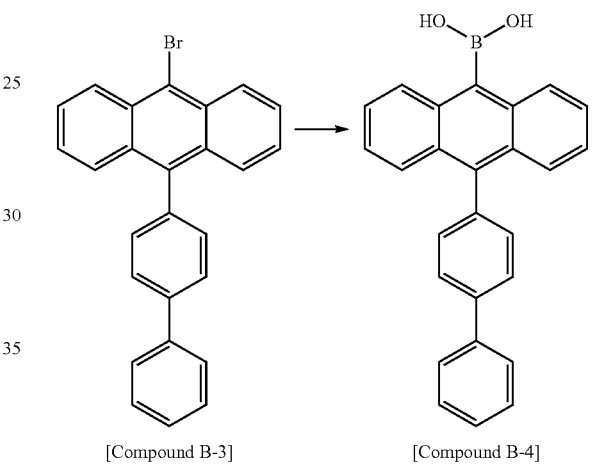

[Compound B-3]   [Compound B-4]

Compound B-4 (5.02 g, 75%) was prepared in the same manner as in Preparation Example 2-1, except that Compound B-3 (7.33 g, 17.9 mmol) was used instead of Compound B-1 in Preparation Example 2-1.

MS: [M+H]$^+$=375

<Preparation Example 2-3> Preparation of the Following Compound B-6

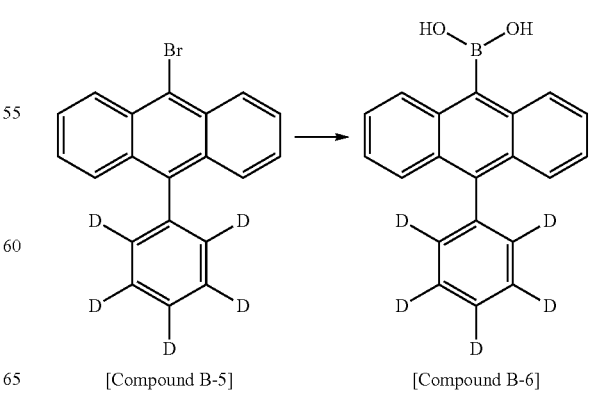

[Compound B-5]   [Compound B-6]

Compound B-6 (3.74 g, 69%) was prepared in the same manner as in Preparation Example 2-1, except that Compound B-5 (6.05 g, 17.9 mmol) was used instead of Compound B-1 in Preparation Example 2-1.

MS: [M+H]$^+$=304

<Preparation Example 2-4> Preparation of the Following Compound B-8

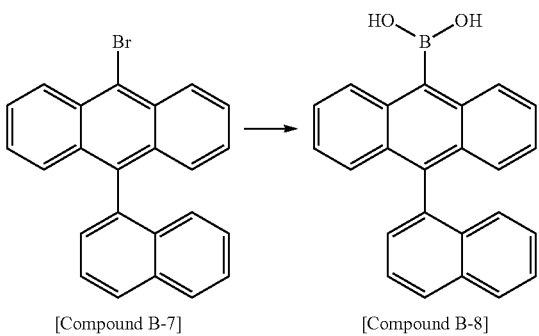 [SMILES: Brc1c2ccccc2c(-c2cccc3ccccc23)c2ccccc12 ; OB(O)c1c2ccccc2c(-c2cccc3ccccc23)c2ccccc12]

[Compound B-7]　　　[Compound B-8]

Compound B-8 (3.86 g, 62%) was prepared in the same manner as in Preparation Example 2-1, except that Compound B-7 (6.86 g, 17.9 mmol) was used instead of Compound B-1 in Preparation Example 2-1.

MS: [M+H]$^+$=349

<Preparation Example 2-5> Preparation of the Following Compound B-10

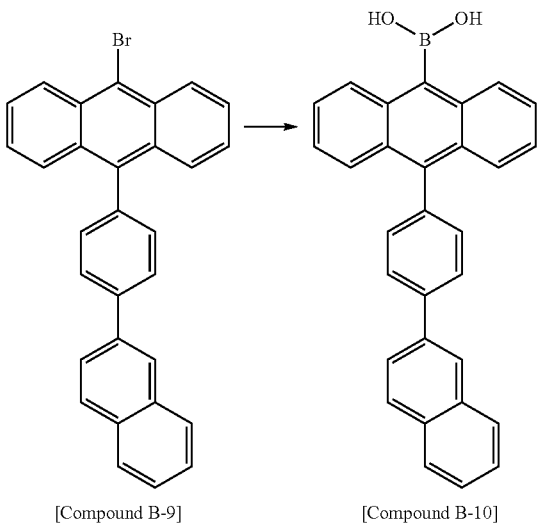 [SMILES: Brc1c2ccccc2c(-c2ccc(-c3ccc4ccccc4c3)cc2)c2ccccc12 ; OB(O)c1c2ccccc2c(-c2ccc(-c3ccc4ccccc4c3)cc2)c2ccccc12]

[Compound B-9]　　　[Compound B-10]

Compound B-10 (5.54 g, 73%) was prepared in the same manner as in Preparation Example 2-1, except that Compound B-9 (8.22 g, 17.9 mmol) was used instead of Compound B-1 in Preparation Example 2-1.

MS: [M+H]$^+$=425

<Preparation Example 2-6> Preparation of the Following Compound B-12

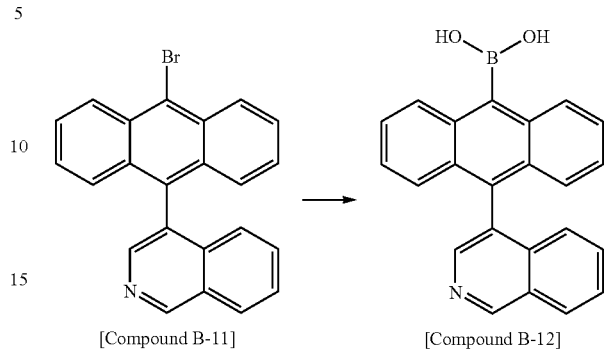

[Compound B-11]　　　[Compound B-12]

Compound B-12 (2.63 g, 42%) was prepared in the same manner as in Preparation Example 2-1, except that Compound B-11 (6.88 g, 17.9 mmol) was used instead of Compound B-1 in Preparation Example 2-1.

MS: [M+H]$^+$=350

<Preparation Example 2-7> Preparation of the Following Compound B-14

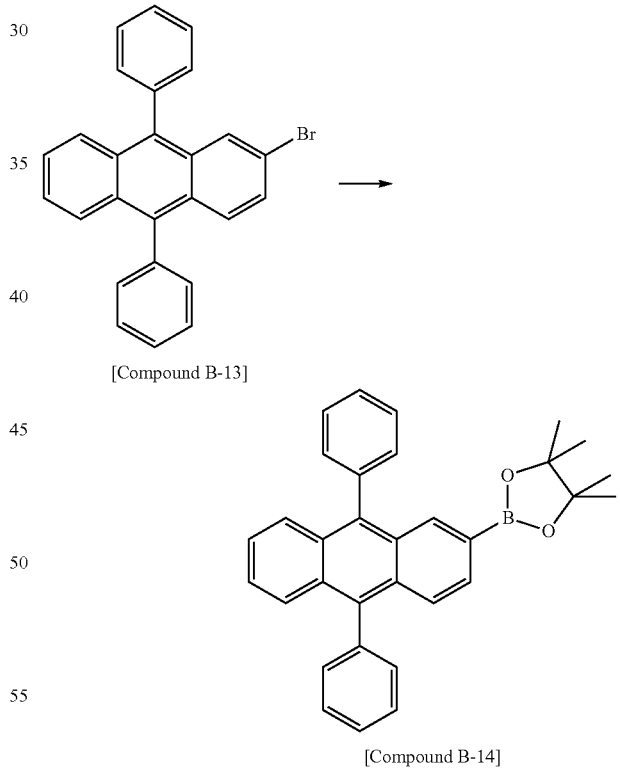

[Compound B-13]

[Compound B-14]

Compound B-13 (16.7 g, 40.8 mmol), bis(pinacolato) diboron (11.4 g, 44.9 mmol), and potassium acetate (KOAc) (12.0 g, 122 mmol) were suspended in 1,4-dioxane (250 mL). Pd(dba)$_2$ (0.70 g, 3 mol %) and PCy$_3$ (0.69 g, 6 mol %) were added to the suspension. The mixture was stirred under reflux for about 8 hours, and cooled to normal temperature. The mixture was diluted with water (250 mL) and extracted with chloroform (3×150 mL). The organic extract was dried over magnesium sulfate, and then filtered. The filtrate was concentrated under reduced pressure, and recrystallized with ethyl ether and hexane to prepare Compound B-14 (14.9 g, 80%).
MS: [M+H]⁺=457

<Preparation Example 2-8> Preparation of the Following Compound B-16

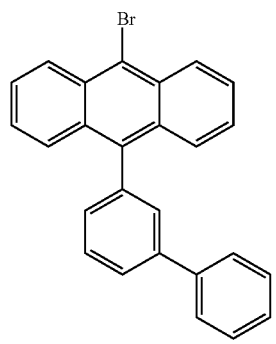

[Compound B-15]

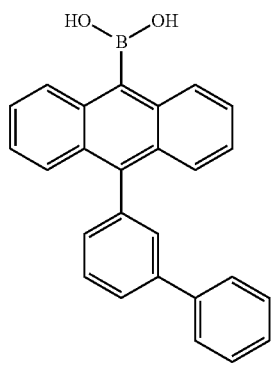

[Compound B-16]

Compound B-16 (4.62 g, 69%) was prepared in the same manner as in Preparation Example 2-1, except that Compound B-15 (7.33 g, 17.9 mmol) was used instead of Compound B-1 in Preparation Example 2-1.
MS: [M+H]⁺=375

<Preparation Example 2-9> Preparation of the Following Compound B-18

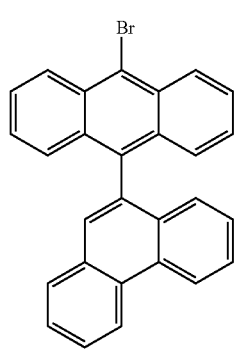

[Compound B-17]

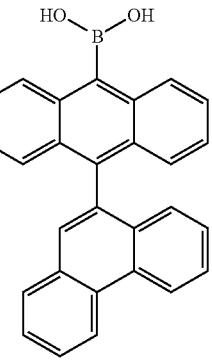

[Compound B-18]

Compound B-18 (4.21 g, 59%) was prepared in the same manner as in Preparation Example 2-1, except that Compound B-17 (7.76 g, 17.9 mmol) was used instead of Compound B-1 in Preparation Example 2-1.
MS: [M+H]⁺=399

<Preparation Example 2-10> Preparation of the Following Compound B-20

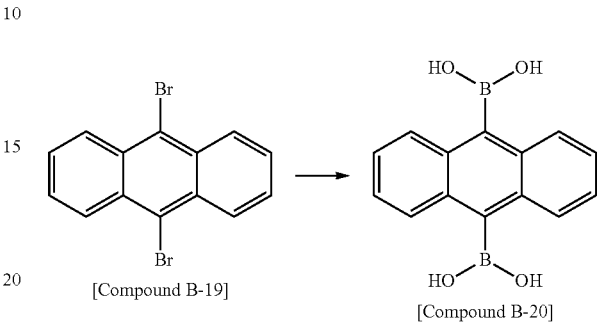

[Compound B-19]  [Compound B-20]

Compound B-20 (2.57 g, 54%) was prepared in the same manner as in Preparation Example 2-1, except that Compound B-19 (6.01 g, 17.9 mmol), 1.7 M tertiary butyllithium (t-BuLi) (21.2 mL, 35.8 mmol), and trimethyl borate (B(OCH₃)₃) (7.44 g, 71.6 mmol) were used instead of Compound B-1 in Preparation Example 2-1.
MS: [M+H]⁺=266

<Preparation Example 2-11> Preparation of the Following Compound B-23

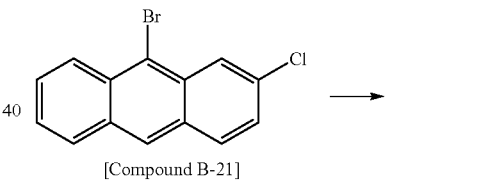

[Compound B-21]

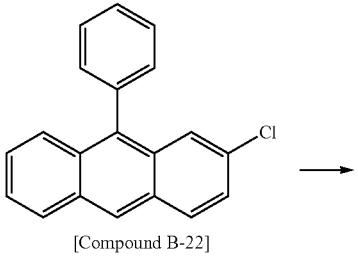

[Compound B-22]

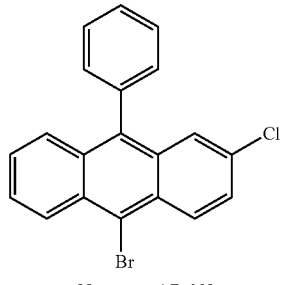

[Compound B-23]

Compound B-21 (10 g, 34.3 mmol) and phenylboronic acid (4.18 g, 34.3 mmol) were dispersed in tetrahydrofuran (100 mL), a 2 M potassium carbonate aqueous solution (aq. $K_2CO_3$) (70 mL) was added thereto, tetrakistriphenylphosphinopalladium [Pd(PPh$_3$)$_4$] (0.793 g, 2 mol %) was put thereinto, and then the resulting mixture was stirred under reflux for 5 hours. The temperature was decreased to normal temperature and the produced solid was filtered to prepare Compound B-22 (9.01 g, 91%). The thus-prepared B-22 (9.01 g, 31.2 mmol) was dissolved in methylene chloride (100 ml), N-Bromosuccineimide (6.11 g, 34.3 mmol) and hydrogen bromide (3 drops) were put thereinto, and then the resulting mixture was stirred for 1 hour. After the reaction was completed, the organic layer was washed with a sodium bisulfite (NaHSO$_3$) aqueous solution, and then a solid obtained under reduced pressure was recrystallized with chloroform and ethanol, filtered, and then dried to prepare Compound B-23 (8.14 g, 71%).

MS: [M+H]$^+$=368

<Preparation Example 2-12> Preparation of the Following Compound B-26

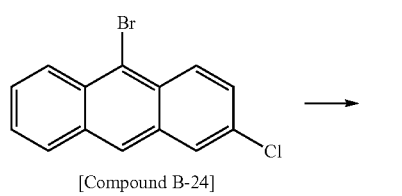

[Compound B-24]

[Compound B-25]

[Compound B-26]

Compound B-26 (7.26 g, 58%) was prepared in the same manner as in Preparation Example 2-1, except that Compound B-24 (10 g, 34.3 mmol) was used instead of Compound B-21 in Preparation Example 2-11.

MS: [M+H]$^+$=368

<Example 1> Preparation of Compound of Formula 1-1

[Compound A-2]

[Compound B-2]

[Compound 1-1]

Compound A-2 (5.96 g, 20.0 mmol) and Compound B-2 (5.96 g, 20.0 mmol) were dispersed in tetrahydrofuran (100 mL), a 2 M potassium carbonate aqueous solution (aq. $K_2CO_3$) (40 mL) was added thereto, tetrakistriphenylphosphinopalladium [Pd(PPh$_3$)$_4$] (0.462 g, 2 mol %) was put thereinto, and then the resulting mixture was stirred under reflux for 5 hours. The temperature was decreased to normal temperature, and the produced solid was filtered. The filtered solid was recrystallized with chloroform and ethanol and filtered, and then dried to prepare a compound of Formula 1-1 (6.13 g, 65%).

MS: [M+H]$^+$=472

<Example 2> Preparation of Compound of Formula 1-3

[Compound A-2]

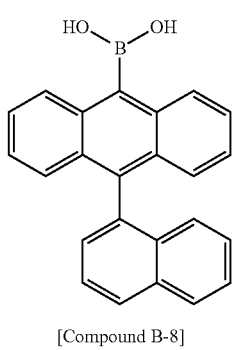

[Compound B-8]

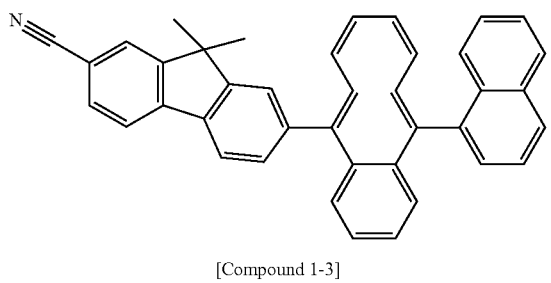

[Compound 1-3]

The compound of Formula 1-3 (6.47 g, 62%) was prepared in the same manner as in Example 1, except that Compound B-8 (6.96 g, 20.0 mmol) was used instead of Compound B-2 in Example 1.

MS: [M+H]$^+$=522

<Example 3> Preparation of Compound of Formula 1-7

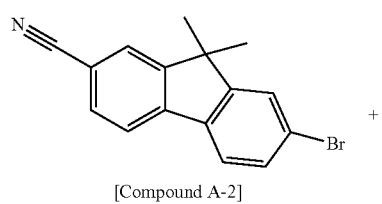

[Compound A-2]

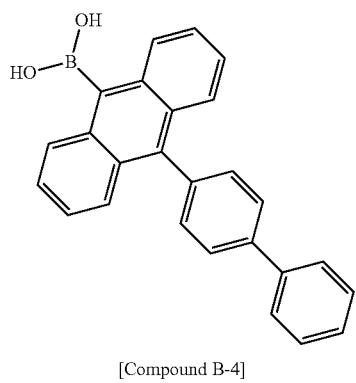

[Compound B-4]

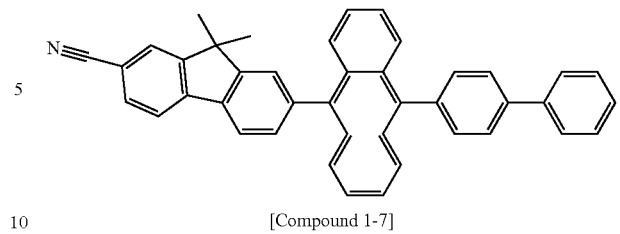

[Compound 1-7]

The compound of Formula 1-7 (7.34 g, 67%) was prepared in the same manner as in Example 1, except that Compound B-4 (7.49 g, 20.0 mmol) was used instead of Compound B-2 in Example 1.

MS: [M+H]$^+$=548

<Example 4> Preparation of Compound of Formula 1-12

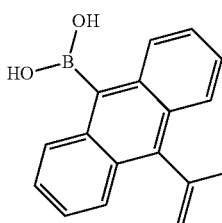

[Compound A-2]

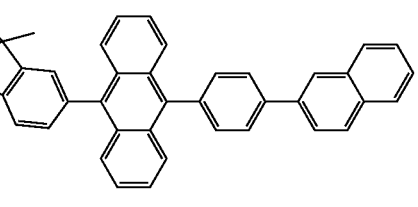

[Compound B-10]

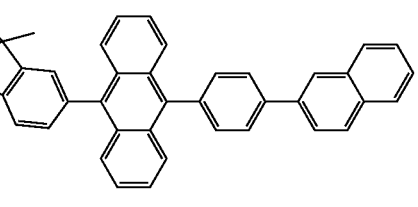

[Compound 1-12]

The compound of Formula 1-12 (7.77 g, 65%) was prepared in the same manner as in Example 1, except that Compound B-10 (8.49 g, 20.0 mmol) was used instead of Compound B-2 in Example 1.

MS: [M+H]$^+$=598

\<Example 5\> Preparation of Compound of Formula 1-18

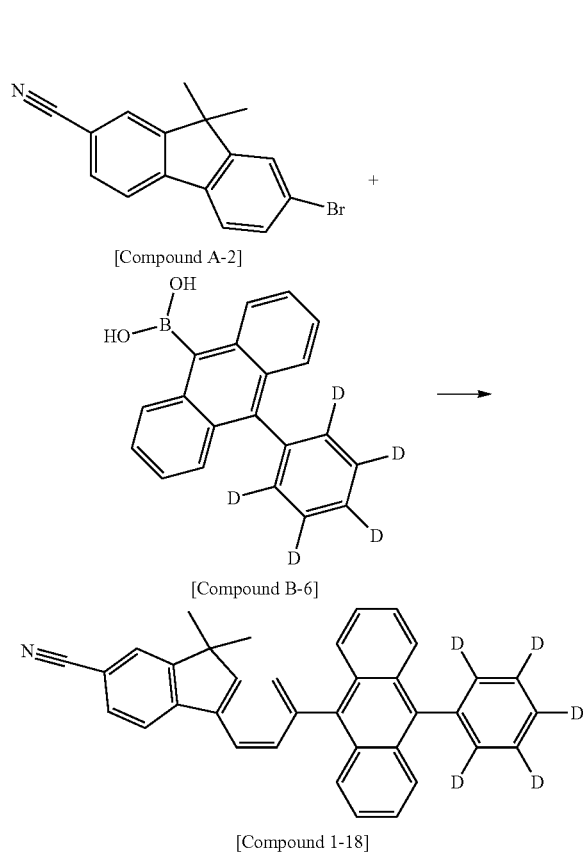

The compound of Formula 1-18 (5.82 g, 61%) was prepared in the same manner as in Example 1, except that Compound B-6 (6.06 g, 20.0 mmol) was used instead of Compound B-2 in Example 1.

MS: $[M+H]^+=477$

\<Example 6\> Preparation of Compound of Formula 1-25

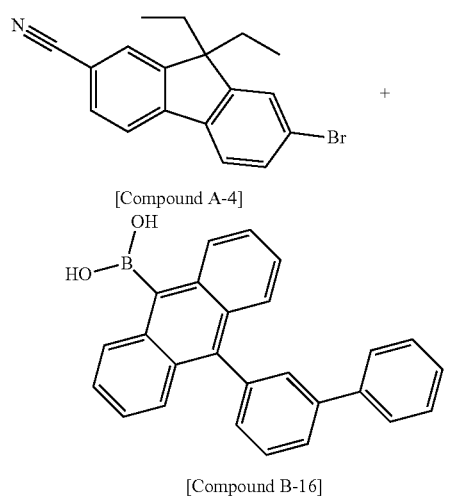

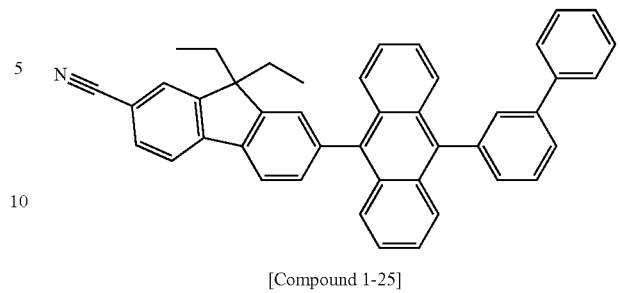

Compound A-4 (6.52 g, 20.0 mmol) and Compound B-16 (7.49 g, 20.0 mmol) were dispersed in tetrahydrofuran (100 mL), a 2 M potassium carbonate aqueous solution (aq. $K_2CO_3$) (40 mL) was added thereto, tetrakistriphenylphosphinopalladium $[Pd(PPh_3)_4]$ (0.462 g, 2 mol %) was put thereinto, and then the resulting mixture was stirred under reflux for 5 hours. The temperature was decreased to normal temperature, and the produced solid was filtered. The filtered solid was recrystallized with chloroform and ethanol and filtered, and then dried to prepare a compound of Formula 1-25 (6.79 g, 59%).

MS: $[M+H]^+=576$

\<Example 7\> Preparation of Compound of Formula 1-27

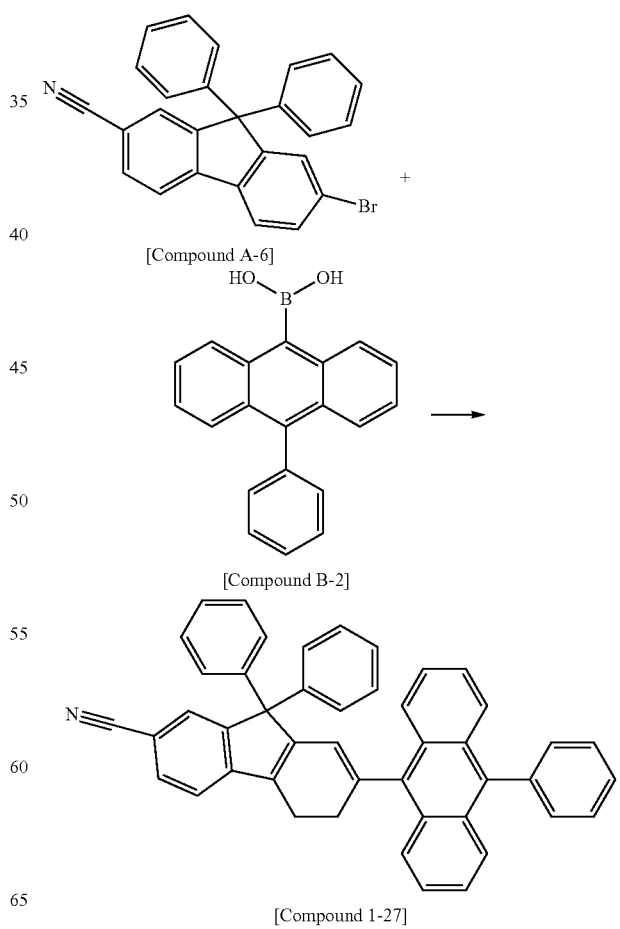

The compound of Formula 1-27 (7.51 g, 63%) was prepared in the same manner as in Example 1, except that Compound A-6 (8.45 g, 20.0 mmol) was used instead of Compound A-2 in Example 1.

MS: $[M+H]^+$=596

<Example 8> Preparation of Compound of Formula 1-38

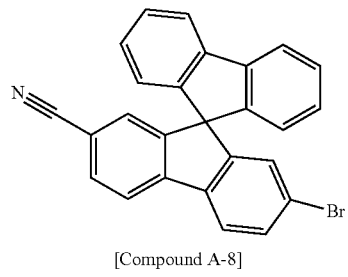

[Compound A-8]

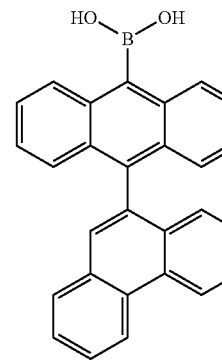

[Compound B-18]

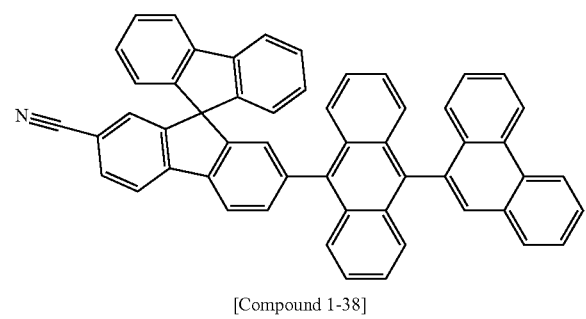

[Compound 1-38]

Compound A-8 (8.67 g, 20.0 mmol) and Compound B-18 (7.97 g, 20.0 mmol) were dispersed in tetrahydrofuran (100 mL), a 2 M potassium carbonate aqueous solution (aq. $K_2CO_3$) (40 mL) was added thereto, tetrakistriphenylphosphinopalladium [Pd(PPh$_3$)$_4$] (0.462 g, 2 mol %) was put thereinto, and then the resulting mixture was stirred under reflux for 5 hours. The temperature was decreased to normal temperature, and the produced solid was filtered. The filtered solid was recrystallized with chloroform and ethanol and filtered, and then dried to prepare a compound of Formula 1-38 (9.16 g, 66%).

MS: $[M+H]^+$=694

<Example 9> Preparation of Compound of Formula 2-1

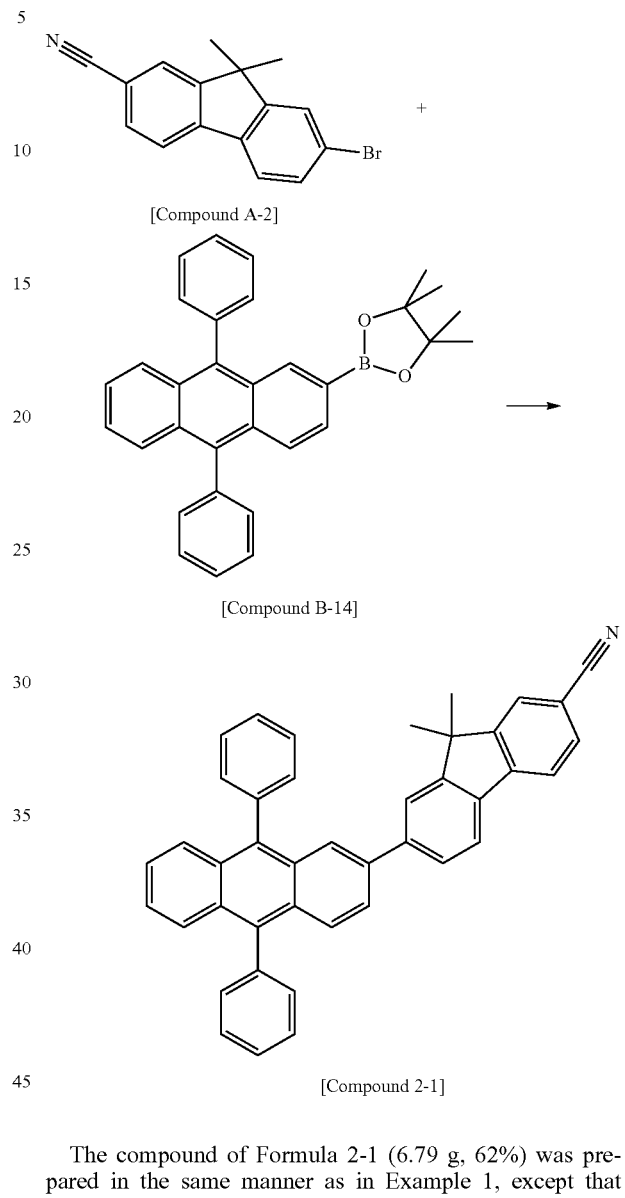

[Compound A-2]

[Compound B-14]

[Compound 2-1]

The compound of Formula 2-1 (6.79 g, 62%) was prepared in the same manner as in Example 1, except that Compound B-14 (9.12 g, 20.0 mmol) was used instead of Compound B-2 in Example 1.

MS: $[M+H]^+$=548

<Example 10> Preparation of Compound of Formula 2-5

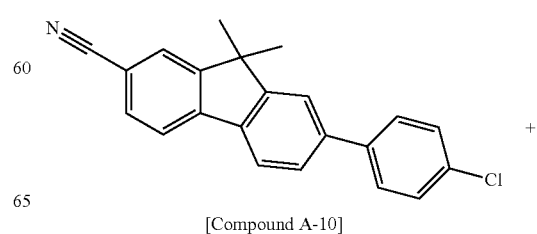

[Compound A-10]

-continued

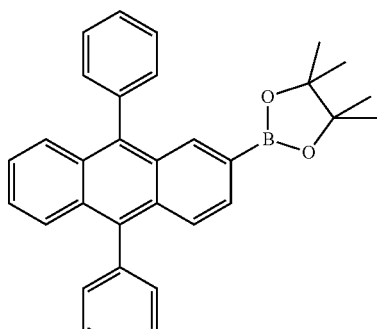

[Compound B-14]

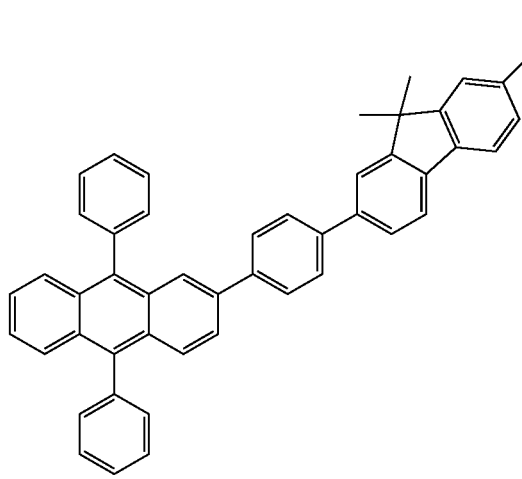

[Compound 2-5]

The compound of Formula 2-5 (6.86 g, 55%) was prepared in the same manner as in Example 9, except that Compound A-10 (6.60 g, 20.0 mmol) was used instead of Compound A-2 in Example 9.

MS: [M+H]⁺=624

<Example 11> Preparation of Compound of Formula 1-33

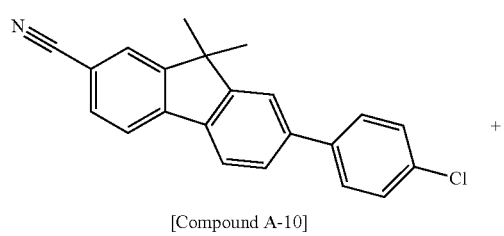

[Compound A-10]

-continued

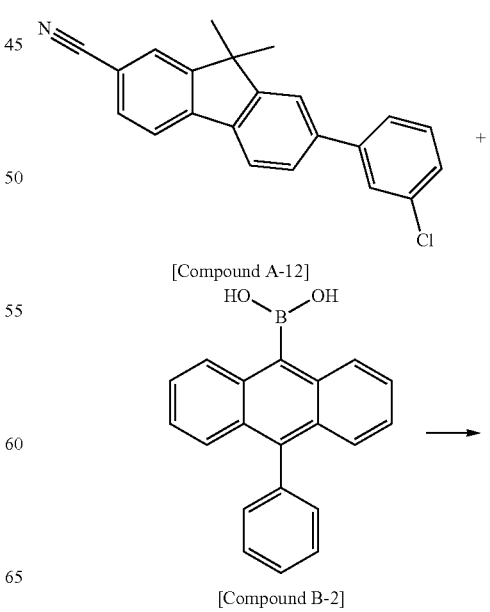

[Compound B-2]

[Compound 1-33]

Compound A-10 (6.60 g, 20.0 mmol) and Compound B-2 (5.96 g, 20.0 mmol) were dispersed in tetrahydrofuran (100 mL), a 2 M potassium carbonate aqueous solution (aq. K₂CO₃) (40 mL) was added thereto, tetrakistriphenylphosphinopalladium [Pd(PPh₃)₄] (0.462 g, 2 mol %) was put thereinto, and then the resulting mixture was stirred under reflux for 48 hours. The temperature was decreased to normal temperature, and the produced solid was filtered. The filtered solid was recrystallized with chloroform and ethyl acetate and filtered, and then dried to prepare a compound of Formula 1-33 (6.79 g, 62%).

MS: [M+H]⁺=548

<Example 12> Preparation of Compound of Formula 1-34

[Compound A-12]

[Compound B-2]

-continued

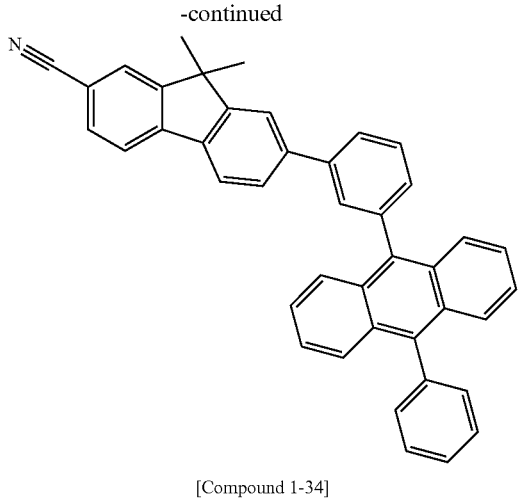

[Compound 1-34]

The compound of Formula 1-34 (6.24 g, 57%) was prepared in the same manner as in Example 11, except that Compound A-12 (6.60 g, 20.0 mmol) was used instead of Compound A-10 in Example 11.

MS: [M+H]$^+$=548

<Example 13> Preparation of Compound of Formula 3-1

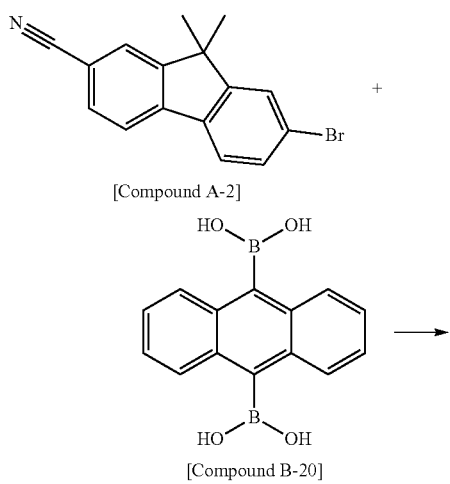

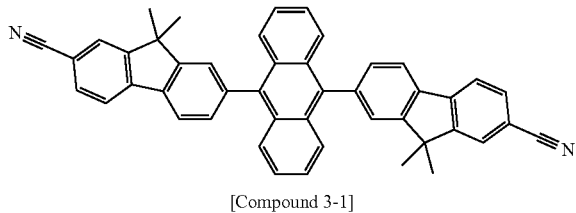

[Compound 3-1]

The compound of Formula 3-1 (4.41 g, 72%) was prepared in the same manner as in Example 1, except that Compound B-20 (2.66 g, 10.0 mmol) was used instead of Compound B-2 in Example 1.

MS: [M+H]$^+$=613

<Example 14> Preparation of Compound of Formula 3-2

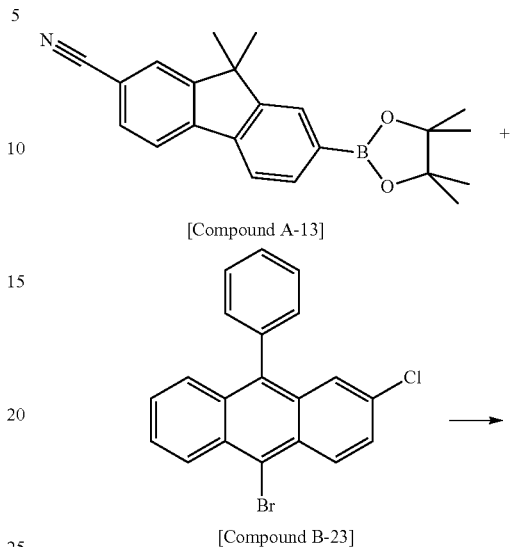

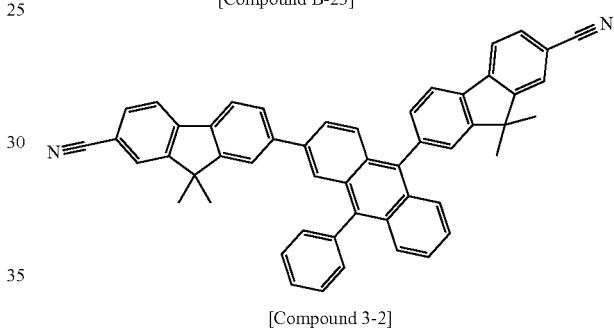

[Compound 3-2]

Compound A-13 (13.8 g, 40.0 mmol) and Compound B-23 (5.96 g, 20.0 mmol) were dispersed in toluene (120 mL), tris(dibenzyledeneacetone)2palladium (0) (0.69 g, 3 mol %), tricyclohexylphosphine (0.67 g, 6 mol %), and tripotassium phosphate (K$_3$PO$_4$) were put thereinto, and then the resulting mixture was stirred under reflux for 4 hours. The temperature was decreased to normal temperature, and the produced solid was filtered. The filtered solid was recrystallized with chloroform and ethyl acetate and filtered, and then dried to prepare a compound of Formula 3-2 (7.30 g, 53%).

MS: [M+H]$^+$=689

<Example 15> Preparation of Compound of Formula 3-3

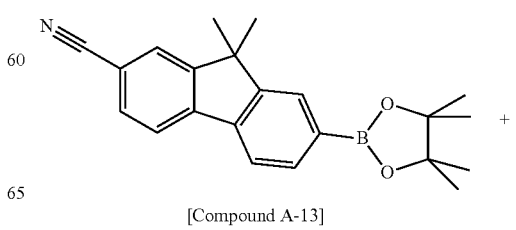

[Compound A-13]

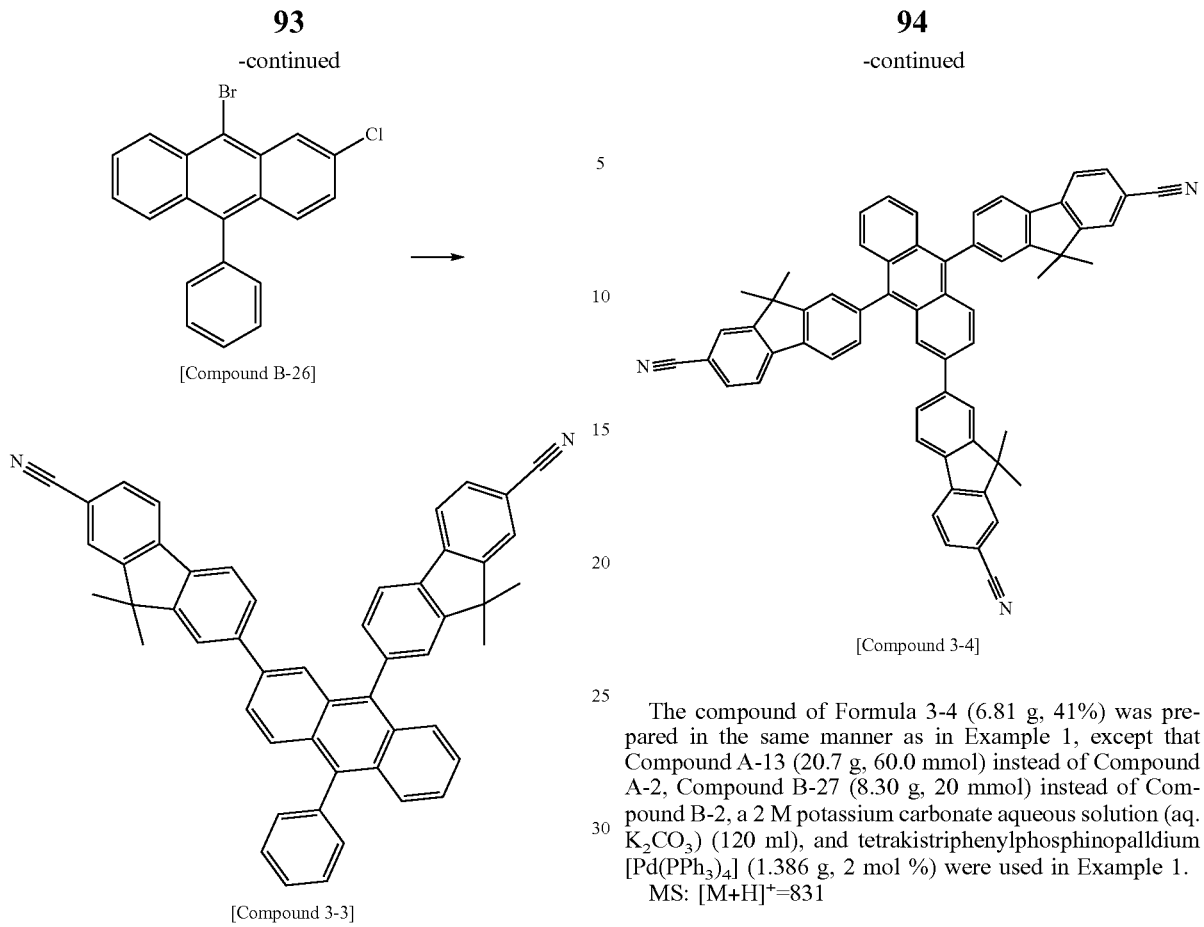

[Compound B-26]

[Compound 3-3]

The compound of Formula 3-3 (5.92 g, 43%) was prepared in the same manner as in Example 13, except that Compound B-26 was used instead of Compound B-23 in Example 14.

MS: [M+H]⁺=689

<Example 16> Preparation of Compound of Formula 3-4

[Compound A-13]

[Compound B-27]

[Compound 3-4]

The compound of Formula 3-4 (6.81 g, 41%) was prepared in the same manner as in Example 1, except that Compound A-13 (20.7 g, 60.0 mmol) instead of Compound A-2, Compound B-27 (8.30 g, 20 mmol) instead of Compound B-2, a 2 M potassium carbonate aqueous solution (aq. $K_2CO_3$) (120 ml), and tetrakistriphenylphosphinopalldium [Pd(PPh₃)₄] (1.386 g, 2 mol %) were used in Example 1.

MS: [M+H]⁺=831

<Example 17> Preparation of Compound of Formula 4-1

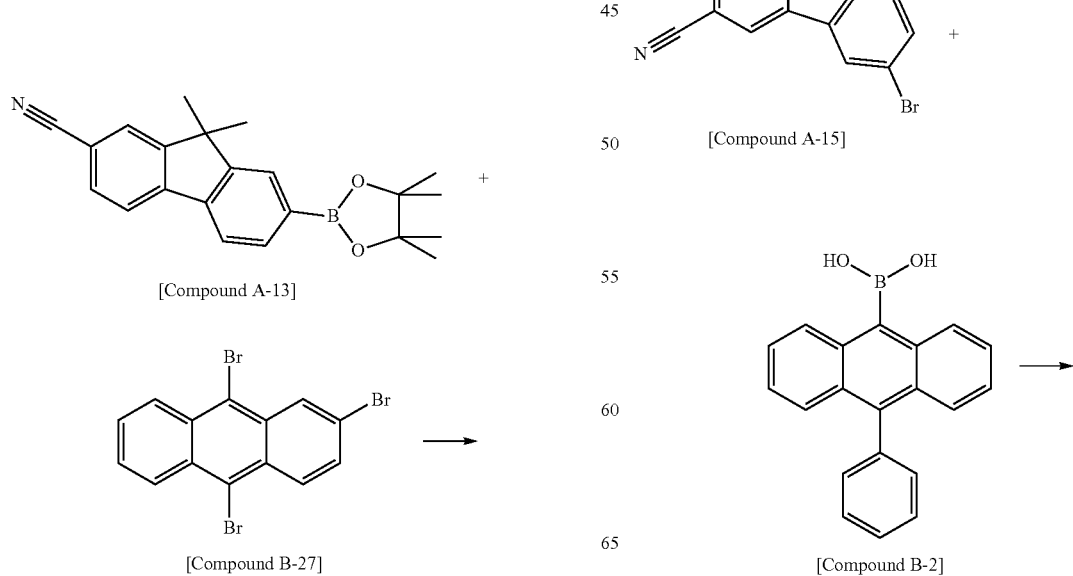

[Compound A-15]

[Compound B-2]

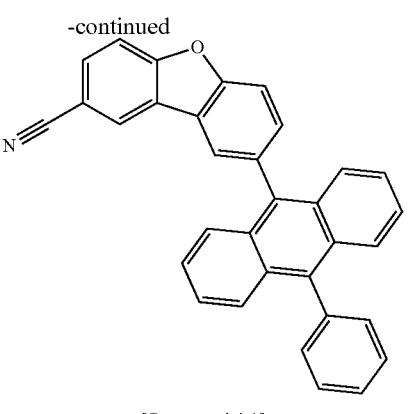

[Compound 4-1]

The compound of Formula 4-1 (6.33 g, 71%) was prepared in the same manner as in Example 1, except that Compound A-15 (5.44 g, 20.0 mmol) was used instead of Compound A-2 in Example 1.

MS: [M+H]$^+$=446

<Example 18> Preparation of Compound of Formula 4-2

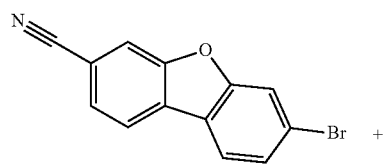

[Compound A-17]

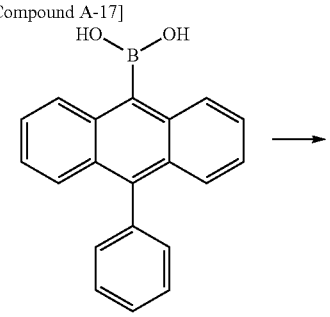

[Compound B-2]

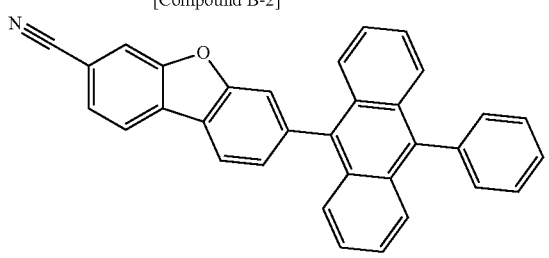

[Compound 4-2]

The compound of Formula 4-2 (6.51 g, 73%) was prepared in the same manner as in Example 1, except that Compound A-17 (5.44 g, 20.0 mmol) was used instead of Compound A-2 in Example 1.

MS: [M+H]$^+$=446

<Example 19> Preparation of Compound of Formula 4-3

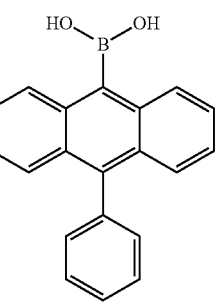

[Compound A-19]

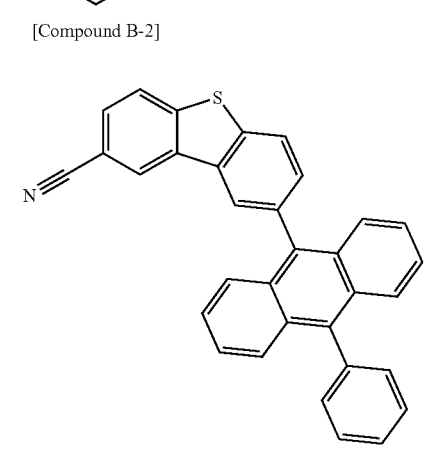

[Compound B-2]

[Compound 4-3]

The compound of Formula 4-3 (7.29 g, 79%) was prepared in the same manner as in Example 1, except that Compound A-19 (5.76 g, 20.0 mmol) was used instead of Compound A-2 in Example 1.

MS: [M+H]$^+$=462

<Example 20> Preparation of Compound of Formula 4-4

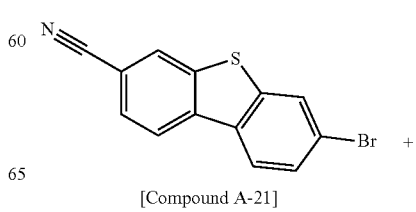

[Compound A-21]

-continued

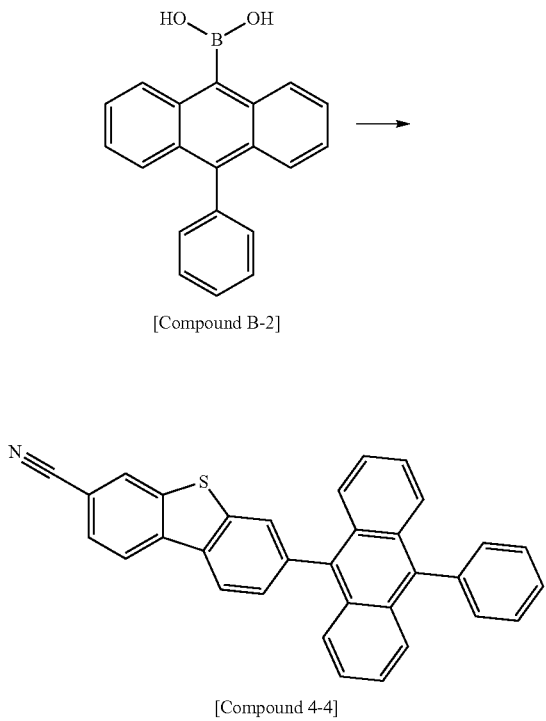

[Compound B-2]

[Compound 4-4]

The compound of Formula 4-4 (6.83 g, 74%) was prepared in the same manner as in Example 1, except that Compound A-21 (5.76 g, 20.0 mmol) was used instead of Compound A-2 in Example 1.

MS: $[M+H]^+$=462

Experimental Example

Experimental Example 1-1

A glass substrate on which a thin film of indium tin oxide (ITO) was coated to have a thickness of 500 Å was placed into distilled water in which a detergent was dissolved, and washed using ultrasonic waves. At this time, a product manufactured by Fischer Co. was used as the detergent, and distilled water, which had been filtered twice with a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

Hexanitrile hexaazatriphenylene (HAT) of the following Formula was thermally vacuum-deposited to have a thickness of 100 Å on a transparent ITO electrode, which was thus prepared, so as to form a hole injection layer.

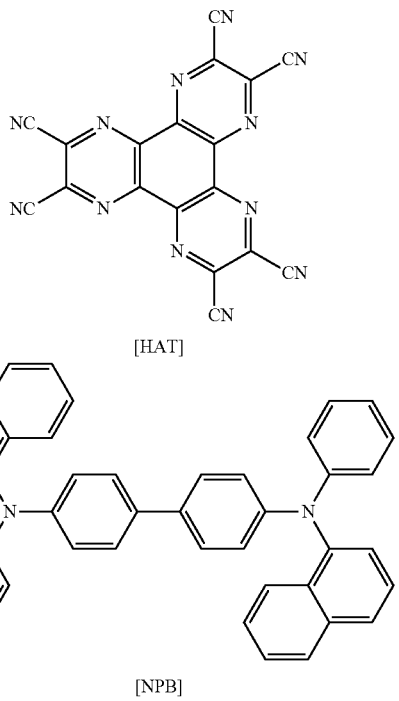

[HAT]

[NPB]

A hole transporting layer was formed by vacuum-depositing 4,4'-bis[N-(1-naphthyl)-N-phenylamino]biphenyl (NPB) (1,000 Å) of the above Formula on the hole injection layer.

Subsequently, a light emitting layer was formed by vacuum-depositing BH and BD shown below at a weight ratio of 10:1 to have a film thickness of 230 Å on the hole transporting layer.

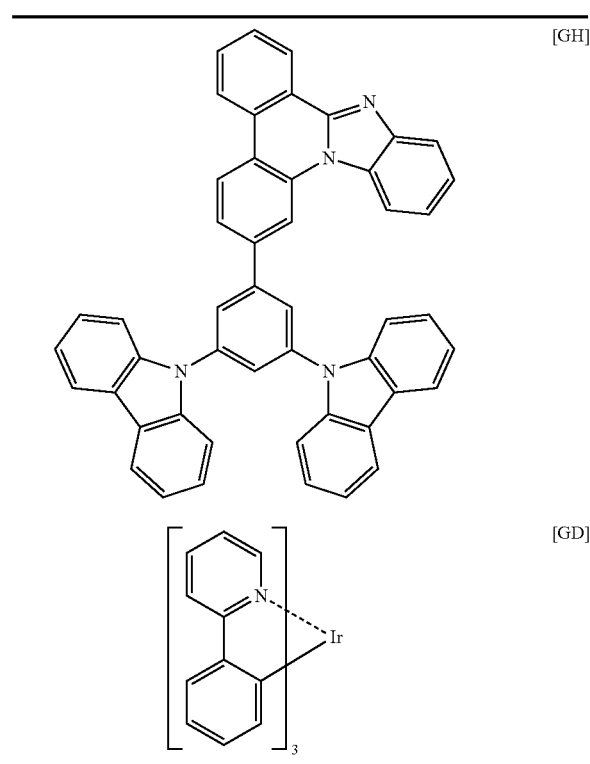

[GH]

[GD]

An electron injection and transporting layer was formed by vacuum-depositing the compound of Formula 1-1 on the light emitting layer to have a film thickness of 350 Å.

On the electron injection and transporting layer, lithium fluoride (LiF) and aluminum were deposited to have a thickness of 15 Å and 1,000 Å, respectively, to form a cathode.

In the above process, the deposition rate of the organic material was maintained at 0.4 to 0.7 Å/sec, the deposition rates of lithium fluoride and aluminum of the cathode were maintained at 0.3 Å/sec and 2 Å/sec, respectively, and the degree of vacuum during the deposition was maintained at $2 \times 10^{-7}$ to $5 \times 10^{-8}$ torr to manufacture an organic light emitting device.

Comparative Example 1

An organic light emitting device was manufactured in the same manner as in Experimental Example 1-1, except that a compound of the following Formula ET-A was used instead of the compound of Formula 1-1 in Experimental Example 1-1.

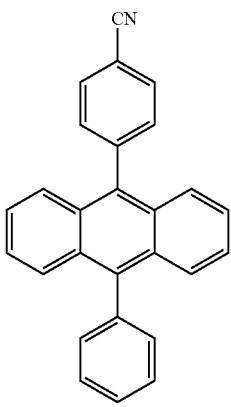

[ET-A]

Comparative Example 2

An organic light emitting device was manufactured in the same manner as in Experimental Example 1-1, except that a compound of the following Formula ET-B was used instead of the compound of Formula 1-1 in Experimental Example 1-1.

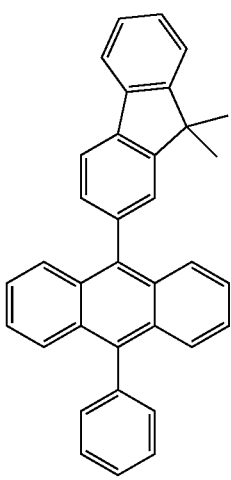

[ET-B]

Experimental Examples 1-2 to 1-13

Organic light emitting devices in Experimental Examples 1-2 to 1-13 were manufactured in the same manner as in Experimental Example 1-1, except that each compound shown in Table 2 was used instead of the compound of Formula 1-1 in Experimental Example 1-1.

When current (10 mA/cm$^2$) was applied to the organic light emitting devices manufactured by Experimental Examples 1-1 to 1-13 and Comparative Examples 1 and 2, the results shown in Table 2 were obtained.

TABLE 2

| | Compound | Voltage (V) | Efficiency (cd/A) | Color coordinate (x, y) |
|---|---|---|---|---|
| Experimental Example 1-1 | 1-1 | 3.56 | 42.24 | (0.374, 0.620) |
| Experimental Example 1-2 | 1-3 | 3.77 | 41.05 | (0.373, 0.619) |
| Experimental Example 1-3 | 1-7 | 3.60 | 42.07 | (0.375, 0.621) |
| Experimental Example 1-4 | 1-12 | 3.82 | 40.37 | (0.374, 0.620) |
| Experimental Example 1-5 | 1-25 | 3.82 | 41.22 | (0.373, 0.621) |
| Experimental Example 1-6 | 1-27 | 3.71 | 40.59 | (0.373, 0.620) |
| Experimental Example 1-7 | 3-1 | 3.87 | 40.02 | (0.374 0.619) |
| Experimental Example 1-8 | 3-2 | 3.76 | 41.01 | (0.374 0.621) |
| Experimental Example 1-9 | 3-3 | 3.78 | 40.28 | (0.373 0.621) |
| Experimental Example 1-10 | 3-4 | 3.90 | 40.12 | (0.375 0.620) |
| Experimental Example 1-10 | 4-1 | 3.72 | 40.00 | (0.375 0.618) |
| Experimental Example 1-11 | 4-2 | 3.81 | 40.09 | (0.374 0.619) |
| Experimental Example 1-12 | 4-3 | 3.74 | 41.10 | (0.373 0.618) |
| Experimental Example 1-13 | 4-4 | 3.87 | 41.27 | (0.373 0.620) |
| Comparative Example 1 | ET-A | 4.02 | 39.53 | (0.376, 0.622) |
| Comparative Example 2 | ET-B | 6.23 | 17.15 | (0.372, 0.614) |

From the results in Table 2, it can be seen that the new anthracene derivative compound according to an exemplary embodiment of the present application may be used as a material for the organic material layer of the organic light emitting device, and particularly, when the compound was used for the electron injection and transporting layer of the organic material layers, the organic light emitting device shows excellent characteristics in terms of efficiency, driving voltage, stability, and the like. In particular, it can be confirmed that the compound has excellent thermal stability, a deep HOMO level, and hole stability, and thus shows excellent characteristics. The compound is advantageous in improving efficiency, and stability of the device may be improved due to thermal stability of the compound.

Experimental Example 2-1

Hexanitrile hexaazatriphenylene (HAT) of the above Formula was thermally vacuum-deposited to have a thickness of 100 Å, on a transparent ITO electrode, which was prepared as in Experimental Example 1-1, so as to form a hole injection layer.

A hole transporting layer was formed by subsequently vacuum-depositing 4,4'-bis[N-(1-naphthyl)-N-phenylamino]biphenyl (NPB) (700 Å) of the above Formula, hexanitrile hexaazatriphenylene (HAT) (50 Å), and 4,4'-bis [N-(1-naphthyl)-N-phenylamino]biphenyl (NPB) (700 Å) on the hole injection layer.

Subsequently, a light emitting layer was formed by vacuum-depositing BH and BD shown below at a weight ratio of 25:1 to have a film thickness of 200 Å on the hole transporting layer.

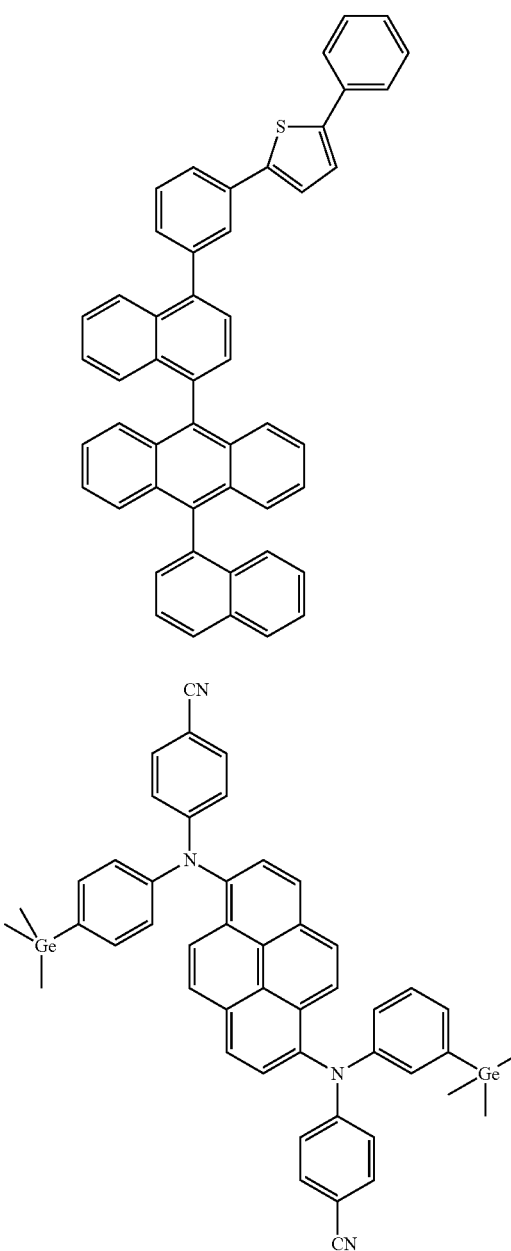

An electron injection and transporting layer having a thickness of 300 Å was formed by vacuum-depositing the compound of Formula 1-1 and lithium quinalate (LiQ) of the following Formula at a weight ratio of 1:1 on the light emitting layer.

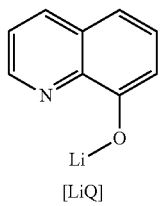

On the electron injection and transporting layer, lithium fluoride (LiF) and aluminum were deposited to have a thickness of 15 Å and 2,000 Å, respectively to form a cathode.

In the above process, the deposition rate of the organic material was maintained at 0.4 to 0.7 Å/sec, the deposition rates of lithium fluoride and aluminum of the cathode were maintained at 0.3 Å/sec and 2 Å/sec, respectively, and the degree of vacuum during the deposition was maintained at $2\times10^{-7}$ to $5\times10^{-8}$ torr to manufacture an organic light emitting device.

Comparative Example 3

An organic light emitting device was manufactured in the same manner as in Experimental Example 2-1, except that a compound of the following Formula ET-C was used instead of the compound of Formula 1-1 in Experimental Example 2-1.

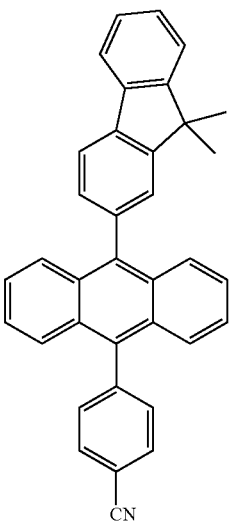

Experimental Examples 2-2 to 2-6

Organic light emitting devices in Experimental Examples 2-2 to 2-6 were manufactured in the same manner as in Experimental Example 2-1, except that each compound shown in Table 3 was used instead of the compound of Formula 1-1 in Experimental Example 2-1.

When current (10 mA/cm$^2$) was applied to the organic light emitting devices manufactured by Experimental Examples 2-1 to 2-6 and Comparative Example 3, the results shown in Table 3 were obtained.

TABLE 3

| Compound | | Voltage (V) | Efficiency (cd/A) | Color coordinate (x, y) |
|---|---|---|---|---|
| Experimental Example 2-1 | 1-1 | 3.76 | 5.06 | (0.141, 0.129) |
| Experimental Example 2-2 | 1-7 | 3.92 | 5.11 | (0.140, 0.130) |
| Experimental Example 2-3 | 1-18 | 3.79 | 5.09 | (0.141, 0.129) |
| Experimental Example 2-4 | 1-38 | 3.81 | 5.19 | (0.135, 0.131) |
| Experimental Example 2-5 | 2-1 | 3.95 | 4.96 | (0.142, 0.130) |
| Experimental Example 2-6 | 2-5 | 3.92 | 4.90 | (0.142, 0.131) |
| Comparative Example 3 | ET-C | 4.05 | 4.72 | (0.140, 0.129) |

From the results in Table 3, it can be seen that the compound according to an exemplary embodiment of the present application may be used as a material for the organic material layer of the organic light emitting device, and particularly, when the compound was used for the electron injection and transporting layer of the organic material layers, the organic light emitting device shows excellent characteristics in terms of efficiency, driving voltage, stability, and the like. In particular, the compound has excellent thermal stability, a deep HOMO level, and hole stability, and thus shows excellent characteristics. The compound may be used either purely or by being mixed with an n-type dopant such as LiQ in an organic electronic device including an organic light emitting device. The compound improves efficiency of the organic light emitting device, and stability of the device may be improved due to thermal stability of the compound.

What is claimed is:

1. An organic electronic device comprising:
a first electrode;
a second electrode; and
an organic material layer having one or more layers disposed between the first electrode and the second electrode,
wherein the organic material layer comprises a light emitting layer and at least one layer selected from an electron transporting layer, an electron injection layer, and a layer which transports and injects electrons simultaneously, and
wherein at least one of the electron transporting layer, the electron injection layer, and the layer which transports and injects electrons simultaneously comprises a compound represented by the following Formula 1:

[Formula 1]

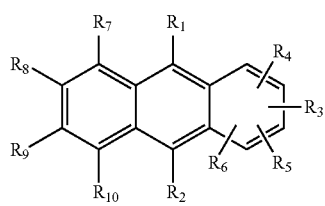

in Formula 1,
$R_1$ and $R_2$ are the same as or different from each other, and are each independently a substituted or unsubstituted alkenyl group having 2 to 40 carbon atoms; a substituted or unsubstituted aryl group having 6 to 60 carbon atoms; a substituted or unsubstituted fluorenyl group; or a substituted or unsubstituted heterocyclic group including one or more of N, O, and S atoms having 2 to 60 carbon atoms, $R_3$ to $R_{10}$ are the same as or different from each other, and are each independently hydrogen; deuterium; a halogen group; a nitrile group; a nitro group; a hydroxyl group; a substituted or unsubstituted alkyl group having 1 to 30 carbon atoms; a substituted or unsubstituted cycloalkyl group having 3 to 60 carbon atoms; a substituted or unsubstituted alkoxy group having 1 to 30 carbon atoms; a substituted or unsubstituted alkylthioxy group having 1 to 30 carbon atoms; a substituted or unsubstituted arylthioxy group having 6 to 60 carbon atoms; a substituted or unsubstituted alkenyl group having 2 to 40 carbon atoms; a substituted or unsubstituted aryl group having 6 to 60 carbon atoms; a substituted or unsubstituted fluorenyl group; or a substituted or unsubstituted heterocyclic group including one or more of N, O, and S atoms having 2 to 60 carbon atoms, at least one of $R_1$ to $R_3$ is a group of the following Formula 2,

[Formula 2]

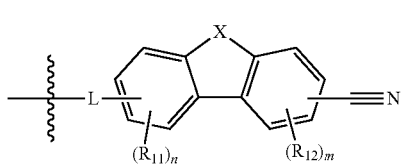

X is $CR_aR_b$,
$R_a$, $R_b$, $R_{11}$, and $R_{12}$ are the same as or different from each other, and are each independently hydrogen; deuterium; a halogen group; a nitrile group; a nitro group; a hydroxyl group; a substituted or unsubstituted alkyl group having 1 to 30 carbon atoms; a substituted or unsubstituted cycloalkyl group having 3 to 60 carbon atoms; a substituted or unsubstituted alkoxy group having 1 to 30 carbon atoms; a substituted or unsubstituted alkylthioxy group having 1 to 30 carbon atoms; a substituted or unsubstituted arylthioxy group having 6 to 60 carbon atoms; a substituted or unsubstituted alkenyl group having 2 to 40 carbon atoms; a substituted or unsubstituted aryl group having 6 to 60 carbon atoms; a substituted or unsubstituted fluorenyl group; or a substituted or unsubstituted heterocyclic group including one or more of N, O, and S atoms having 2 to 60 carbon atoms, and two or more adjacent groups among $R_a$, $R_b$, $R_{11}$, and $R_{12}$ are optionally bonded to each other to form a monocyclic or polycyclic ring, L is a direct bond; a substituted or unsubstituted arylene group having 6 to 60 carbon atoms; a substituted or unsubstituted alkenylene group having 2 to 40 carbon atoms; a substituted or unsubstituted fluorenylene group; or a substituted or unsubstituted heteroarylene group including one or more of N, O, and S atoms having 2 to 60 carbon atoms, and n and m are each independently an integer from 0 to 3.

2. The organic electronic device of claim 1, wherein the compound represented by Formula 1 is represented by any one of the following Formulae 3 to 8:

[Formula 3]
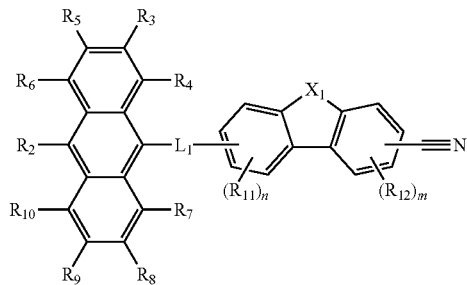
[Formula 4]
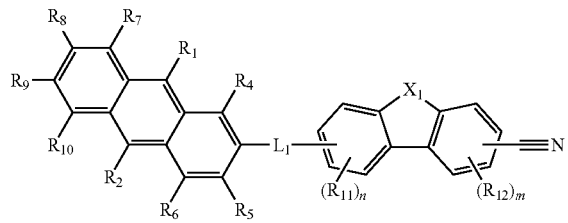
[Formula 5]
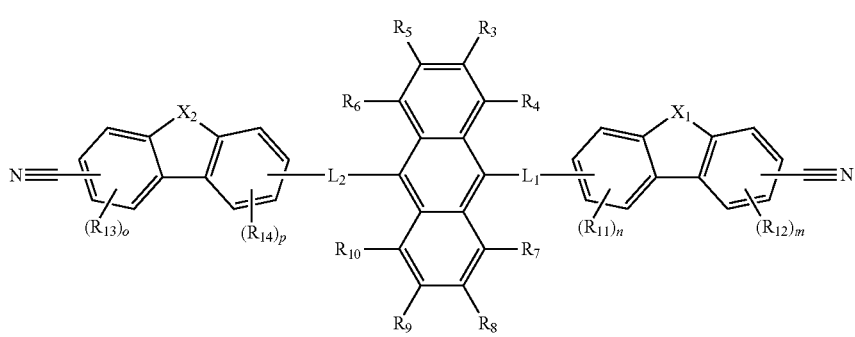
[Formula 6]
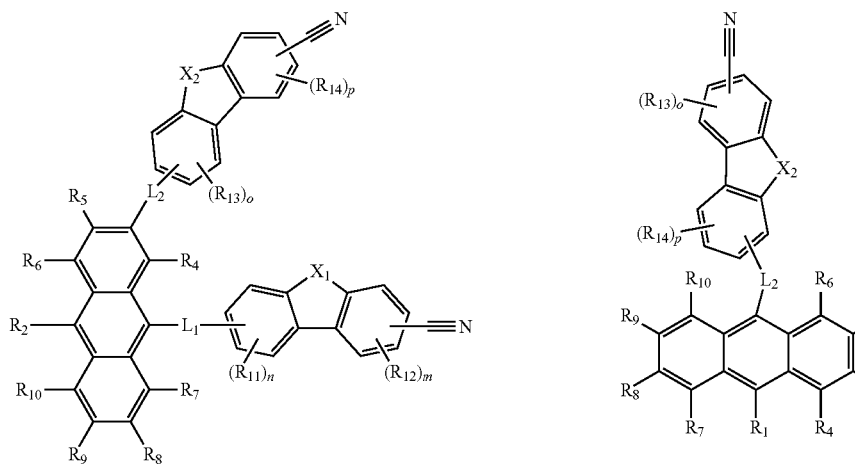
[Formula 7]
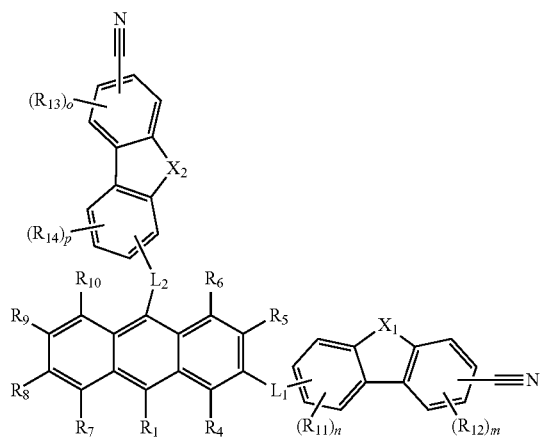
[Formula 8]
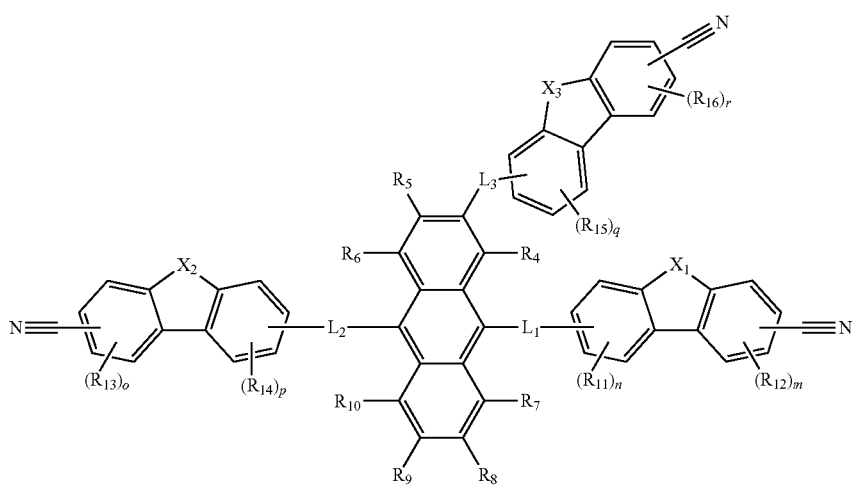

in Formulae 3 to 8, $X_1$ to $X_3$ are each independently $CR_aR_b$, $R_1$ to $R_{12}$, $R_a$, $R_b$, n, and m are the same as those defined in claim 1, $R_{13}$ to $R_{16}$ are the same as or different from each other, and are each independently hydrogen; deuterium; a halogen group; a nitrile group; a nitro group; a hydroxyl group; a substituted or unsubstituted alkyl group having from 1 to 30 carbon atoms; a substituted or unsubstituted cycloalkyl group having from 3 to 60 carbon atoms; a substituted or unsubstituted alkoxy group having from 1 to 30 carbon atoms; a substituted or unsubstituted alkylthioxy group having from 1 to 30 carbon atoms; a substituted or unsubstituted arylthioxy group having from 6 to 60 carbon atoms; a substituted or unsubstituted alkenyl group having from 2 to 40 carbon atoms; a substituted or unsubstituted aryl group having from 6 to 60 carbon atoms; a substituted or unsubstituted fluorenyl group; or a substituted or unsubstituted heterocyclic group including one or more of N, O, and S atoms having from 2 to 60 carbon atoms, and two or more adjacent groups among $R_1$ to $R_{16}$, $R_a$ and $R_b$ are optionally bonded to each other to form a monocyclic or polycyclic ring, $L_1$ to $L_3$ are each independently a direct bond; a substituted or unsubstituted arylene group having from 6 to 60 carbon atoms; a substituted or unsubstituted alkenylene group having from 2 to 40 carbon atoms; a substituted or unsubstituted fluorenylene group; or a substituted or unsubstituted heteroarylene group including one or more of N, O, and S atoms having from 2 to 60 carbon atoms, and o, p, q, and r are each independently an integer from 0 to 3.

3. The organic electronic device of claim 1, wherein L is a direct bond; a substituted or unsubstituted phenylene group; a substituted or unsubstituted naphthylene group; a substituted or unsubstituted fluorenylene group; a substituted or unsubstituted pyridylene group; or a substituted or unsubstituted biphenylene group.

4. The organic electronic device claim 1, wherein at least one of $R_1$ and $R_2$ are each independently selected from the group consisting of the following substituted or unsubstituted structural formulae:

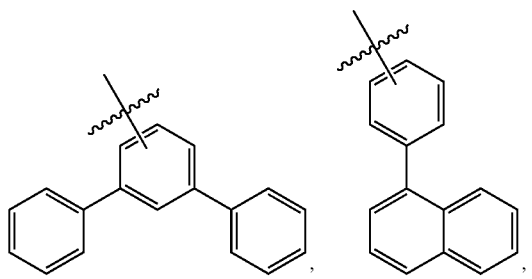

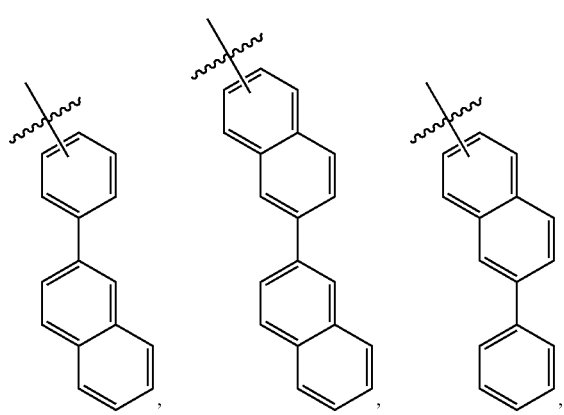

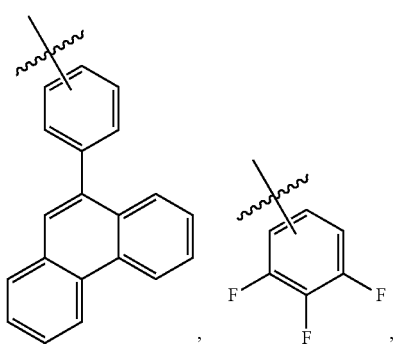

-continued

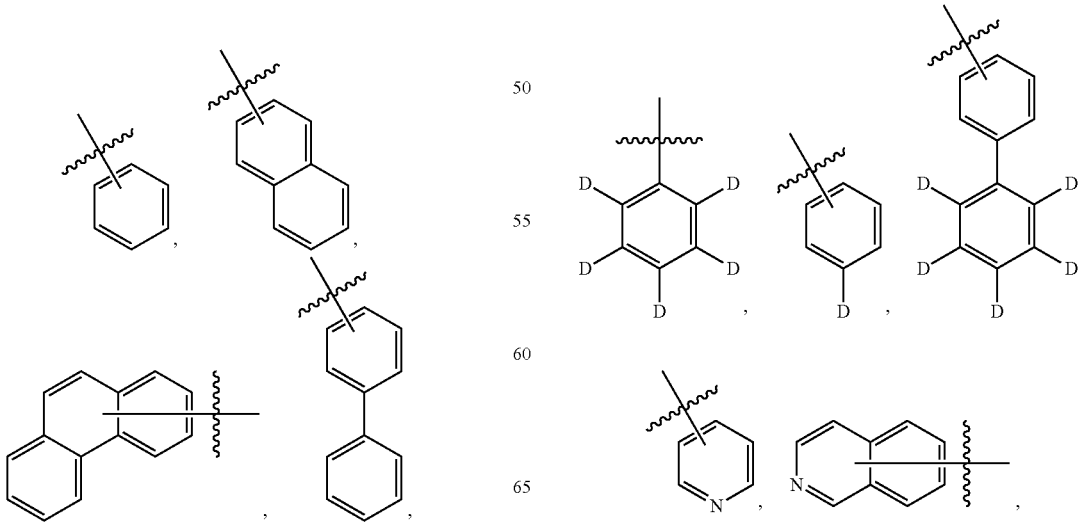

-continued

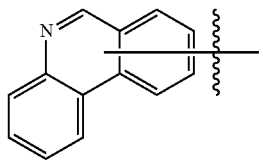
and
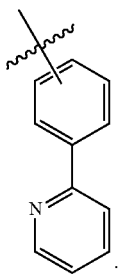
.

5. The organic electronic device of claim 1, wherein $R_a$ and $R_b$ are the same as or different from each other, and are each independently a substituted or unsubstituted methyl group; a substituted or unsubstituted ethyl group; a substituted or unsubstituted phenyl group; a substituted or unsubstituted biphenyl group; a substituted or unsubstituted terphenyl group; a substituted or unsubstituted pyridyl group; a substituted or unsubstituted quinoline group; a substituted or unsubstituted phenanthrenyl group; or a substituted or unsubstituted naphthyl group, and $R_a$ and $R_b$ are optionally bonded to each other to form a monocyclic or polycyclic ring.

6. The organic electronic device of claim 1, wherein the compound represented by Formula 1 is any one of the following Formulas in Table 1:

TABLE 1

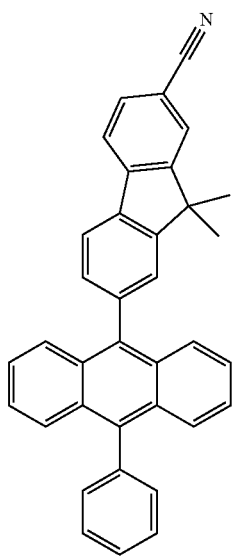 [SMILES: CC1(C)c2cc(C#N)ccc2-c2ccc(-c3c4ccccc4c(-c4ccccc4)c4ccccc34)cc21]

[Formula 1-1]

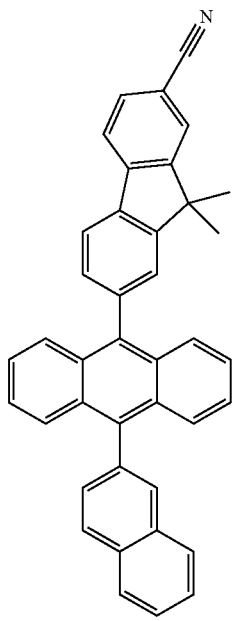 [SMILES: CC1(C)c2cc(C#N)ccc2-c2ccc(-c3c4ccccc4c(-c4ccc5ccccc5c4)c4ccccc34)cc21]

[Formula 1-2]

TABLE 1-continued
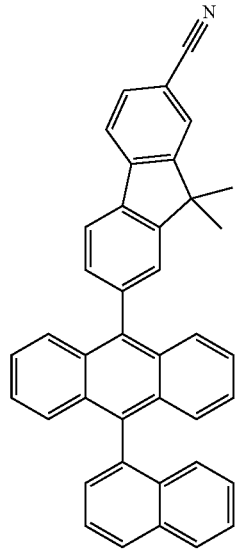 [SMILES: CC1(C)c2cc(C#N)ccc2-c2ccc(-c3c4ccccc4c(-c4cccc5ccccc45)c4ccccc34)cc21]
[Formula 1-3]
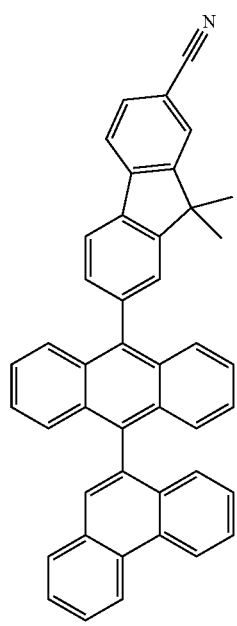 [SMILES: CC1(C)c2cc(C#N)ccc2-c2ccc(-c3c4ccccc4c(-c4cc5ccccc5c5ccccc45)c4ccccc34)cc21]
[Formula 1-4]

TABLE 1-continued
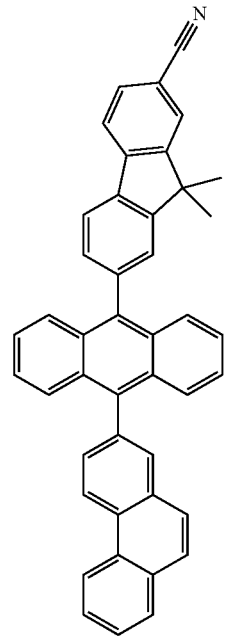 [SMILES: CC1(C)c2cc(C#N)ccc2-c2ccc(-c3c4ccccc4c(-c4ccc5c(ccc6ccccc65)c4)c4ccccc34)cc21]
[Formula 1-5]
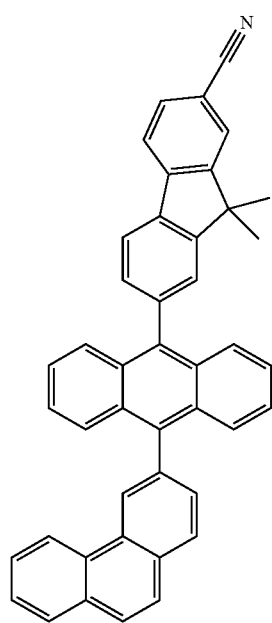 [SMILES: CC1(C)c2cc(C#N)ccc2-c2ccc(-c3c4ccccc4c(-c4ccc5ccc6ccccc6c5c4)c4ccccc34)cc21]
[Formula 1-6]

TABLE 1-continued
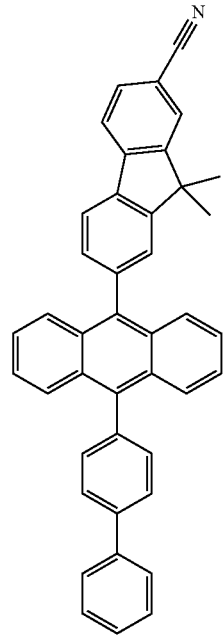
[Formula 1-7]
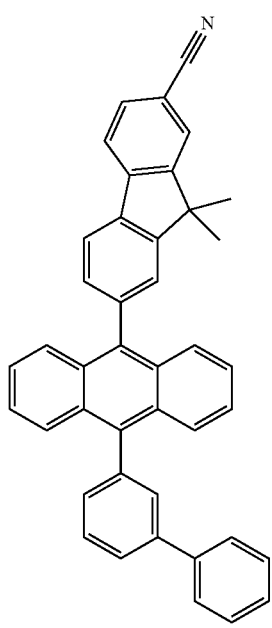 [SMILES: CC1(C)c2cc(C#N)ccc2-c2ccc(-c3c4ccccc4c(-c4cccc(-c5ccccc5)c4)c4ccccc34)cc21]
[Formula 1-8]

TABLE 1-continued
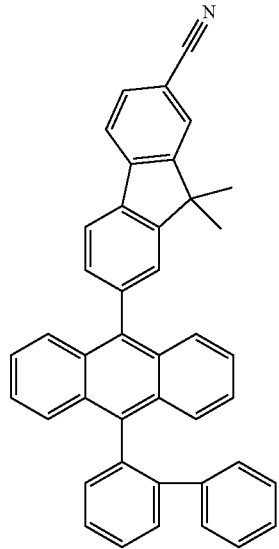 [SMILES: CC1(C)c2cc(C#N)ccc2-c2ccc(-c3c4ccccc4c(-c4ccccc4-c4ccccc4)c4ccccc34)cc21]
[Formula 1-9]
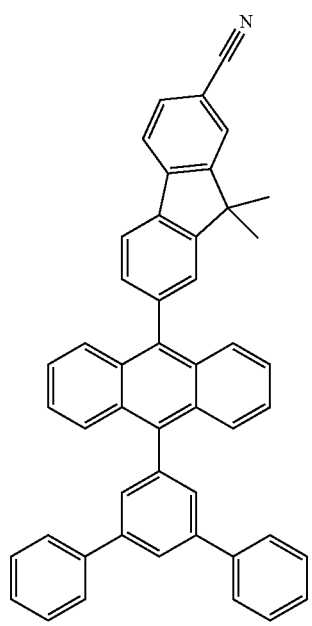 [SMILES: CC1(C)c2cc(C#N)ccc2-c2ccc(-c3c4ccccc4c(-c4cc(-c5ccccc5)cc(-c5ccccc5)c4)c4ccccc34)cc21]
[Formula 1-10]

TABLE 1-continued
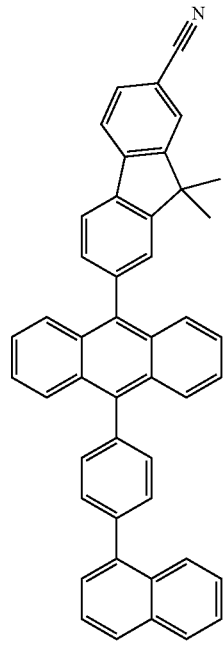 [SMILES: CC1(C)c2cc(C#N)ccc2-c2ccc(-c3c4ccccc4c(-c4ccc(-c5cccc6ccccc56)cc4)c4ccccc34)cc21]
[Formula 1-11]
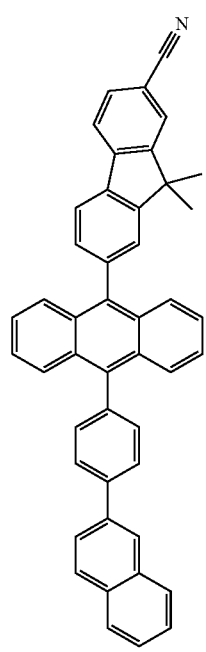 [SMILES: CC1(C)c2cc(C#N)ccc2-c2ccc(-c3c4ccccc4c(-c4ccc(-c5ccc6ccccc6c5)cc4)c4ccccc34)cc21]
[Formula 1-12]

TABLE 1-continued
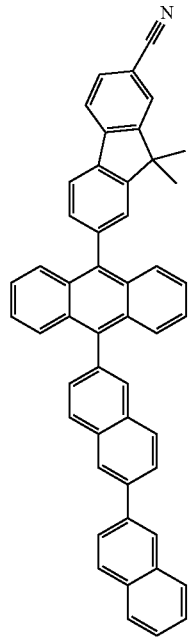 [SMILES: CC1(C)c2cc(C#N)ccc2-c2ccc(-c3c4ccccc4c(-c4ccc5cc(-c6ccc7ccccc7c6)ccc5c4)c4ccccc34)cc21]
[Formula 1-13]
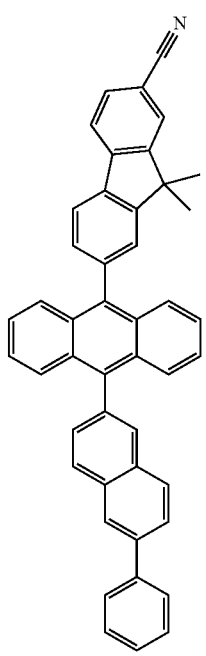 [SMILES: CC1(C)c2cc(C#N)ccc2-c2ccc(-c3c4ccccc4c(-c4ccc5cc(-c6ccccc6)ccc5c4)c4ccccc34)cc21]
[Formula 1-14]

TABLE 1-continued
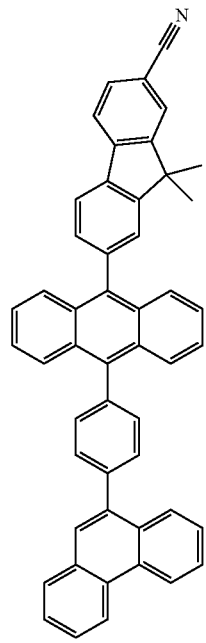 [SMILES: CC1(C)c2cc(C#N)ccc2-c2ccc(-c3c4ccccc4c(-c4ccc(-c5cc6ccccc6c6ccccc56)cc4)c4ccccc34)cc21]
[Formula 1-15]
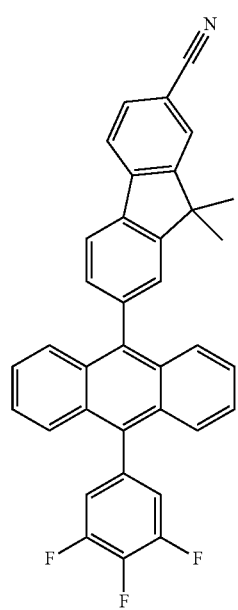 [SMILES: CC1(C)c2cc(C#N)ccc2-c2ccc(-c3c4ccccc4c(-c4cc(F)c(F)c(F)c4)c4ccccc34)cc21]
[Formula 1-16]

TABLE 1-continued
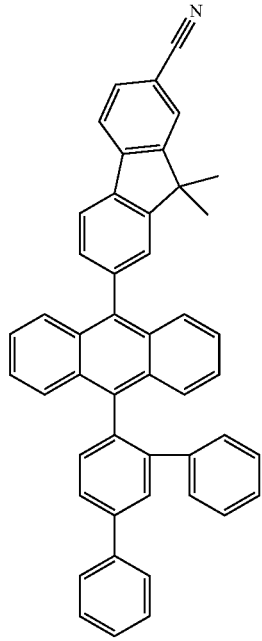 [SMILES: CC1(C)c2cc(C#N)ccc2-c2ccc(-c3c4ccccc4c(-c4ccc(-c5ccccc5)cc4-c4ccccc4)c4ccccc34)cc21]
[Formula 1-17]
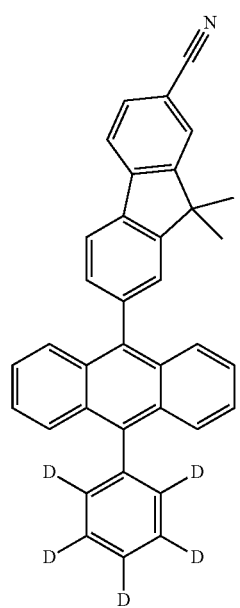 [SMILES: [2H]c1c([2H])c([2H])c(-c2c3ccccc3c(-c3ccc4c(c3)C(C)(C)c3cc(C#N)ccc3-4)c3ccccc23)c([2H])c1[2H]]
[Formula 1-18]

TABLE 1-continued
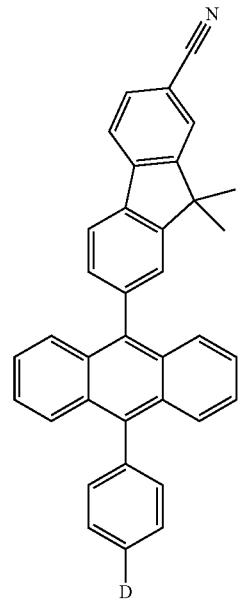 [SMILES: [2H]c1ccc(-c2c3ccccc3c(-c3ccc4c(c3)C(C)(C)c3cc(C#N)ccc3-4)c3ccccc23)cc1]
[Formula 1-19]
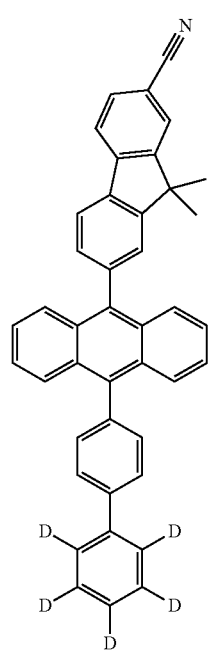 [SMILES: [2H]c1c([2H])c([2H])c(-c2ccc(-c3c4ccccc4c(-c4ccc5c(c4)C(C)(C)c4cc(C#N)ccc4-5)c4ccccc34)cc2)c([2H])c1[2H]]
[Formula 1-20]

TABLE 1-continued
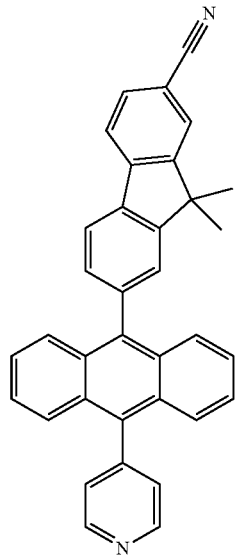 [SMILES: CC1(C)c2cc(C#N)ccc2-c2ccc(-c3c4ccccc4c(-c4ccncc4)c4ccccc34)cc21]
[Formula 1-21]
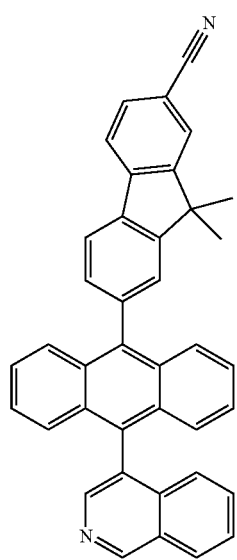 [SMILES: CC1(C)c2cc(C#N)ccc2-c2ccc(-c3c4ccccc4c(-c4cncc5ccccc45)c4ccccc34)cc21]
[Formula 1-22]

TABLE 1-continued
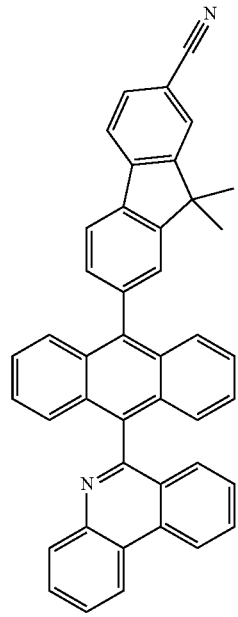 [SMILES: CC1(C)c2cc(C#N)ccc2-c2ccc(-c3c4ccccc4c(-c4nc5ccccc5c5ccccc45)c4ccccc34)cc21]
[Formula 1-23]
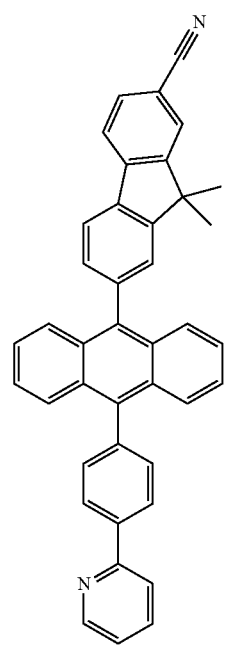
[Formula 1-24]

TABLE 1-continued
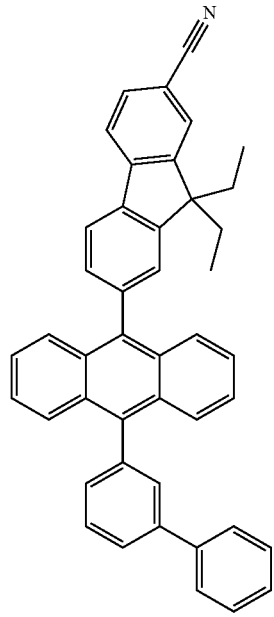 [SMILES: CCC1(CC)c2cc(C#N)ccc2-c2ccc(-c3c4ccccc4c(-c4cccc(-c5ccccc5)c4)c4ccccc34)cc21]
[Formula 1-25]
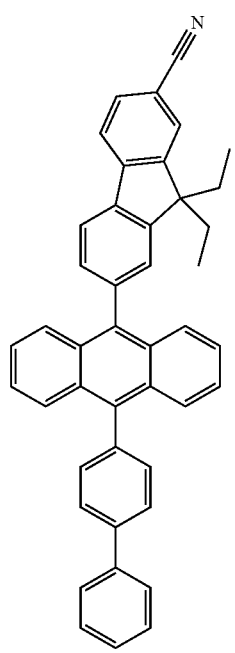 [SMILES: CCC1(CC)c2cc(C#N)ccc2-c2ccc(-c3c4ccccc4c(-c4ccc(-c5ccccc5)cc4)c4ccccc34)cc21]
[Formula 1-26]

TABLE 1-continued
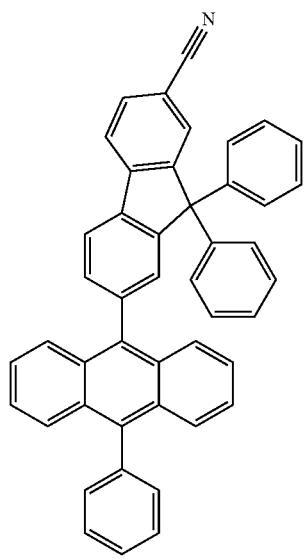
[Formula 1-27]
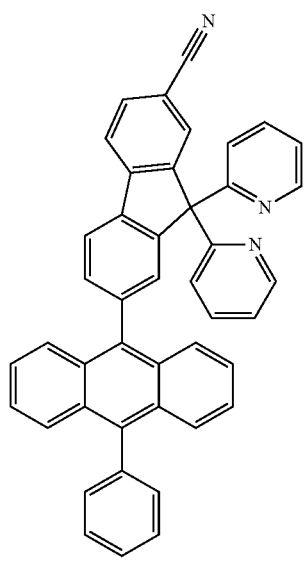 [SMILES: N#Cc1ccc2c(c1)C(c1ccccn1)(c1ccccn1)c1cc(-c3c4ccccc4c(-c4ccccc4)c4ccccc34)ccc1-2]
[Formula 1-28]
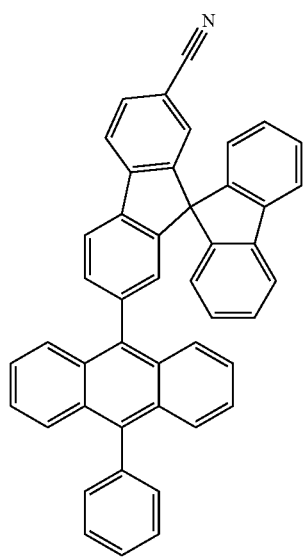 [SMILES: N#Cc1ccc2c(c1)C1(c3ccccc3-c3ccccc31)c1cc(-c3c4ccccc4c(-c4ccccc4)c4ccccc34)ccc1-2]
[Formula 1-29]

TABLE 1-continued
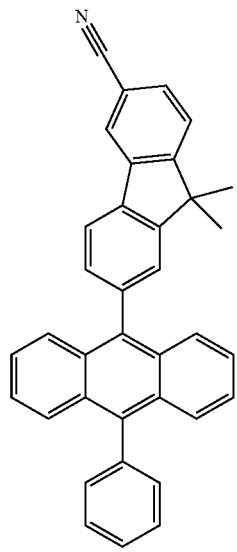 [SMILES: CC1(C)c2ccc(C#N)cc2-c2ccc(-c3c4ccccc4c(-c4ccccc4)c4ccccc34)cc21]
[Formula 1-30]
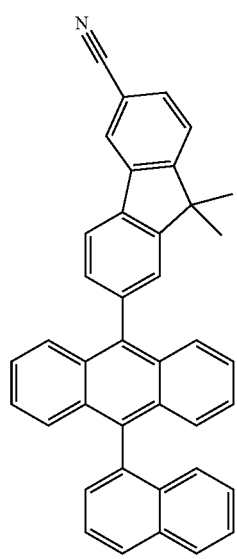 [SMILES: CC1(C)c2ccc(C#N)cc2-c2ccc(-c3c4ccccc4c(-c4cccc5ccccc45)c4ccccc34)cc21]
[Formula 1-31]
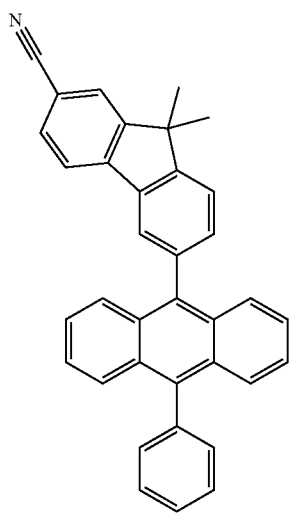
[Formula 1-32]

TABLE 1-continued
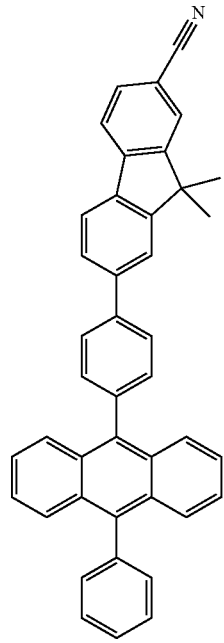
[Formula 1-33]
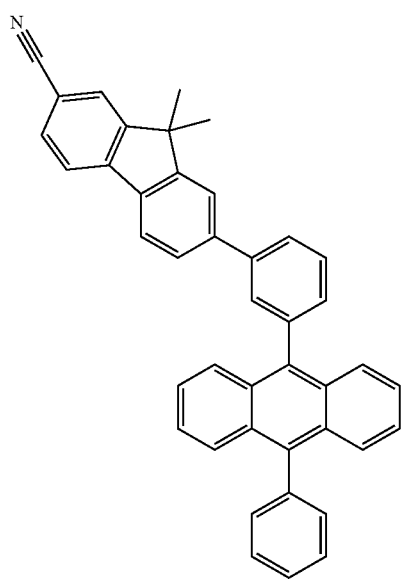 [SMILES: CC1(C)c2cc(C#N)ccc2-c2ccc(-c3cccc(-c4c5ccccc5c(-c5ccccc5)c5ccccc45)c3)cc21]
[Formula 1-34]

TABLE 1-continued
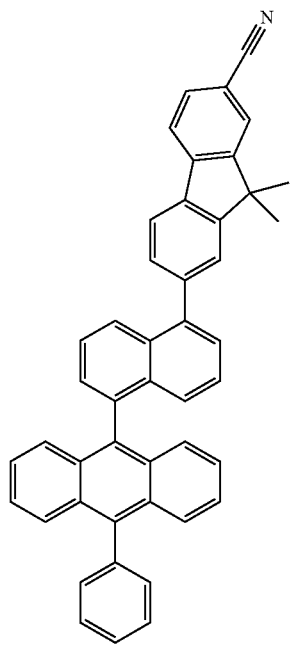 [SMILES: CC1(C)c2cc(C#N)ccc2-c2ccc(-c3cccc4c(-c5c6ccccc6c(-c6ccccc6)c6ccccc56)cccc34)cc21]
[Formula 1-35]
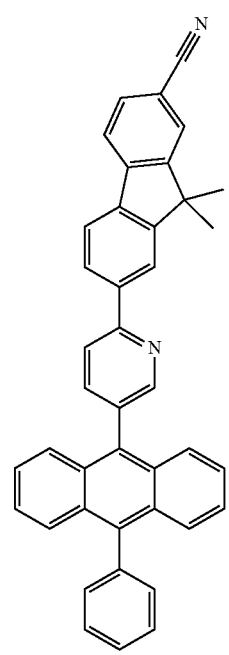 [SMILES: CC1(C)c2cc(C#N)ccc2-c2ccc(-c3ccc(-c4c5ccccc5c(-c5ccccc5)c5ccccc45)cn3)cc21]
[Formula 1-36]

TABLE 1-continued
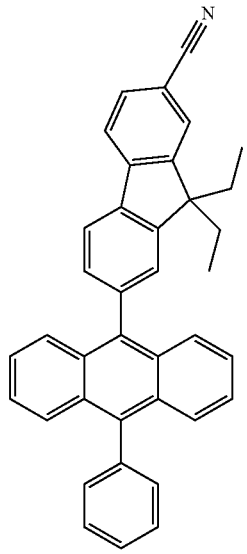 [SMILES: CCC1(CC)c2cc(C#N)ccc2-c2ccc(-c3c4ccccc4c(-c4ccccc4)c4ccccc34)cc21]
[Formula 1-37]
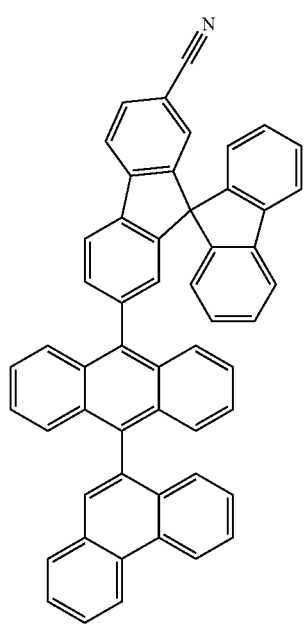 [SMILES: N#Cc1ccc2c(c1)C1(c3ccccc3-c3ccccc31)c1cc(-c3c4ccccc4c(-c4cc5ccccc5c5ccccc45)c4ccccc34)ccc1-2]
[Formula 1-38]

TABLE 1-continued
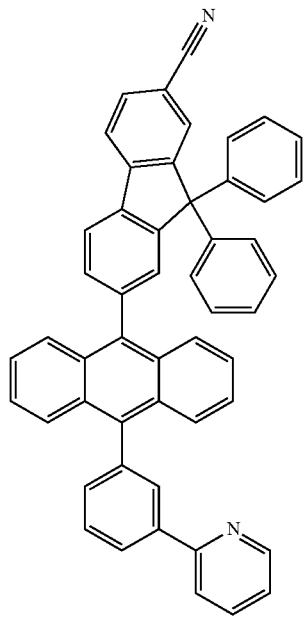 [SMILES: N#Cc1ccc2c(c1)C(c1ccccc1)(c1ccccc1)c1cc(-c3c4ccccc4c(-c4cccc(-c5ccccn5)c4)c4ccccc34)ccc1-2]
[Formula 1-39]
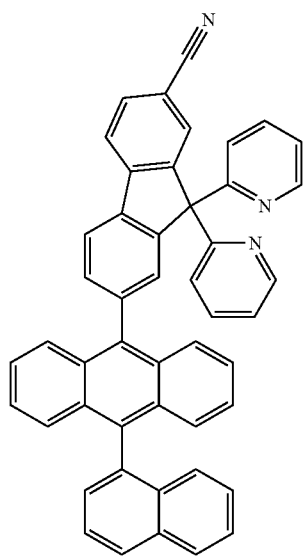 [SMILES: N#Cc1ccc2c(c1)C(c1ccccn1)(c1ccccn1)c1cc(-c3c4ccccc4c(-c4cccc5ccccc45)c4ccccc34)ccc1-2]
[Formula 1-40]
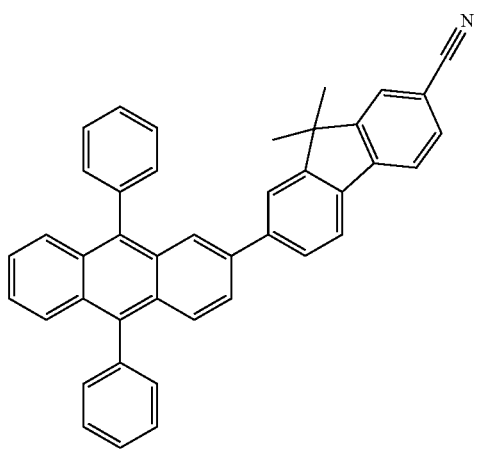 [SMILES: CC1(C)c2cc(C#N)ccc2-c2ccc(-c3ccc4c(-c5ccccc5)c5ccccc5c(-c5ccccc5)c4c3)cc21]
[Formula 2-1]

TABLE 1-continued
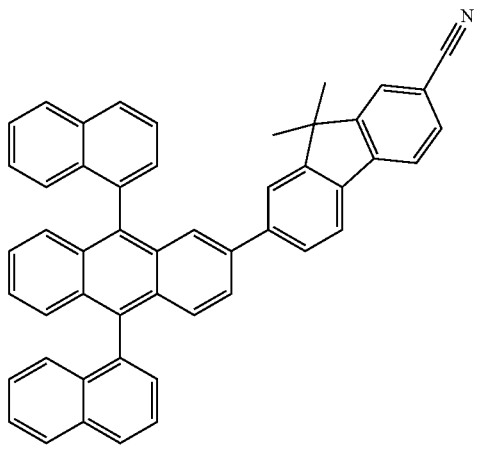 [SMILES: CC1(C)c2cc(C#N)ccc2-c2ccc(-c3ccc4c(-c5cccc6ccccc56)c5ccccc5c(-c5cccc6ccccc56)c4c3)cc21]
[Formula 2-2]
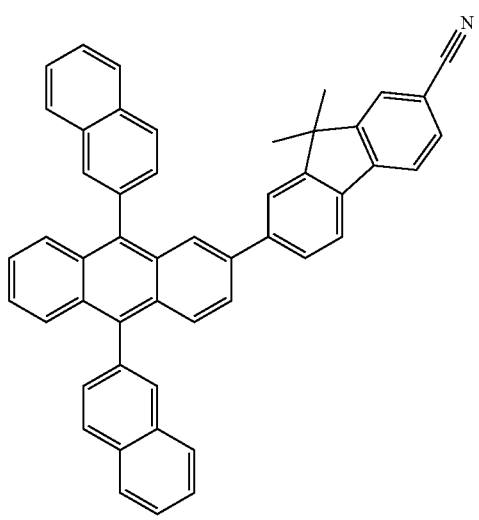 [SMILES: CC1(C)c2cc(C#N)ccc2-c2ccc(-c3ccc4c(-c5ccc6ccccc6c5)c5ccccc5c(-c5ccc6ccccc6c5)c4c3)cc21]
[Formula 2-3]
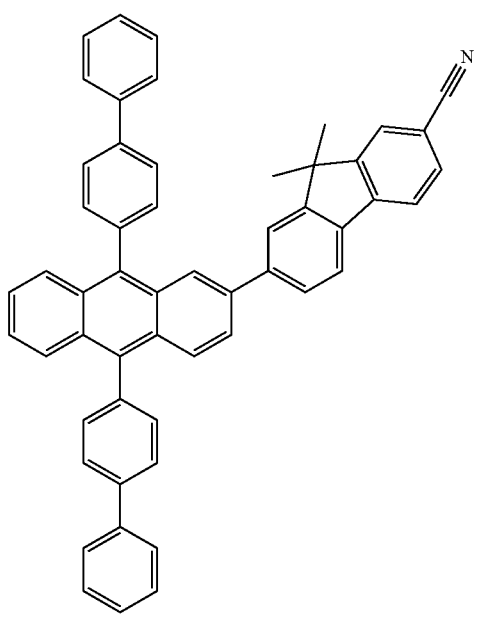 [SMILES: CC1(C)c2cc(C#N)ccc2-c2ccc(-c3ccc4c(-c5ccc(-c6ccccc6)cc5)c5ccccc5c(-c5ccc(-c6ccccc6)cc5)c4c3)cc21]
[Formula 2-4]

TABLE 1-continued
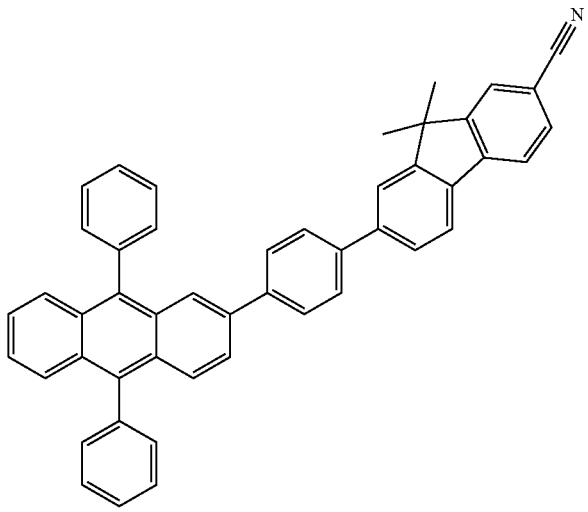 [SMILES: CC1(C)c2cc(C#N)ccc2-c2ccc(-c3ccc(-c4ccc5c(-c6ccccc6)c6ccccc6c(-c6ccccc6)c5c4)cc3)cc21]
[Formula 2-5]
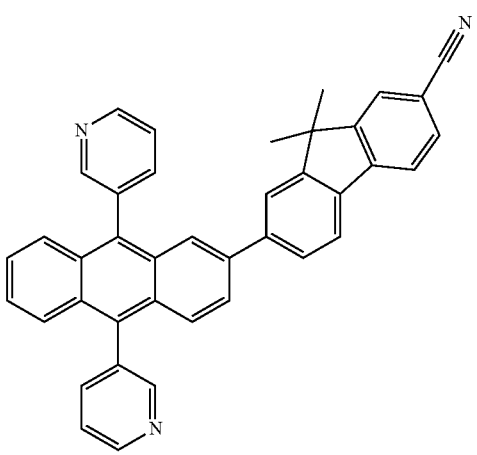 [SMILES: CC1(C)c2cc(C#N)ccc2-c2ccc(-c3ccc4c(-c5cccnc5)c5ccccc5c(-c5cccnc5)c4c3)cc21]
[Formula 2-6]
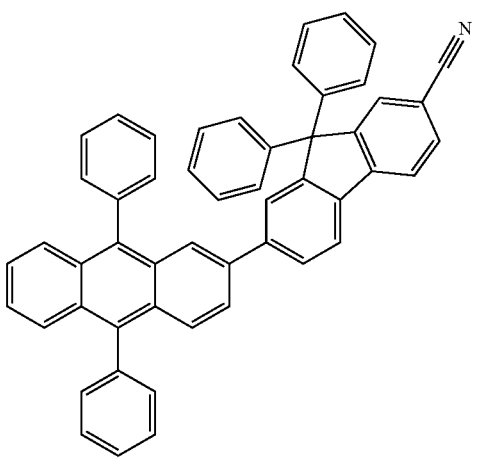 [SMILES: N#Cc1ccc2c(c1)C(c1ccccc1)(c1ccccc1)c1cc(-c3ccc4c(-c5ccccc5)c5ccccc5c(-c5ccccc5)c4c3)ccc1-2]
[Formula 2-7]

TABLE 1-continued
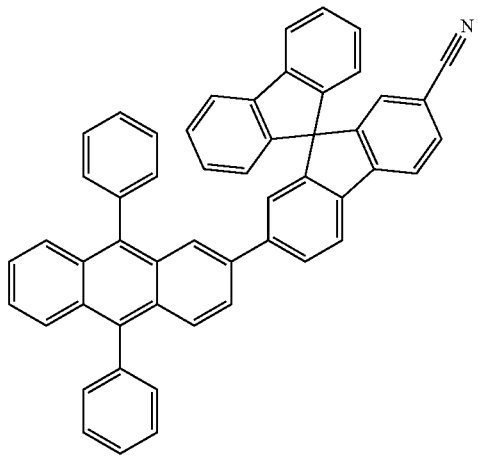 [SMILES: N#Cc1ccc2c(c1)C1(c3ccccc3-c3ccccc31)c1cc(-c3ccc4c(-c5ccccc5)c5ccccc5c(-c5ccccc5)c4c3)ccc1-2]
[Formula 2-8]
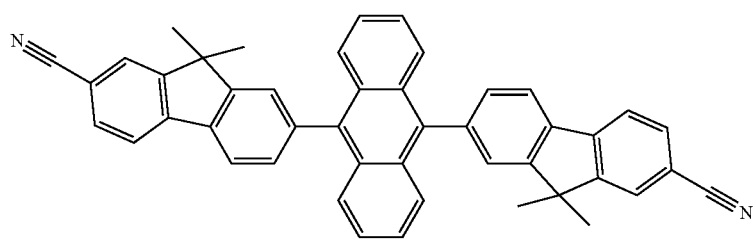 [SMILES: CC1(C)c2cc(C#N)ccc2-c2ccc(-c3c4ccccc4c(-c4ccc5c(c4)C(C)(C)c4cc(C#N)ccc4-5)c4ccccc34)cc21]
[Formula 3-1]
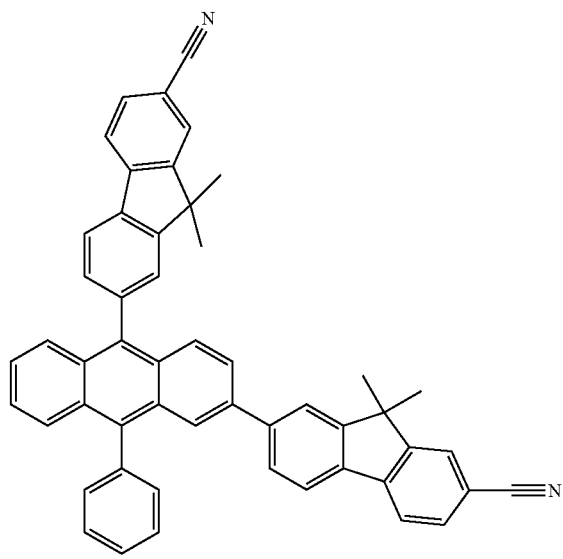 [SMILES: CC1(C)c2cc(C#N)ccc2-c2ccc(-c3ccc4c(-c5ccc6c(c5)C(C)(C)c5cc(C#N)ccc5-6)c5ccccc5c(-c5ccccc5)c4c3)cc21]
[Formula 3-2]

TABLE 1-continued

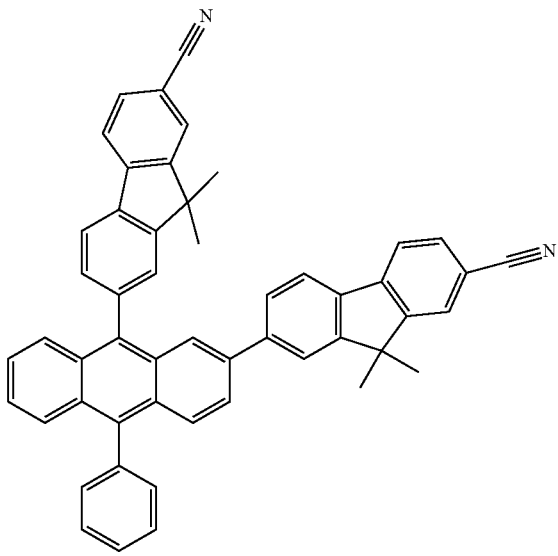 [SMILES: CC1(C)c2cc(C#N)ccc2-c2ccc(-c3ccc4c(-c5ccccc5)c5ccccc5c(-c5ccc6c(c5)C(C)(C)c5cc(C#N)ccc5-6)c4c3)cc21]

[Formula 3-3]

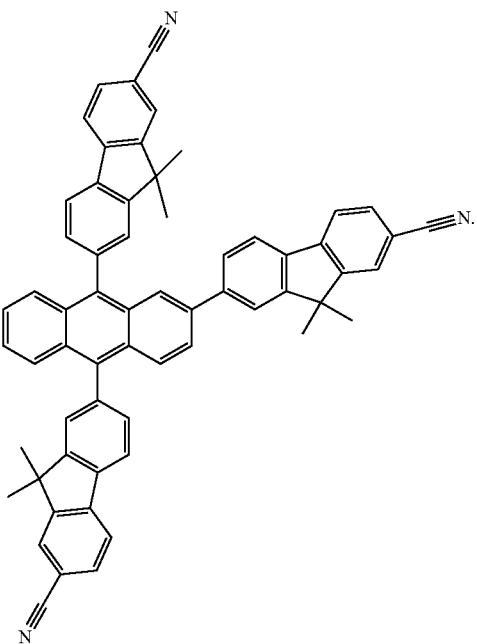 [SMILES: CC1(C)c2cc(C#N)ccc2-c2ccc(-c3ccc4c(-c5ccc6c(c5)C(C)(C)c5cc(C#N)ccc5-6)c5ccccc5c(-c5ccc6c(c5)C(C)(C)c5cc(C#N)ccc5-6)c4c3)cc21]

[Formula 3-4]

7. The organic electronic device of claim 1, wherein the organic electronic device is an organic light emitting device, and has a forward direction structure or a reverse direction structure.

8. The organic electronic device of claim 1, wherein the organic electronic device is an organic light emitting device, and the organic material layer further comprises at least one layer selected from a hole injection layer, a hole transporting layer, and a layer which transports and injects holes simultaneously,
wherein at least one of the hole injection layer, the hole transporting layer, and the layer which transports and injects holes simultaneously comprises the compound.

9. The organic electronic device of claim 1, wherein the organic material layer comprising the compound further includes an n-type dopant selected from the group consisting of an alkali metal, an alkali metal compound, an alkaline earth metal, an alkaline earth metal compound, and a combination thereof.

10. The organic electronic device of claim 9, wherein the n-type dopant is included in an amount from 1% by weight to 70% by weight based on a total weight of the composition of the organic material layer comprising the compound.

* * * * *